(12) United States Patent
Tanaka

(10) Patent No.: US 8,188,119 B2
(45) Date of Patent: May 29, 2012

(54) PYRIDINE DERIVATIVES SUBSTITUTED WITH HETEROCYCLIC RING AND γ-GLUTAMYLAMINO GROUP, AND ANTIFUNGAL AGENTS CONTAINING SAME

(75) Inventor: Keigo Tanaka, Tsukuba (JP)

(73) Assignee: Eisai R&D Management Co., Ltd, Tokyo (JP)

( * ) Notice: Subject to any disclaimer, the term of this patent is extended or adjusted under 35 U.S.C. 154(b) by 322 days.

(21) Appl. No.: 12/574,368

(22) Filed: Oct. 6, 2009

(65) Prior Publication Data

US 2010/0105737 A1 Apr. 29, 2010

Related U.S. Application Data

(60) Provisional application No. 61/108,201, filed on Oct. 24, 2008.

(30) Foreign Application Priority Data

Oct. 24, 2008 (JP) .................... 2008-274060

(51) Int. Cl.
*C07D 413/14* (2006.01)
*A61K 31/444* (2006.01)

(52) U.S. Cl. ........ 514/333; 514/340; 514/341; 546/256; 546/268.4; 546/272.1

(58) Field of Classification Search .................. None
See application file for complete search history.

(56) References Cited

U.S. PATENT DOCUMENTS

| | | | |
|---|---|---|---|
| 4,551,532 A | 11/1985 | Hozumi et al. |
| 4,576,956 A | 3/1986 | Makisumi et al. |
| 4,720,493 A | 1/1988 | Kawakita et al. |
| 4,785,010 A | 11/1988 | Zoller et al. |
| 4,935,520 A | 6/1990 | Nojima et al. |
| 5,034,393 A | 7/1991 | Hackler et al. |
| 5,068,340 A | 11/1991 | Nakamura et al. |
| 5,070,082 A | 12/1991 | Murdock et al. |
| 5,208,247 A | 5/1993 | Trova et al. |
| 5,296,484 A | 3/1994 | Coghlan et al. |
| 5,328,921 A | 7/1994 | Trova et al. |
| 5,350,749 A | 9/1994 | Hackler et al. |
| 5,371,086 A | 12/1994 | Takemoto et al. |
| 5,691,136 A | 11/1997 | Lupski et al. |
| 5,691,336 A | 11/1997 | Dorn et al. |
| 5,710,171 A | 1/1998 | Dinsmore et al. |
| 5,747,518 A | 5/1998 | Yoshikawa et al. |
| 5,852,042 A | 12/1998 | Jakobi et al. |
| 5,945,431 A | 8/1999 | Jin et al. |
| 6,022,884 A | 2/2000 | Mantlo et al. |
| 6,080,767 A | 6/2000 | Klein et al. |
| 6,174,905 B1 | 1/2001 | Suzuki et al. |
| 6,200,975 B1 | 3/2001 | Carling et al. |
| 6,235,728 B1 | 5/2001 | Golik et al. |
| 6,255,318 B1 | 7/2001 | Bedard et al. |
| 6,310,203 B1 | 10/2001 | Carling et al. |
| 6,313,127 B1 | 11/2001 | Waterson et al. |
| 6,319,944 B1 | 11/2001 | Claiborne et al. |
| 6,340,690 B1 | 1/2002 | Bachand et al. |
| 6,380,218 B1 | 4/2002 | Marfat et al. |
| 6,407,116 B1 | 6/2002 | Kajino et al. |
| 6,414,013 B1 | 7/2002 | Fancelli et al. |
| 6,596,718 B1 | 7/2003 | Flohr et al. |
| 6,630,495 B1 | 10/2003 | Cooke et al. |
| 7,179,804 B2 | 2/2007 | Amegadzie et al. |
| 7,179,822 B2 | 2/2007 | Bunker et al. |
| 7,687,525 B2 | 3/2010 | Suzuki et al. |
| 7,691,882 B2 | 4/2010 | Tanaka et al. |
| 7,754,726 B2 | 7/2010 | Lang et al. |
| 7,829,585 B2 | 11/2010 | Nakamoto et al. |
| 7,932,272 B2 | 4/2011 | Nakamoto et al. |
| 2002/0011495 A1 | 1/2002 | Clemmons |
| 2002/0111495 A1 | 8/2002 | Magee et al. |
| 2003/0045554 A1 | 3/2003 | Sankaranarayanan |
| 2003/0114491 A1 | 6/2003 | Kim et al. |
| 2003/0191158 A1 | 10/2003 | Magee |
| 2003/0195169 A1 | 10/2003 | Gillman et al. |
| 2004/0038239 A1 | 2/2004 | Tsukahara et al. |
| 2004/0044040 A1 | 3/2004 | Neubert et al. |

(Continued)

FOREIGN PATENT DOCUMENTS

DE 19727117 A1 1/1999

(Continued)

OTHER PUBLICATIONS

Office Action for U.S. Appl. No. 12/109,834, mailed on Jan. 19, 2011.
Office Action for U.S. Appl. No. 12/109,834, mailed on Jun. 17, 2011.
Office Action for U.S. Appl. No. 12/109,834, mailed on Nov. 10, 2010.
Office Action for U.S. Appl. No. 12/343,889, mailed on Dec. 31, 2009.
Office Action for U.S. Appl. No. 12/343,889, mailed on Jan. 3, 2011.
Office Action for U.S. Appl. No. 12/343,889, mailed on Jul. 11, 2011.
Office Action for U.S. Appl. No. 12/343,889, mailed on Oct. 2, 2009.
Response to New Zealand Office Action for Patent Application No. 592416, dated Nov. 14, 2011.

(Continued)

*Primary Examiner* — Zinna Northington Davis
(74) *Attorney, Agent, or Firm* — Birch, Stewart, Kolasch & Birch, LLP

(57) ABSTRACT

The present invention provides an antifungal agent which has excellent antifungal action, and which is also excellent in terms of its properties, and in particular its solubility in water and safety. The present invention discloses a compound represented by the following formula (I) or a salt thereof.

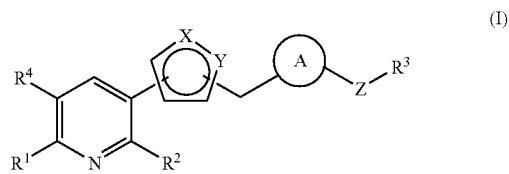

(I)

wherein $R^1$, $R^2$, $R^3$, $R^4$, A, X, Y, and Z are defined in the specification.

17 Claims, 2 Drawing Sheets

U.S. PATENT DOCUMENTS

| | | |
|---|---|---|
| 2004/0152730 A1 | 8/2004 | Farina et al. |
| 2004/0198773 A1 | 10/2004 | Hart et al. |
| 2005/0119229 A1 | 6/2005 | Ammermann et al. |
| 2006/0264419 A1 | 11/2006 | Schiemann et al. |
| 2006/0270637 A1 | 11/2006 | Gravestock et al. |
| 2007/0060619 A1 | 3/2007 | Burns et al. |
| 2007/0105904 A1 | 5/2007 | Tanaka et al. |
| 2007/0105943 A1 | 5/2007 | Nakamoto et al. |
| 2007/0167493 A1 | 7/2007 | Sankaranarayanan |
| 2008/0090846 A1 | 4/2008 | Bridger et al. |
| 2008/0275244 A1 | 11/2008 | Niijima et al. |
| 2009/0062348 A1 | 3/2009 | Nakamoto et al. |
| 2009/0082403 A1 | 3/2009 | Tanaka et al. |
| 2009/0227799 A1 | 9/2009 | Nakamoto et al. |
| 2009/0233883 A1 | 9/2009 | Matsukura |
| 2010/0099718 A1 | 4/2010 | Matsukura et al. |
| 2010/0160379 A1 | 6/2010 | Tanaka et al. |
| 2010/0168173 A1 | 7/2010 | Tanaka et al. |
| 2010/0331282 A1 | 12/2010 | Matsukura |
| 2011/0195999 A1 | 8/2011 | Nakamoto et al. |

FOREIGN PATENT DOCUMENTS

| | | |
|---|---|---|
| EP | 0124067 A1 | 11/1984 |
| EP | 0124154 A2 | 11/1987 |
| EP | 0274867 A2 | 7/1988 |
| EP | 0326326 A2 | 1/1989 |
| EP | 0414386 A1 | 2/1991 |
| EP | 0533130 A1 | 3/1993 |
| EP | 0976744 A1 | 2/2000 |
| EP | 1216980 A1 | 6/2002 |
| EP | 1217000 A1 | 6/2002 |
| EP | 1229034 A1 | 8/2002 |
| EP | 1275301 A1 | 1/2003 |
| EP | 1275653 A1 | 1/2003 |
| EP | 1 369 420 A1 | 12/2003 |
| EP | 1 669 348 A1 | 6/2006 |
| EP | 1782811 A1 | 5/2007 |
| EP | 1 944 303 A1 | 7/2008 |
| GB | 919073 | 2/1963 |
| JP | 54-2325 A | 1/1979 |
| JP | 57-179192 A | 11/1982 |
| JP | 59-73575 A | 4/1984 |
| JP | 59-84824 A | 5/1984 |
| JP | 59-206353 A | 11/1984 |
| JP | 61-148178 A | 7/1986 |
| JP | 62-277368 A | 12/1987 |
| JP | 64-3162 A | 1/1989 |
| JP | 1246264 A | 10/1989 |
| JP | 3-66689 A | 3/1991 |
| JP | 3-161470 A | 7/1991 |
| JP | 5-213877 A | 8/1993 |
| JP | 5-294935 A | 11/1993 |
| JP | 7-25853 A | 1/1995 |
| JP | 8-12579 A | 1/1996 |
| JP | 8-175993 A | 7/1996 |
| JP | 9-507245 A | 7/1997 |
| JP | 10-505600 A | 6/1998 |
| JP | 11-152275 A | 6/1999 |
| JP | 2000-504336 A | 4/2000 |
| JP | 2000-178243 A | 6/2000 |
| JP | 2001-515464 A | 9/2001 |
| JP | 2001-522834 A | 11/2001 |
| JP | 2001-525365 A | 12/2001 |
| JP | 2001-525802 A | 12/2001 |
| JP | 2001-527083 A | 12/2001 |
| JP | 2002-275159 A | 9/2002 |
| JP | 2002-284766 A | 10/2002 |
| JP | 2002-537396 A | 11/2002 |
| JP | 2002-544162 A | 12/2002 |
| JP | 2003-506466 A | 2/2003 |
| JP | 2004-529154 A | 9/2004 |
| JP | 2005-033079 A | 2/2005 |
| JP | 2005-526097 A | 9/2005 |
| JP | 2005-526751 A | 9/2005 |
| JP | 2006-519247 A | 8/2006 |
| VU | WO-03/059903 A2 | 7/2003 |
| WO | WO-86/03203 A1 | 6/1986 |
| WO | WO-93/12084 A1 | 6/1993 |
| WO | WO 93/12124 A1 | 6/1993 |
| WO | 7-502503 A | 3/1995 |
| WO | WO 95/09159 A1 | 4/1995 |
| WO | WO 95/18795 A1 | 7/1995 |
| WO | WO-96/09294 A1 | 3/1996 |
| WO | WO-97/27852 A1 | 8/1997 |
| WO | WO-97/28128 A1 | 8/1997 |
| WO | WO-98/25883 A1 | 6/1998 |
| WO | WO-98/50029 A1 | 11/1998 |
| WO | WO-99/24404 A1 | 5/1999 |
| WO | WO-99/48492 A1 | 9/1999 |
| WO | WO-99/50247 A1 | 10/1999 |
| WO | WO-00/07991 A1 | 2/2000 |
| WO | WO-00/51998 A1 | 9/2000 |
| WO | WO-00/62778 A1 | 10/2000 |
| WO | WO-00-73283 A1 | 12/2000 |
| WO | WO-01/11966 A1 | 2/2001 |
| WO | WO-01/21584 A1 | 3/2001 |
| WO | WO-01/25181 A1 | 4/2001 |
| WO | WO 01/26652 A1 | 4/2001 |
| WO | WO-01/27096 A1 | 4/2001 |
| WO | WO 01/36003 A2 | 5/2001 |
| WO | WO-01/51456 A2 | 7/2001 |
| WO | WO-01/53274 A1 | 7/2001 |
| WO | WO-01/74779 A1 | 10/2001 |
| WO | WO-02/00651 S2 | 1/2002 |
| WO | WO-02/04626 A1 | 1/2002 |
| WO | WO-02/06275 A1 | 1/2002 |
| WO | WO-02/22583 A2 | 3/2002 |
| WO | WO-02/060875 A1 | 8/2002 |
| WO | WO-02/060896 A1 | 8/2002 |
| WO | WO-02/060898 A1 | 8/2002 |
| WO | WO-02/083645 A1 | 10/2002 |
| WO | WO-02/085897 A1 | 10/2002 |
| WO | WO 03/006628 A2 | 1/2003 |
| WO | WO-03/027095 A1 | 4/2003 |
| WO | WO-03/031435 A1 | 4/2003 |
| WO | WO 03/037860 A2 | 5/2003 |
| WO | WO-03/045385 A1 | 6/2003 |
| WO | WO 03/045920 A1 | 6/2003 |
| WO | WO-03/068232 A1 | 8/2003 |
| WO | WO-03/068235 A1 | 8/2003 |
| WO | WO 03/068747 A1 | 8/2003 |
| WO | WO-03/091226 A1 | 11/2003 |
| WO | WO-03/091227 A1 | 11/2003 |
| WO | WO-2004/000813 A1 | 12/2003 |
| WO | WO-2004/014366 A1 | 2/2004 |
| WO | WO-2004/014370 A2 | 2/2004 |
| WO | WO-2004/029027 A1 | 4/2004 |
| WO | WO-2004/033432 A1 | 4/2004 |
| WO | WO-2004/048567 A2 | 6/2004 |
| WO | WO-2004/052280 A2 | 6/2004 |
| WO | WO-2004/089931 A1 | 10/2004 |
| WO | WO-2005/033079 A1 | 4/2005 |
| WO | WO-2006/016548 A1 | 2/2006 |
| WO | Wo-2006/106711 A1 | 10/2006 |
| WO | WO-2007/052615 A1 | 5/2007 |
| WO | WO 2007/056215 A2 | 5/2007 |
| WO | WO 2008/136324 A1 | 11/2008 |
| WO | WO-2009/081970 A1 | 7/2009 |
| WO | WO-2009/084621 A1 | 7/2009 |

OTHER PUBLICATIONS

Response to Thai Office Action for Patent Application No. 0901004757, dated Dec. 9, 2010.

Response to U.S. Office Action for U.S. Appl. No. 12/109,834, mailed on Dec. 10, 2010.

Response to U.S. Office Action for U.S. Appl. No. 12/109,834, mailed on Dec. 16, 2011.

Response to U S. Office Action for U.S. Appl. No. 12/108,834, mailed on Mar. 8, 2011.

Response to U.S. Office Action for U.S. Appl. No. 12/343,889, mailed on Apr. 20, 2011.

Response to U.S. Office Action for U.S. Appl. No. 12/343,889, mailed on Jan. 10, 2012.

Response to U.S. Office Action for U.S. Appl. No. 12/343,889, mailed on Mar. 30, 2010.

Response to U.S. Office Action for U.S. Appl. No. 12/343,889, mailed on Oct. 30, 2009.
Response to Vietnamese Office Action for Patent Application No. 1-2011-01026, dated Jun. 13, 2011.
Chandran et al., "Synthesis of 8-Aminoquinolines: Part II—8-Guidance Derivatives," Journal of Scientific & Industrial Research (1952), 11B, pp. 129-132.
Hata, "New Approaches to Antifungal Drugs for the Treatment of Fungal and Protozoal Infections, Ravuconazole and Beyond: New Targets and Pre-clinical Strategies," The SMI's 12th Annual Conference, Superbugs and Superdrugs, Mar. 18, 2010, Crowne Plaza London—St. James, 44 pages.
Lo et al., "Development of highly selective and sensitive probes for hydrogen peroxide," Communication, Chem Comm, The Royal Society of Chemistry, 2003, pp. 2728-2729.
U.S. Office Action issued May 14, 2010 for copending U.S. Appl. No. 11/887,249.
U.S. Office Action issued May 4, 2010 for copending U.S. Appl. No. 11/658,901.
Tom A Connors et al., "Biologicals & Immunologicals", Exp. Opin. Ther. Patents (1995) vol. 5, No. 9, pp. 873-885.
International Search Report issued Aug. 31, 2010, in corresponding PCT International Patent Application No. PCT/JP2010/060502.
European Search Report issued Jul. 29, 2010, in corresponding European Patent Application No. 05768893.9.
European Search Report issued Jul. 19, 2010, in corresponding European Patent Application No. 06730370.1.
Pernak, J. et al., "Synthesis and antimicrobial activities of new pyridinium and benzimidazolium chlorides," Eur. J. Med. Chem., vol. 36 (2001) pp. 313-320.
Pregnolato, M. et al., "3H-[1,2]Dithiolo[3,4-b]pyridine-3-thione and its derivatives Synthesis and antimicrobial activity," IL FARMACO, vol. 55, (2000) pp. 669-679.
Amendment Order dated Dec. 9, 2010, issued in Thailand Patent Application No. 0901004757, with English translation.
Examination Report issued Aug. 31, 2010, in Pakistan Patent Application No. 879/2009.
Examination Report issued Sep. 20, 2011, in New Zealand Patent Application No. 592416.
International Preliminary Report on Patentability issued May 17, 2011, in PCT International Application No. PCT/JP2009/005559.
International Search Report issued Nov. 24, 2009, in PCT International Application No. PCT/JP2009/005559.
Notification of Result of Preliminary Examination issued May 20, 2011, in Vietnam Patent Application No. 1-2011-01026, with English translation.
Office Action issued Oct. 20, 2011, Indian Patent Application No. 3678/DELNP/2008.
Chan et al., "Discovery of 1,6-Naphthylridines as a Novel Class of Potent and Selective Human Cytomegalovirus Inhibitors," Journal of Medicinal Chemistry (1999), vol. 42, No. 16, pp. 3023-3025.
Kushner et al., "Experimental Chemotherapy of Tuberculosis. II. The Synthesis of Pyrazinamides and Related Compounds," Journal of the American Chemical Society (1952), vol. 74, pp. 3617-3621.
Lucas et al., "Facile Synthesis of a Library of 9-Alkyl-8-benzyl-9H-purin-6-ylamine Derivatives," Journal of Combinatorial Chemistry (2001), vol. 3, No. 6, pp. 518-520.
Tanaka et al., "An Effective Synthesis of a (Pyridin-3-yl)isoxazole via 1,3-Dipolar Cycloaddition Using ZnCl2: Synthesis of a (2-Aminopyridin-3-yl)isoxazole Derivative and its Antifungal Activity," Chemistry Letters, vol. 39, No. 10, pp. 1033-1035, The Chemical Society of Japan, Oct. 5, 2010.
Database Chemcats [Online] Chemical Abstracts Service, Columbus, Ohio, US; XP002600785 Database accession No. 2059288788 Order No. (ON): 6700755 & Chembridge Corporation: "ChemBridge Screening Library" Jun. 9, 2010, ChemBridge Corporation, San Diego (USA).
Database Chemcats [Online] Chemical Abstracts Service, Columbus, Ohio, US; XP002600787 Database accession No. 2084604173 Order No. (ON): STK143803 & Vitas-M: "Vitas-M Screening Collection" Jul. 13, 2010, Vitas-M, Hodynski Blv. 15, Moskow, (RU).
Database Registry [Online] Chemical Abstracts Service, Columbus, Ohio, US; Jul. 16, 2002, XP0022600783 Database accession No. 438574-588-3(RN).
Database Registry [Online] Chemical Abstracts Service, Columbus, Ohio, US; Jun. 18, 2002, XP002600784 Database accession No. 431922-54(RN) abstract.
Database Registry [Online] Chemical Abstracts Service, Columbus, Ohio, US; Oct. 18, 2004, XP002600786 Database accession No. 764713-41-9(RN) abstract.
Extended European Search Report dated Oct. 11, 2010, issued in corresponding European Patent Application No. 07828273.8.
Office Action issued Oct. 13, 22010, in copending U.S. Appl. No. 11/658,901.
English translation of the International Search Report dated Aug. 31, 2010 for Application No. PCT/JP2010/060502.
Extended European Search Report dated Jan. 12, 2011 for Application No. 08868067.3.
Pakistan Office Action dated Jul. 30, 2009 for Application No. 1524/2008.
Saudi Arabian Office Action dated Jan. 24, 2011 for Application No. 108290840.
Accession No. 2020895193, Chemcats, Interchim Intermediates, TK030913, "Pyridine, 3-[-[(4-methoxyphenyl)methyl]-1,2,4-oxadiazol-5-yl]," Jul. 9, 2007, CAS Registry No. (RN): 438574-99-3.
Accession No. 2021278791, Chemcats, Akos Screening Library, Feb. 7, 2006, AKL-P-1720927, "Pyridine, 3-[5-[(2-methoxyphenyl)methyl]-1,2,4-oxadiazol-3-yl]-,"9 Feb. 7, 2006, CAS Registry No. 434304-24-2.
Accession No. 2036647688, Chemcats, Ambinter Stock Screening Collection, STK143803. "Pyridine, 3-[5-[(4-methoxyphenyl)methyl]-1,2,4-thiadiazol-2-yl]-," Jun. 1, 2007, CAS Registry No. (RN): 764713-41-9.
Accession No. 2025887145, Chcats, Aurora Screening Library, kbsa-0118093, "Pyridine, 3-[5-[(4-methoxyphenyl)methyl]-1,2,4-oxadiazol-3-yl]-," Jan. 1, 2007. CAS Registry No. (RN): 431922-54-2.
Gardner et al., "Genome sequence of the human malaria parasite *Plasmodium falciparum*." Nature, vol. 419, pp. 498-511, (2002).
Ikizier, et al. "Antimicrobial activities of some 4H-1,2,4-triazoles" Indian Journal of Pharmaceutical Sciences, 1999, vol. 61, No. 5, pp. 271-274.
Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, pp. 2427-2437 (2003).
Kajino et al., "Preparation and formulation of quinazoline derivatives as allergy inhibitors". Database CA [Online], Chemical Abstract Service, XP0025132525, Database Accession No. 216905, 1999.
Modena et al.: "Plant growth regulating activities of 2-[2-(arylamino)-2-oxoethyl]benzoic acids", Database Accession No. 1993:597690, Abstract, Farmaco, vol. 48. No. 4, pp. 567-572, 1993, XP002512527.
Naik et al., "Glucosamine inhibits Inositol Acylation of the Glycosylphosphalidylinositol Anchors in Intraerythrocytic *Plasmodium falciparuml*." The Journal of Biological Chemistry, vol. 278, No. 3, pp. 2036-2042, (2003).
An Office Action from co-pending U.S. Appl. No. 11/589,128, mailed May 7, 2009.
Oshima et al., "Non-Prostanoid Thromboxane $A_2$ Receptor Antagonists with a Dibenzoxepin Ring System. 2," J. Med. Chem. vol. 35, pp. 3402-3413, (1992).
Okawa et al., "Pyrido[2,3-d]pyrimidine Derivatives Synthesis via the Intermolecular Aza-Wittig Reaction/Heterocyclization and the Crystal Structure," Synthesis, Database CA [Online] Chemical Abstract Service, XP002512524, Database accession No. 677971 (1998), pp. 1467-1475 (1998).
Piechaczak et al., "Monoamine oxidase inhibitors. VII. Derivatives of quinolinecarboxylic acids," Database Accession No. 1966:75701, Abstract, Acta Poloniae Pharmaceutica, vol. 23, No. 1, pp. 7-13, 1966, XP002512526.
Shinkai et al., "N-Acylphenylalanines and Related Compounds A New Class of Oral Hypoglycemic Agents," J. Med. Chem., vol. 31, pp. 2092-2097, (1988).

Supplementary European Search Report dated Feb. 6, 2009 for corresponding European Application No. 04788159.4.

Vippagunta et al., "Crystalline Solids", Advanced Drug Delivery Reviews. 2001, pp. 3-26, vol. 48.

Chan et al., Database Accession No. 8422493, Abstract, Bioorganic & Medicinal Chemistry Letters, 1999, pp. 2583-2586., vol. 9, No. 17, Database Crossfire Beilstein, Beilstein Institut Zur Foerderung Der Chemischen Wissenschaften, Frankfurt Am Main, DE, XP-002512523.

An Office Action for co-pending U.S. Appl. No. 10/573,890, mailed Jul. 29, 2009.

Guillory, "Generation of Polymorphs, Hydrates, Solvates, and Amorphous Solids", *Polymorphism in Pharmaceutical Solids*, 1999, pp. 183-226, ed. Harry G. Brittain, Marcel Dekker, Inc., New York.

Chang, K. Y. et al., "Synthesis and Structure-Activity Relationships of Quaternary Ammonium Cephalosporins with 3-Pyrazolypyridinium Derivaties," Bioorganic & Medicinal Chemistry Letters (2000) vol. 10, No. 11, pp. 1211-1214.

Plate, R. et al., "Synthesis and Muscarinic Activities of 3-(Pyrazolyi)-1,2,5,6-tetrahydropyridine Derivatives," Bioorganic & Medicinal Chemistry Letters (1996) vol. 4, No. 2, pp. 227-237.

Vrzheschch, P. V. et al., "Supercooperativity in platelet aggregation: Substituted pyridyl isozazoles, a new class of supercooperative platelet aggregation inhibitors," FEBS Letters (1994) vol. 351, No. 2, pp. 168-170.

Lukevics, E. et al., "Synthesis and cytotoxicity of silyl- and carbonyl-substituted isoxazoles," Chemistry of Heterocyclic Compounds (2000) vol. 36, No. 10, pp. 1226-1231.

Ex parte Quayle Action issued Mar. 31, 2011, in copending U.S. Appl. No. 11/658,901.

Extended European Search Report issued Apr. 18, 2011, in European Patent Application No. 08740624.5.

Freshney et al., Culture of Animal Cells, A Manual of Basic Technique, 1983, Wiley & Sons, Inc., New York pp. 7-9.

Office Action issued Jun. 17, 2011, in related U.S. Appl. No. 12/109,834.

Office Action for U.S. Appl. No. 12/343,889, mailed on Feb. 14, 2012.

Satyanarayana, et al., "Studies on the synthesis and biological activity of 3- arylaminomethyl-5-(3-pyridyl)-1, 3, 4-oxadiazole-2-thione derivatives," Bolletino Chimico Farmaceutico, 2001, vol. 140, No. 4, p. 228-232.

Shinkal et al., "N-Acylphenylaianines and Related Compounds. A New Class of Oral Hypoglycemic Agents," J. Med. Chem., vol. 31, pp. 2092-2097, (1988).

Supplementary European Search Report dated Feb. 6, 2009 for corresponding European Application No. 04788159 4.

International Search Report dated May 20, 2008 for corresponding International Application No. PCT/JP2008/057851.

Vippagunta et al., "Crystalline Solids", Advanced Drug Delivery Reviews, 2001. pp. 3-26, vol. 48.

Chan et al., Database Accession No. 8422493. Abstract, Bioorganic & Medicinal Chemistry Letters. 1999, pp. 2583-2586., vol. 9, No. 17, Database Crossfire Beilstein, Beilstein Institut Zur Foerderung Der Chemischen Wissenschaften, Frankfurt Am Main, DE, XP-002512523.

Office Action from co-pending U.S. Appl. No. 10/573,890, mailed July 29, 2009.

Guillory, "Generation of Polymorphs, Hydrates, Solvates and Amorphous Solids". *Polymorphism in Pharmaceutical Solids*, 1999, pp. 183-226, et. Harry G. Brittain, Marcei Dekker, Inc. New York.

Tanaka et al., "An Effective Lewis Acid-Mediated 1,3-Dipolar Cycloaddition of Nitrile Oxide Using Acetylene: Synthesis of a (2-Aminopyridin-3-yl) isoxazole Derivative and its Application to Novel Antifungal Agents, " pp. 1-8, 2008.

Chang, K. Y. et al., "Synthesis and Structure-Activity Relationships of Quaternary Ammonium Cephalosporins with 3-Pyrazolylpyridinium Derivatives." Bioorganic & Medicinal Chemistry Letters (2000) vol. 10, No. 11, pp. 1211-1214.

Plate, R. et al., "Synthesis and Muscarinic Activities of 3-(Pyrazoiyl)-1,2,5,6-tetrahydropyridine Derivatives," Bioorganic & Medicinal Chemistry Letters (1996) vol. 4, No. 2, pp. 227-237.

Vrzheschoh, P. V. et al., "Supercooperativity in platelet aggregation: Substituted pyridyl isoxazoles, a new class of supercooperative platelet aggregation inhibitors, " FEBS Letters (1994) vol. 351, No. 2, pp. 168-170.

Lukevics, E. et al., "Synthesis and cytotoxicity of silyl- and carbonyl-substituted isoxazoles, " Chemistry of Heterocyclic Compounds (2000) vol. 36, No. 10, pp. 1226-1231.

PYRIDINE DERIVATIVES SUBSTITUTED WITH HETEROCYCLIC RING AND γ-GLUTAMYLAMINO GROUP, AND ANTIFUNGAL AGENTS CONTAINING SAME

This Nonprovisional application claims priority under 35 U.S.C. §119(e) on U.S. Provisional Application Nos. 61/108,201 filed on Oct. 24, 2008, and claims priority under 35 U.S.C. §119(a) on Patent Application No(s). 2008-274060 filed in Japan on Oct. 24, 2008, the entire contents of each of which are hereby incorporated by reference.

TECHNICAL FIELD

The present invention relates to novel pyridine derivatives substituted with a heterocyclic ring and a γ-glutamylamino group, and to antifungal agents containing the same.

BACKGROUND ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different a virulent pathogen, it is shown that the problem of infectious disease will not ends as long as there are underlying diseases that diminish the immune functions of patients. Consequently, new strategies for infectious diseases control, including the problem of drug-resistant pathogen, will be one of the important issues in the soon-to-come aged society.

In the field of antifungal agents, heretofore, for instance, amphotericine B which is based on a polyene skeleton, fluconazole, itraconazole and voriconazole which are based on an azole skeleton, or the like, have been developed for the treatment of deep seated mycoses. Most of pre-existing drugs already available commercially have similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety. As the related art relevant to antifungal agents based on such a novel mechanism, Patent Documents 1 and 2 describe pyridine derivatives which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI (Glycosylphosphatidylinositol)-anchored proteins to the cell wall being inhibited.

In light of this situation, Patent document 3 proposes heterocyclic ring-substituted pyridine derivatives as an antifungal agent that has excellent antifungal action not seen in conventional antifungal agents, and is also superior in terms of its properties, safety, and metabolic stability.

Meanwhile, Non-Patent document 1 discloses compounds represented by the following formula as a prodrug in which a γ-glutamyl group has been introduced.

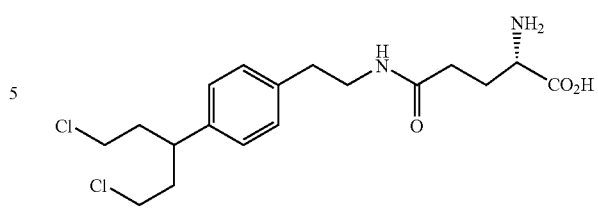

Patent document 1: WO 02/04626 Pamphlet

Patent document 2: WO 05/033079 Pamphlet

Patent document 3: WO 07/052,615 Pamphlet

Non-patent document 1: Exp. Opin. Ther. Patents (1995), 5 (9): 873-885

DISCLOSURE OF INVENTION

Problems to be Solved by the Invention

However, the water-soluble prodrugs known up to now do not have an excellent antifungal action based on the inhibition of the GPI-anchored protein transport process, nor are they excellent in terms of solubility in water, stability in an aqueous solution, or safety and pharmacokinetics and the creation of a better antifungal agent based on the inhibition of the GPI-anchored protein transport process, which is practical as an injection, is desired.

In light of this situation, it is an object of the present invention to provide an antifungal agent which has excellent antifungal action based on the inhibition of the GPI-anchored protein transport process, and which is also excellent in terms of solubility in water, its stability in an aqueous solution, and its safety and pharmacokinetics.

Means for Solving the Problems

As a result of diligent research conducted in light of the above situation, the inventors perfected the present invention upon discovering that pyridine derivatives substituted with a heterocyclic ring and a γ-glutamylamino group, which is represented by the formula:

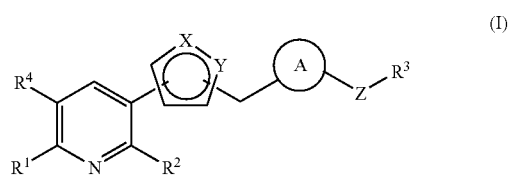

has excellent antifungal action and is also excellent in terms of solubility in water, its stability in an aqueous solution, and its safety and pharmacokinetics.

Specifically, the present invention provides:

[1] A compound represented by the following formula (I) or a salt thereof:

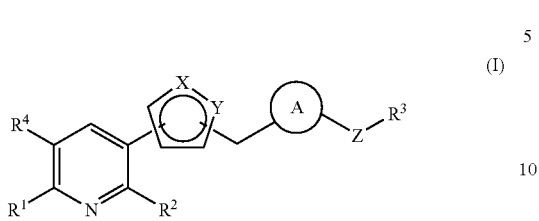

(I)

wherein $R^1$ represents a hydrogen atom, a halogen atom, an amino group, $R^{11}$—NH— (wherein $R^{11}$ represents a $C_1$ to $C_6$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^2$ represents a group represented by the formula:

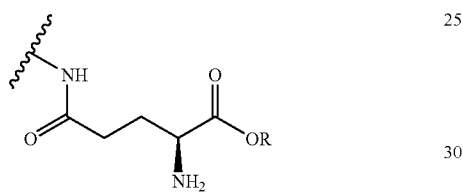

one of X and Y is a nitrogen atom while the other is a nitrogen atom or an oxygen atom;

ring A represents a 5- or 6-member heteroaryl ring or benzene ring which may have a halogen atom or 1 or 2 $C_1$ to $_6$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

$R^3$ represents a hydrogen atom or a halogen atom, or represents a $C_{1-6}$ alkyl group, a $C_{3-8}$ cycloalkyl group, a $C_{6-10}$ aryl group, a 5- or 6-member heteroaryl group, or a 5- or 6-member non-aromatic heterocyclic group, each of which may have 1 or 2 substituents selected from substituent group α;

$R^4$ represents a hydrogen atom or a halogen atom; and

R represents a hydrogen atom or a $C_{1-6}$ alkyl group which may be substituted with a dimethylamino group,

[Substituent Group α]

a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group and a $C_{2-6}$ alkynyl group.

[2] The compound or the salt thereof according to item [1], wherein a partial structure represented by the formula (II):

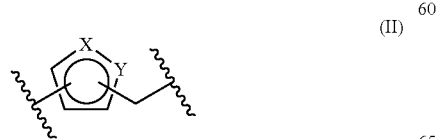

(II)

is a partial structure selected from the following group:

(III)

(IV)

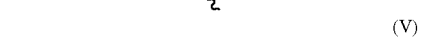

(V)

(VI)

[3] The compound or the salt thereof according to item [1], wherein one of X and Y is a nitrogen atom and the other is an oxygen atom.

[4] The compound or the salt thereof according to item [3], wherein a partial structure represented by the formula (II):

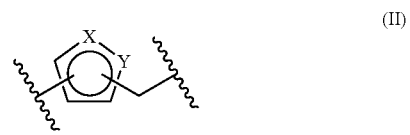

(II)

is a partial structure selected from the following formula (III):

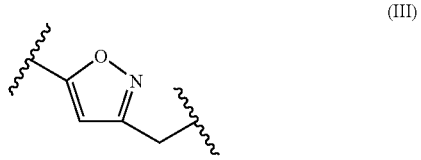

(III)

or is a partial structure selected from the following formula (IV):

(IV)

[5] The compound or the salt thereof according to item [1], wherein X and Y are both nitrogen atoms.

[6] The compound or the salt thereof according to item [5], wherein a partial structure represented by the formula (II):

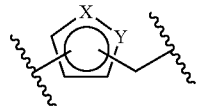

is a partial structure selected from the following formula (V):

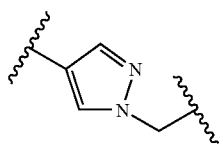

or is a partial structure selected from the following formula (VI):

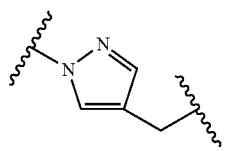

[7] The compound or the salt thereof according to any one of items [1] to [6], wherein R represents a hydrogen atom, a methyl group, an ethyl group, or a 2-dimethylaminoethyl group.
[8] The compound or the salt thereof according to item [7], wherein $R^1$ represents a hydrogen atom, an amino group, or a $C_{1-6}$ alkoxy $C_{1-6}$ alkyl group.
[9] The compound or the salt thereof according to any one of items [1] to [6], wherein $R^1$ represents an amino group, and R represents a hydrogen atom, a methyl group, an ethyl group, or a 2-dimethylaminoethyl group.
[10] The compound or the salt thereof according to any one of items [1] to [6], wherein $R^1$ represents an amino group, and R represents a methyl group, an ethyl group, or a 2-dimethylaminoethyl group.
[11] The compound or the salt thereof according to any one of items [1] to [10], wherein the ring A represents a pyridine ring, a benzene ring, a furan ring, a thiophene ring, or a pyrrole ring.
[12] The compound or the salt thereof according to item [11], wherein the ring A represents a pyridine ring or a benzene ring.
[13] The compound or the salt thereof according to any one of items [1] to [12], wherein Z represents an oxygen atom, —$CH_2O$—, or —$OCH_2$—.
[14] A pharmaceutical composition comprising the compound or the salt thereof according to any one of items [1] to [13].
[15] A medicament comprising the compound or the salt thereof according to any one of items [1] to [13].
[16] An antifungal agent comprising as an active ingredient the compound or the salt thereof according to any one of items [1] to [13].
[17] A method for preventing and/or treating a fungal infection comprising administering a pharmaceutically effective dose of the compound or the salt thereof according to any one of items [1] to [13].
[18] Use of the compound or the salt thereof according to any one of items [1] to [13] for manufacturing an antifungal agent.

Advantageous Effects of the Invention

The compound represented by formula (I) or the salt thereof (hereinafter referred to simply as "the compound of the present invention") 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physicochemical properties, such as solubility in water, its stability in an aqueous solution as well as its safety and pharmacokinetics, thereby making the compound of the present invention extremely useful as a preventive or therapeutic agent for fungal infections

MODE FOR CARRYING OUT THE INVENTION

Figure 1:
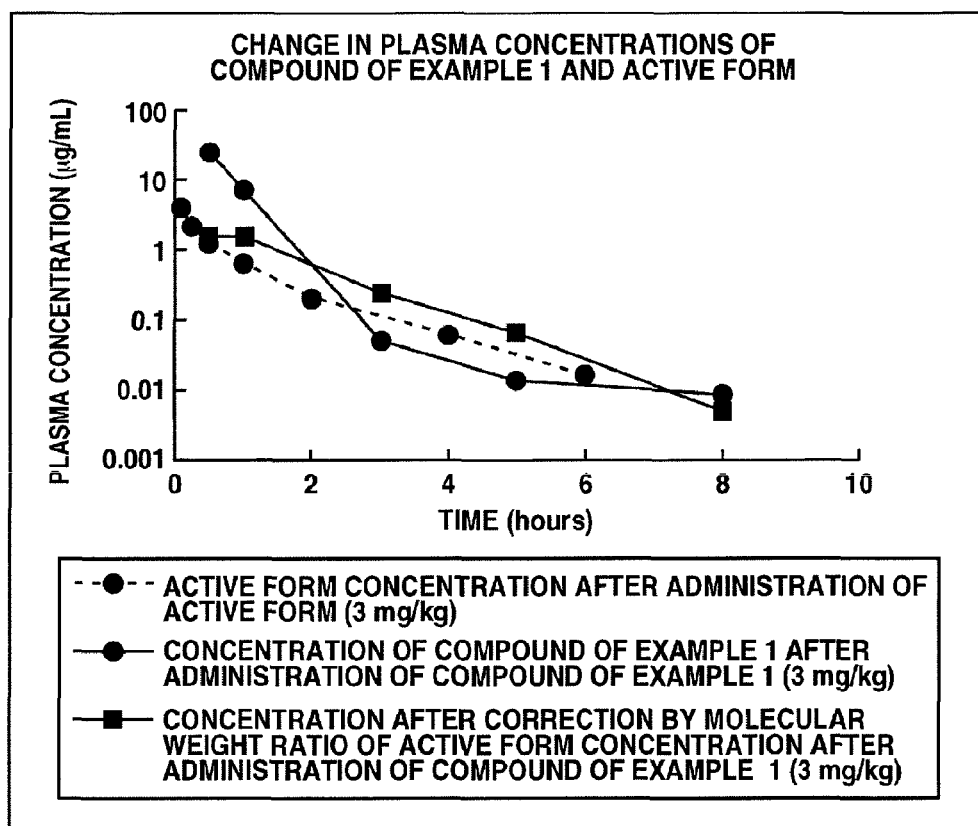
FIG. 1 shows the results of measuring the plasma concentration of the compound of Example 1 and the active form, which is a parent compound of the compound of Example 1, measured by pharmacokinetic evaluation in mice in one embodiment of the present invention.

The present invention is explained below in more detail by reference to the symbols and the terms used herein being defined and the following examples. It should be noted that the present invention is not limited to the following embodiments, however, and various modifications can be made without departing from the gist thereof.
Herein, a structural formula of a compound sometimes represents a certain isomer for convenience of description. However, compounds according to the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either one of two isomers or a mixture of both isomers. Thus, the compounds according to the present invention may be either optically active compounds having an asymmetric carbon atom in their molecules or their racemates, and are not restricted to either of them but include both. Furthermore, the compounds according to the present invention may exhibit crystalline polymorphism, but likewise are not restricted to any one of these, but may be in any one of these crystal forms or exist as a mixture of two or more crystal forms. The compounds according to the present invention also include both anhydrous and solvates such as hydrated forms.
The term "$C_{1-6}$ alkyl group" used in the present specification refers to a straight-chain or branched-chain alkyl group with 1 to 6 carbon atoms which is a monovalent group induced by removal of any one hydrogen atom from an aliphatic hydrocarbon with 1 to 6 carbon atoms. Specifically, examples of "$C_{1-6}$ alkyl group" includes a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2,-trimethylpropyl group, a 1,2,2-trimethylpropyl group, a 1-ethyl-1-methylpropyl group, a 1-ethyl-2-methylpropyl group or the like, preferably a methyl group, an ethyl group, a n-propyl group, an isopropyl group, a n-butyl group, an isobutyl group, a sec-butyl group or a tert-butyl group or the like.

The term "$C_{2-6}$ alkenyl group" used in the present specification refers to a straight-chain or branched-chain alkenyl group with 2 to 6 carbon atoms which may contain 1 or 2 double bonds. Specifically, examples of "$C_{2-6}$ alkenyl group" include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexanedienyl group or the like, preferably an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification refers to a straight-chain or branched-chain alkynyl chain with 2 to 6 carbon atoms which may contain 1 or 2 triple bonds. Specifically, examples of "$C_{2-6}$ alkynyl group" include an ethynyl group, a 1-propynyl group, a 2-propynyl group, a 1-butynyl group, a 2-butynyl group, a 3-butynyl group, a pentynyl group, a hexynyl group, a hexanediynyl group or the like, preferably an ethynyl group, a 1-propynyl group, a 2-propynyl group, a 1-butynyl group, a 2-butynyl group, a 3-butynyl group or the like.

The term "$C_{3-6}$ cycloalkyl group" used in the present specification refers to a cyclic aliphatic hydrocarbon group with 3 to 8 carbon atoms. Specifically, examples of "$C_{3-8}$ cycloalkyl group" include a cyclopropyl group, a cyclobutyl group, a cyclopentyl group, a cyclohexyl group, a cycloheptyl group, a cyclooctyl group or the like, preferably a cyclopropyl group, a cyclobutyl group, a cyclopentyl group, a cyclohexyl group or the like.

The term "$C_{1-6}$ alkoxy group" used in the present specification refers to a group in which an oxygen atom is bonded to terminus of the "$C_{1-6}$ alkyl group" defined above. Specifically, examples of "$C_{1-6}$ alkoxy group" include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropxy group, a 1-ethyl-2-methylpropoxy group or the like, preferably a methoxy group, an ethoxy group, a n-propoxy group, an isopropoxy group, a n-butoxy group, an isobutoxy group, a sec-butoxy group, a tert-butoxy group or the like.

The term "hydroxyl $C_{1-6}$ alkyl group" used in the present specification refers to a group in which any of the hydrogen atoms in a "$C_{1-6}$ alkyl group" as defined above has been replaced by a hydroxyl group. Specifically, examples of "hydroxyl $C_{1-6}$ alkyl group" include a hydroxymethyl group, a 1-hydroxyethyl group, a 2-hydroxyethyl group, a 1-hydroxy-n-propyl group, a 2-hydroxy-n-propyl group, a 3-hydroxy-n-propyl group, a 1-hydroxy-isopropyl group, a 2-hydroxy-isopropyl group, a 3-hydroxy-isopropyl group, a 1-hydroxy-tert-butyl group or the like, preferably a hydroxymethyl group, a 1-hydroxyethyl group, a 2-hydroxyethyl group or the like.

The term "cyano $C_{1-6}$ alkyl group" used in the present specification refers to a group in which any of the hydrogen atoms in a "$C_{1-6}$ alkyl group" as defined above has been replaced by a cyano group. Specifically, examples of "cyano $C_{1-6}$ alkyl group" include a cyanomethyl group, a 1-cyanoethyl group, a 2-cyanoethyl group, a 1-cyano-n-propyl group, a 2-cyano-n-propyl group, a 3-cyano-n-propyl group, a 1-cyano-isopropyl group, a 2-cyano-isopropyl group, a 3-cyano-isopropyl group, a 1-cyano-tert-butyl group or the like, preferably a cyanomethyl group, a 1-cyanoethyl group, a 2-cyanoethyl group or the like.

The term "$C_{1-6}$ alkoxycarbonyl group" used in the present specification refers to a group in which a carbonyl group is bonded to terminus of the "$C_{1-6}$ alkoxy group" defined above. Specifically, examples of "$C_{1-6}$ alkoxycarbonyl group" include a methoxycarbonyl group, an ethoxycarbonyl group, a n-propoxycarbonyl group, an isopropoxycarbonyl group or the like.

The term "$C_{1-6}$ alkoxycarbonyl $C_{1-6}$ alkyl group" used in the present specification refers to a group in which the "$C_{1-6}$ alkyl group" defined above is bonded to terminus of the "$C_{1-6}$ alkoxycarbonyl group" defined above. Specifically, examples of the "$C_{1-6}$ alkoxycarbonyl $C_{1-6}$ alkyl group" include a methoxycarbonyl methyl group, a methoxycarbonyl ethyl group, an ethoxycarbonyl methyl group, an ethoxycarbonyl ethyl group or the like.

The term "$C_{6-10}$ aryl group" used in the present specification refers to an aromatic hydrocarbon cyclic group with 6 to 10 carbon atoms. Specifically, examples of "$C_{6-10}$ aryl group" include a phenyl group, a 1-naphthyl group, a 2-naphthyl group, an indenyl group, an azulenyl group, a heptalenyl group or the like, preferably a phenyl group, a 1-naphthyl group, 2-naphthyl group or the like.

The term "$C_{1-6}$ alkoxy $C_{1-6}$ alkyl group" used in the present specification refers to a group in which any of the hydrogen atoms in a "$C_{1-6}$ alkyl group" as defined above has been replaced by a "$C_{1-6}$ alkoxy group" as defined above. Specifically, examples of "$C_{1-6}$ alkoxy $C_{1-6}$ alkyl group" include a methoxymethyl group, an ethoxymethyl group, a n-propoxymethyl group, a methoxyethyl group, an ethoxyethyl group or the like.

The term "halogen atom" used in the present specification refers a fluorine atom, a chlorine atom, a bromine atom or an iodine atom.

The term "hetero atom" used in the present specification refers to a nitrogen atom, a sulfur atom or an oxygen atom.

The term "5- or 6-member heteroaryl ring" used in the present specification refers to an aromatic ring in which the number of atoms making up the ring is 5 or 6, and 1 or more hetero atoms are included in the atoms making up the ring. Specifically, examples of "5- or 6-member heteroaryl ring" include a furan ring, a thiophene ring, a pyrrole ring, a pyridine ring, a pyrazine ring, a pyridazine ring, a pyrimidine ring, a triazole ring (a 1,2,3-triazole ring, a 1,2,4-triazole ring, etc.), a tetrazole ring (a 1H-tetrazole ring, a 2H-tetrazole ring, etc.), a thiazole ring, a pyrazole ring, an oxazole ring, an isoxazole ring, an isothiazole ring, an oxadiazole ring, a thiadiazole ring or the like.

The term "5- or 6-member heteroaryl group" used in the present specification refers to a monovalent group induced by removing 1 hydrogen atom from any position in an aromatic ring in which the number of atoms making up the ring is 5 or 6 and 1 or more hetero atoms are included in the atoms making up the ring. Specifically, examples of "5- or 6-member heteroaryl group" include a furyl group (a 2-furyl group or a 3-furyl group, etc.), a thienyl group (a 2-thienyl group or a 3-thienyl group, etc.), a pyrrolyl group (a 1-pyrrolyl group, a 2-pyrrolyl group or a 3-pyrrolyl group, etc.), a pyridyl group (a 2-pyridyl group, a 3-pyridyl group, a 4-pyridyl group, etc.), a pyrazinyl group, a pyridazinyl group (a 3-pyridazinyl group or a 4-pyridazinyl group, etc.), a pyrimidinyl group (a 2-pyrimidinyl group, a 4-pyrimidinyl group or a 5-pyrimidinyl group, etc.), a triazolyl group (a 1,2,3-triazolyl group or a 1,2,4-triazolyl group, etc.), a tetrazolyl group (a 1H-tetrazolyl group or a 2H-tetrazolyl group, etc.), a thiazolyl group (a 2-thiazolyl group, a 4-thiazolyl group or a 5-thiazolyl group, etc.), a pyrazolyl group (a 3-pyrazolyl group or a 4-pyrazolyl group, etc.), an oxazolyl group (a 2-oxazolyl group, a 4-oxazolyl group or a 5-oxazolyl group, etc.), an isoxazolyl group (a 3-isoxazolyl group, a 4-isoxazolyl group or a 5-isoxazolyl group, etc.), an isothiazolyl group (a 3-isothiazolyl group, a 4-isothiazolyl group or a 5-isothiazolyl group, etc.), an oxadiazolyl group, a thiadiazolyl group or the like.

The term "5- or 6-member non-aromatic heterocyclic group" used in the present specification refers to a monovalent group induced by removing 1 hydrogen atom from any position in a non-aromatic ring in which the number of atoms making up the ring is 5 or 6 and 1 or more hetero atoms are included in the atoms making up the ring. Specifically, examples of "5- or 6-member non-aromatic heterocyclic group" include a pyrrolidinyl group, a piperadinyl group, a piperidinyl group, a morpholinyl group, a tetrahydrofuryl group, a tetrahydropyranyl group or the like.

The term "may have 1 or 2 substituents" used in the specification means that there may be 1 or 2 substituents in any combination in sites capable of substituting.

$R^1$ represents a hydrogen atom, a halogen atom, an amino group, a $C_{1-6}$ alkyl group, a $C_{1-6}$ alkoxy group, a $C_{1-6}$ alkylamino group, a hydroxyl $C_{1-6}$ alkylamino group, or a $C_{1-6}$ alkoxy $C_{1-6}$ alkyl group, and preferably represents a hydrogen atom, an amino group or a $C_{1-6}$ alkoxy $C_{1-6}$ alkyl group, with a methoxymethyl group being preferred as the $C_{1-6}$ alkoxy $C_{1-6}$ alkyl group.

R preferably represents a hydrogen atom, a methyl group, an ethyl group, or 2-dimethylaminoethyl group.

One of X and Y is a nitrogen atom while the other is a nitrogen atom or an oxygen atom.

The partial structure which contains X and Y and which is represented by formula (II) below:

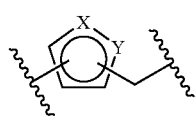

(II)

has a structure such as those shown below, preferably with the left side bound to the 3-position of a pyridine ring via a single bond, and the right side bound to an A ring via a methylene group:

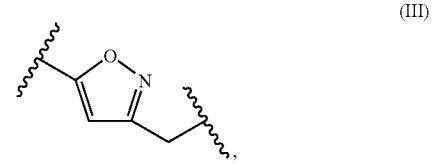

(III)

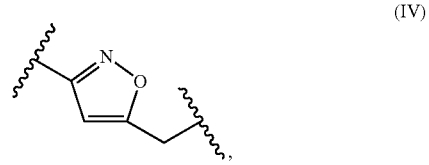

(IV)

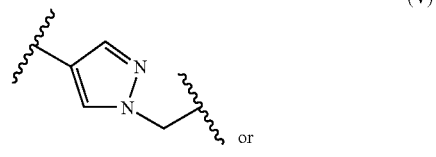

(V)

or

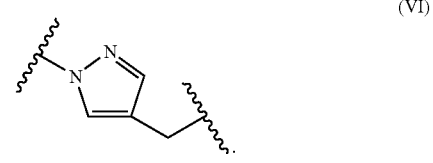

(VI)

In the case of the partial structure of formula (III), for example, the parent compound of the compound of the present invention, that is, the compound prior to the introduction of a γ-glutamylamino group, is shown by the following formula:

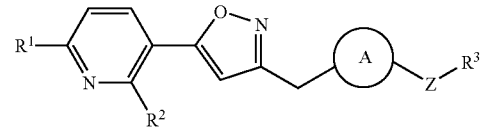

It is preferable that one of X and Y be a nitrogen atom and the other be an oxygen atom, or that both X and Y be nitrogen atoms, and when one of X and Y is a nitrogen atom and the other is an oxygen atom, the partial structure which contains X and Y, and which is represented by the following formula (II):

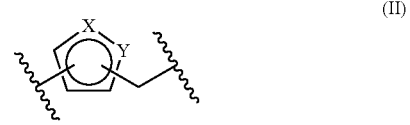

(II)

has a structure such as that shown by formulae (III) or (IV) below, preferably with the left end bound to the 3-position of a pyridine ring via a single bond and the right end linked to an A ring via a methylene group:

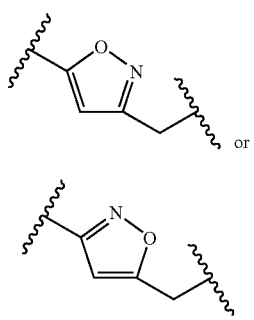

while if X and Y are both nitrogen atoms, the partial structure which contains X and Y, and which is represented by the following formula (II):

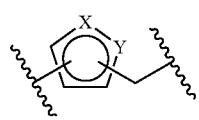

has a structure such as that shown by formula (V) or (VI) below, preferably with the left end bound to the 3-position of a pyridine ring via a single bond and the right end bound to an A ring via a methylene group:

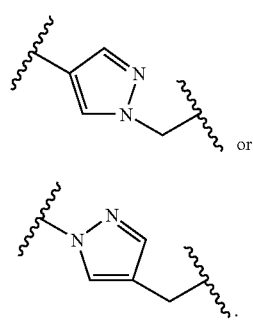

A ring A represents a 5- or 6-member heteroaryl ring or a benzene ring which may have a halogen atom or 1 or 2 $C_{1-6}$ alkyl groups, and preferably represents a pyridine ring, a benzene ring, a furan ring, a thiophene ring or a pyrrole ring, or more preferably a pyridine ring, a benzene ring or a thiophene ring, still more preferably a pyridine ring or a benzene ring.

Z preferably represents a single bond, a methylene group, an ethylene group, an oxygen atom, a sulfur atom, —$CH_2O$—, —$OCH_2$—, —NH—, —$NHCH_2$—, —$CH_2NH$—, —$CH_2$—S—, or —$SCH_2$—. Of these a methylene group, an oxygen atom, —$CH_2O$— or —$OCH_2$— is preferred, and an oxygen atom, —$CH_2O$— or —$OCH_2$— is especially preferred.

$R^3$ represents a hydrogen atom, halogen atom, a $C_{1-6}$ alkyl group, a $C_{3-8}$ cycloalkyl group, a $C_{6-10}$ aryl group or a 5- or 6-member ring heteroaryl group which may have 1 or 2 substituents each selected from substituent group α:
[Substituent Group α]
a halogen atom, a cyano group, a $C_{1-6}$ alkyl group, a $C_{1-6}$ alkoxy group, $C_{1-6}$ alkoxycarbonyl group, a $C_{3-8}$ cycloalkyl group, a $C_{2-6}$ alkenyl group and a $C_{2-6}$ alkynyl group.

Examples of preferable groups as $R^3$ include a n-butyl group, a cyclopropyl group, a phenyl group, a fluorophenyl group, a furyl group, a chlorofuryl group, a methylfuryl group, a thienyl group, a bromothienyl group, a methylthienyl group, a pyridyl group and a methylpyridyl group, more preferably a n-butyl group, a cyclopropyl group, a phenyl group, a fluorophenyl group, a pyridyl group or a methylpyridyl group.

Z and $R^3$ may constitute the substituent of ring A in any combination. Preferable examples of $R^3$—Z— as the substituent of ring A constituted in this way include a phenoxy group, a benzyloxy group, a 2-fluoro-benzyloxy group, a 3-fluoro-benzyloxy group, a 4-fluoro-benzyloxy group, a pyridin-2-yloxymethyl group, a 6-methyl-pyridin-2-yloxymethyl group, a pyridin-2-ylmethoxy, a 6-methyl-pyridin-2-ylmethoxy group, a 4-methyl-pyridin-2-ylmethoxy group, a butoxymethyl group and a cyclopropylmethoxy group and the like.

Examples of the term "salt" used in the present specification include salts with inorganic acids, salts with organic acids, salts with inorganic bases, salts with organic bases, salts with acidic or basic amino acids or the like. Among these salts, it is preferable that the salts used herein be pharmaceutically acceptable. There are no particular restrictions on the number of acids or bases which form the salts.

Preferable examples of the salts with the inorganic acids include salts with hydrochloric acid, hydrobromic acid, sulfuric acid, nitric acid, phosphoric acid or the like. Preferable examples of the salts with the organic acids include salts with acetic acid, succinic acid, fumaric acid, maleic acid, tartaric acid, citric acid, lactic acid, stearic acid, benzoic acid, methanesulfonic acid, ethanesulfonic acid, trifluoroacetic acid, p-toluenesulfonic acid or the like. Preferable examples of the salts with the inorganic bases include salts of lithium salts, sodium salts, potassium salts, calcium salts or the like. Preferable examples of the salts with the organic bases include salts with methylamine, ethylamine, tert-butylamine, triethylamine, piperidine, morpholine or the like.

Preferable examples of the salts with the acidic amino acids include salts with aspartic acid, glutamic acid or the like. Preferable examples of the salts with the basic amino acids include salts with arginine, lysine, ornithine or the like.

The term "antifungal agent" used in the present specification refers to a preventive agent or a therapeutic agent for fungal infection.

The compounds according to the present invention or salts thereof can be formulated into tablets, powders, fine granules, granules, coated tablets, capsulates, syrups, troches, inhalants, suppositories, injections, ointments, eye ointments, tapes, eye drops, nose drops, ear drops, cataplasms, lotions or the like, by the conventional methods.

Such formulation can be achieved by using typical diluents, binders, lubricants, colorants, flavorants, and, as necessary, stabilizers, emulsifiers, absorbefacients, surfactants, pH modulators, preservatives, antioxidants or the like, and materials commonly used as ingredients of pharmaceutical preparations according to the conventional methods. For example, an oral preparation can be produced by combining a compound of the present invention or a pharmaceutically acceptable salt thereof with a diluent, and if required, a binder, a disintegrating agent, a lubricant, a colorant, a flavorant or the like, and formulating the mixture into powders, fine granules, granules, tablets, coated tablets, capsules or the like according to the conventional methods.

Examples of the materials include animal and vegetable oils such as soy bean oil, beef tallow, and synthetic glyceride;

hydrocarbons such as liquid paraffin, squalane, and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acids ester, sorbitan fatty acid ester, polyoxyethylene sorbitan fatty acid ester, polyoxyethylene hydrogenated castor oil, and polyoxyethylene polyoxypropylene block co-polymer; water-soluble polymers such as hydroxyethyl cellulose, polyacrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Examples of the diluents include lactose, corn starch, white sugar, glucose, mannitol, sorbitol, crystalline cellulose, silicon dioxide or the like. Examples of the binders include polyvinyl alcohol, polyvinyl ether, methylcellulose, ethylcellulose, gum Arabic, tragacanth, gelatin, shellac, hydroxypropyl methylcellulose, hydroxypropyl cellulose, polyvinylpyrrolidone, polypropylene glycol-polyoxyethylene block co-polymer, and meglumine or the like. Examples of disintegrating agents include starch, agar, gelatin powder, crystalline cellulose, calcium carbonate, sodium hydrogencarbonate, calcium citrate, dextrin, pectin, calcium carboxymethyl cellulose or the like. Examples of lubricants include magnesium stearate, talc, polyethylene glycol, silica, hydrogenated vegetable oil or the like. Examples of colorants include those pharmaceutically acceptable. Examples of flavorants include cocoa powder, peppermint camphor, aromatic powder peppermint oil, Borneo camphor, cinnamon powder or the like. Tablets and granules may be coated with sugar, or if required, other appropriate coatings can be made. Solutions, such as syrups or injectable preparations, to be administered can be formulated by combining a compound according to the present invention or a pharmaceutically acceptable salt thereof with a pH modulator, a solubilizing agent, an isotonizing agent or the like, and if required, with an auxiliary solubilizing agent, a stabilizer or the like, according to the conventional methods. Methods for manufacturing external preparations are not limited and such preparations can be manufactured by the conventional methods. Specifically, various materials typically used for manufacturing pharmaceuticals, quasi drugs, cosmetics or the like can be used as base materials for the external formulation. More specifically, examples of base materials to be used include animal and vegetable oils, minerals oils, ester oils, wax, higher alcohols, fatty acids, silicone oil, surfactants, phospholipids, alcohols, polyhydric alcohols, water-soluble polymers, clay minerals, pure water or the like. Furthermore, external preparations of the present invention can contain, as required, pH modulators, antioxidants, chelating agents, antibacterial/antifungal agents, colorants, odoriferous substances or the like. But this does not limit the type of base materials that are to be used in the external preparations of the present invention. If required, the preparation may contain differentiation inducers, blood flow improving agents, antimicrobial agents, antiphologistics, cell activators, vitamins, amino acids, humectants, keratolytic agents or the like. The amount of the base materials listed above is adjusted within a concentration range used for producing typical external preparations.

When administering the compound of the present invention or a salt thereof, the forms of the compounds are not limited in particular, and the compound can be given orally or parenterally by the conventional method. For instance, the compound can be administered as a dosage form such as tablets, powders, granules, capsules, syrups, troches, inhalants, suppositories, injections, ointments, eye ointments, tapes, eye drops, nasal drops, ear drops, cataplasms and lotions.

Dose of a medicament according to the present invention can be selected appropriately according to symptom severity, age, sex, body weight, forms of administration, type of salts, specific type of disease or the like.

The does varies remarkably depending on the patient's disease, symptom severity, age and sex, drug susceptibility or the like. An oral preparation according to the present invention can be generally administered once or several time at a dose of from 1 to 10000 mg/adult/day, preferably from 10 to 2000 mg/adult/day. An injection according to the present invention can be generally administered at a dose of from 0.1 to 10000 mg/adult/day, preferably from 1 to 2000 mg/adult/day.

[General Synthesis Methods]

The method for manufacturing the compounds represented by formula (I) according to the present invention (hereinafter referred to as compounds (I)) is discussed here.

Manufacturing Method 1—Method for Manufacturing Compound (I)

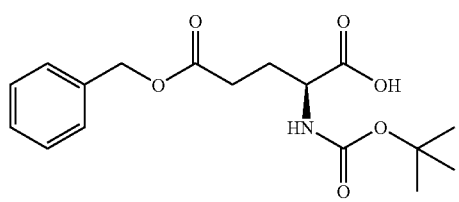

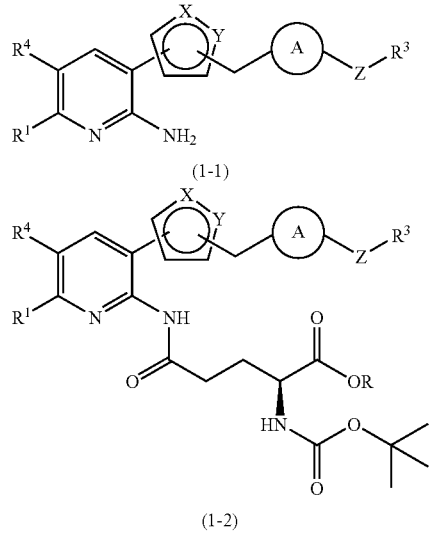

(1-1)

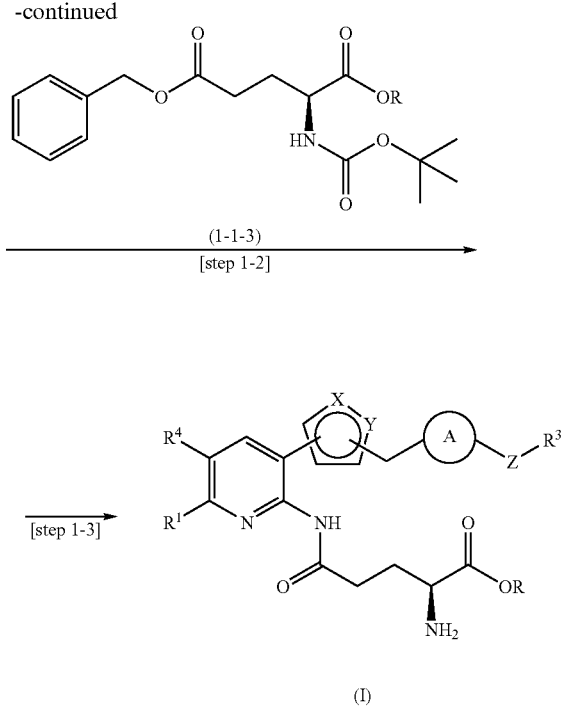

(1-1-3)

[step 1-2]

(1-2)

[step 1-3]

(I)

(wherein ring A, R$^1$, R$^3$, R$^4$, X, Y, Z, and R are defined the same as above.)

Compound (1-1) can be manufactured by the methods described in the following Reference Examples, etc. Compound (1-1) can also be manufactured by the method described in U.S. Patent Publication No. 2007/0105904 (A1), for example. Compound (1-1-2) which is a commercially available product can be used as is, or can be manufactured by the known method from the commercially available product.

[Step 1-1]

This step is a step in which Compound (1-1-3) is obtained by reacting Compound (1-1-1) with Compound (1-1-2) in the presence of a condensation agent.

There are no particular restrictions on the solvent used in this reaction, as long as it dissolves the starting raw materials to a certain extent and does not impede the reaction. Examples thereof may include halogenated hydrocarbon-based solvents such as methylene chloride, chloroform; ether-based solvents such as tetrahydrofuran, 1,4-dioxane; amide-based solvents such as N,N-dimethylformamide, N-methylpyrrolidinone; sulfoxide-based solvents such as dimethyl sulfoxide; ester-based solvents such as ethyl acetate; acetonitrile, and mixtures of these solvents. Examples of the condensation agent may include Bop (1H-1,2,3-benzotriazol-1-yloxy(tri(dimethylamino))phosphonium hexafluorophosphate), HATU (O-(7-azabenzotriazol-1-yl)-N,N,N',N'-tetramethyl-uronium hexafluorophosphate), WSC (1-ethyl-3-(3-dimethylaminopropyl)carbodiimide hydrochloride), DCC(N,N-dicyclohexylcarbodiimide), or the like. A catalytic amount of 4-dimethylaminopyridine can also be added to accelerate the reaction. This step can also be performed by adding from 1 to 3 equivalents of base such as triethylamine, N-methylmorpholine, or the like. Compound (1-1-2) can be used in an amount of from 1 equivalent to a solvent amount based on Compound (1-1-1), and preferably a solvent amount is used. The condensation agent can be used in an amount of from 1 to 3 equivalents, and preferably 1 to 1.5 equivalents, based on Compound (1-1-1). The reaction temperature is from 0° C. to the reflux temperature, and the reaction time is from 10 minutes to 48 hours.

[Step 1-2]

This step is a step wherein Compound (1-2) is obtained by deprotecting a benzyl group from Compound (1-1-3) with a palladium catalyst under a hydrogen atmosphere, and reacting the carboxylic acid thus obtained with Compound (1-1) in the presence of a condensation agent. There are no particular restrictions on the solvent used in the reaction for deprotecting the benzyl group, as long as it dissolves the starting raw materials to a certain extent and does not impede the reaction. Examples thereof may include ether-based solvents such as tetrahydrofuran, 1,4-dioxane; alcohol-based solvents such as methanol, ethanol; alcohol-based solvents such as ethyl acetate; and mixtures of these solvents. The palladium catalyst can be palladium-carbon, palladium hydroxide, or the like. There are no particular restrictions on the solvent used in the condensation reaction, as long as it dissolves the starting raw materials to a certain extent and does not impede the reaction. Examples thereof may include halogenated hydrocarbon-based solvents such as methylene chloride, chloroform; ether-based solvents such as tetrahydrofuran, 1,4-dioxane; amide-based solvents such as N,N-dimethylformamide, N-methylpyrrolidinone; sulfoxide-based solvents such as dimethyl sulfoxide; ester-based solvents such as ethyl acetate; acetonitrile, and mixtures of these solvents. Examples of the condensation agent may include Bop (1H-1,2,3-benzotriazol-1-yloxy(tri(dimethylamino))phosphonium hexafluorophosphate), HATU (O-(7-azabenzotriazol-1-yl)-N,N,N',N'-tetramethyl-uronium hexafluorophosphate), WSC (1-ethyl-3-(3-dimethylaminopropyl)carbodiimide hydrochloride), DCC(N,N-dicyclohexylcarbodiimide), or the like. A catalytic amount of 4-dimethylaminopyridine can also be added to accelerate the reaction. This step can also be performed by adding from 1 to 3 equivalents of base such as triethylamine, N-methylmorpholine, or the like. Compound (1-1-3) can be used in an amount of from 1 to 3 equivalents based on Compound (1-1). The palladium catalyst can be used based on Compound (1-1) in an amount of from 0.01 to 1 equivalent. The condensation agent can be used in an amount of from 1 to 3 equivalents based on Compound (1-1). The reaction temperature is from 0° C. to the reflux temperature, and the reaction time is from 10 minutes to 48 hours.

[Step 1-3]

This step is a step wherein Compound (1) is obtained by deprotecting the tert-butoxycarbonyl group of Compound (1-2) under acidic conditions. There are no particular restrictions on the solvent used in this reaction, as long as it dissolves the starting raw materials to a certain extent and does not impede the reaction. Examples thereof may include ether-based solvents such as 1,4-dioxane, tetrahydrofuran; aromatic hydrocarbon-based solvents such as benzene, toluene; alcohol-based solvents such as methanol, ethanol; methylene chloride, water, and mixtures of these solvents. The acid can be hydrochloric acid, sulfuric acid, hydrobromic acid, trifluoroacetic acid, formic acid, or the like. The acid is used in an amount of from 2 equivalents to a solvent amount based on Compound (1-2). The reaction temperature is from 0° C. to the reflux temerature, and the reaction time is from 10 minutes to 24 hours.

Manufacturing Method 2—Method for Manufacturing Compound (Ia)

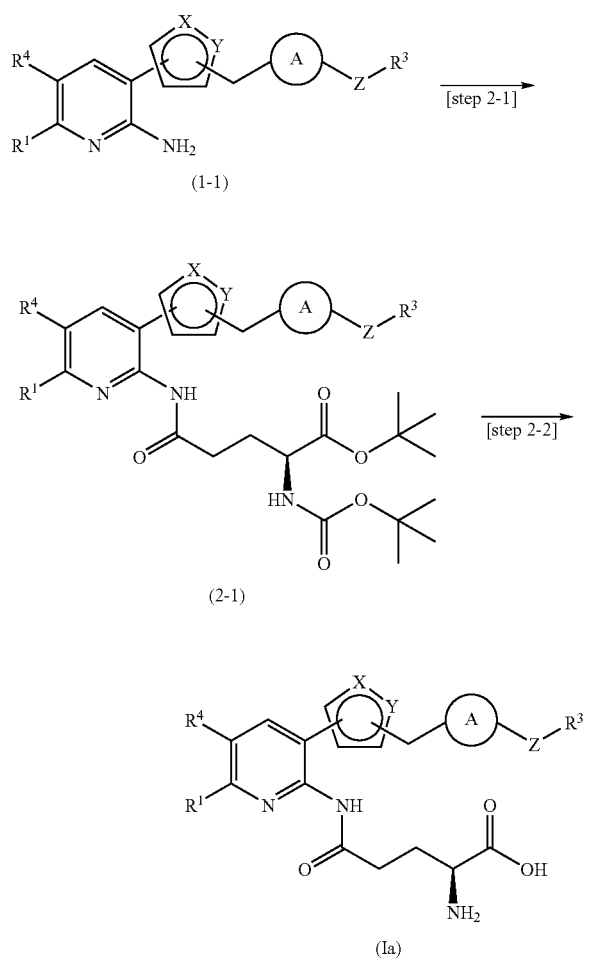

(wherein the ring A, $R^1$, $R^3$, $R^4$, X, Y, and Z are defined the same as above.)

[Step 2-1]

This step is a step wherein Compound (2-1) is obtained by reacting compound (1-1) with N-tert-butoxycarbonyl-L-glutamic acid 1-tert-butyl ester in the presence of a condensation agent. Compound (2-1) can be manufactured by the same method as in step 1-1.

[Step 2-2]

This step is a step wherein Compound (Ia) is obtained by deprotecting the two tert-butoxycarbonyl groups of Compound (2-1). Compound (Ia) can be manufactured by the same method as in step 1-3.

EXAMPLES

The compounds according to the present invention can be manufactured, for example, by the methods described in the following Examples, Reference Examples, and Manufacturing Examples. However, these are used for illustrative purposes, and the compounds according to the present invention are not in any case limited to the following specific Examples.

Reference Example 1

3-(3-(4-(Pyridin-2-yloxymethyl)-benzyl)-isoxazol-5-yl)-pyridin-2-ylamine

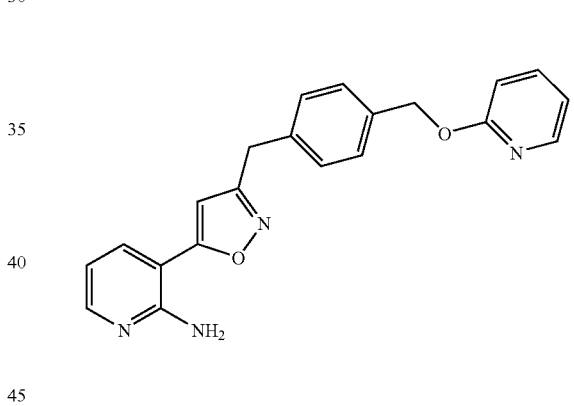

To a tetrahydrofuran solvent (5 mL) of (4-(pyridin-2-yloxymethyl)-phenyl)-acetohydroxymoyl chloride (510 mg, 1.84 mmol) described in Manufacturing Example 1-1-5 and 3-ethynyl-pyridin-2-ylamine (150 mg, 1.27 mmol) described in Manufacturing Example 1-2-3 of WO 07/05261570 was added triethylamine (8 µL, 5.08 mmol), which was stirred for 95 minutes at room temperature. To the reaction solution was added water at room temperature, which was extracted with ethyl acetate. The organic layer was washed with saturated saline, and was dried over anhydrous magnesium sulfate, and the solvent was then evaporated under a reduced pressure. The residue was purified by NH silica gel column chromatography (heptane:ethyl acetate=2:1) to obtain the titled compound (120 mg (26%)).

$^1$H-NMR spectrum (CDCl$_3$) δ (ppm): 4.08 (2H, s), 5.37 (2H, s), 6.33 (1H, s), 6.45 (2H, brs), 6.79-6.82 (2H, m), 6.88-6.91 (1H, m), 7.30 (2H, d, J=8.1 Hz), 7.45 (2H, d, J=8.1 Hz), 7.57-7.61 (1H, m), 7.85 (1H, d, J=7.3 Hz), 8.03 (1H, d, J=5.5 Hz), 8.17 (1H, m).

The starting material, (4-(pyridin-2-yloxymethyl)-phenyl)-acetohydroxymoyl chloride, was synthesized by the following method.

Manufacturing Example 1-1-1

(4-(Pyridin-2-yloxymethyl)-phenyl)-methanol

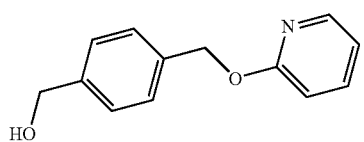

To a mixture of 1,4-benzenedimethanol (5.5 g, 40 mmol), 2-fluoropyridine (1.3 g, 13 mmol) and N,N-dimethylformamide (15 mL) was added sodium hydride (1.4 g, 40 mmol, 66% in oil) at 0° C., which was stirred for 20 minutes at room temperature and for 1 hour at 70° C. To the reaction mixture was added water, and extraction was performed with ethyl acetate. The organic layer was washed with saturated saline, and the solvent was evaporated under a reduced pressure. The residue was purified by NH silica gel column chromatography (ethyl acetate:heptane=1:1) to obtain the titled compound (1.9 g, 66%).

$^1$H-NMR spectrum (CDCl$_3$) δ (ppm): 4.71 (2H, s), 5.38 (2H, s), 6.81 (1H, td, J=0.9, 8.4 Hz), 6.89 (1H, ddd, J=0.9, 5.1, 7.1 Hz), 7.37-7.47 (4H, m), 7.59 (1H, ddd, J=2.0, 7.1, 8.3 Hz), 8.17 (1H, ddd, J=0.7, 2.0, 5.1 Hz).

Manufacturing Example 1-1-2

4-(Pyridin-2-yloxymethyl)-benzaldehyde

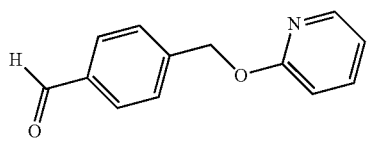

To a mixture of (4-(pyridin-2-yloxymethyl)-phenyl)-methanol (1.9 g, 8.6 mmol) described in Manufacturing Example 1-1-1 and methylene chloride (30 mL) was added manganese dioxide (15 g, 17 mmol) at room temperature, which was stirred overnight at this temperature. The reaction mixture was filtered through a Celite pad, and the solvent was evaporated under a reduced pressure. The residue was purified by silica gel column chromatography (ethyl acetate:heptane=1:4) to obtain the titled compound (770 mg, 42%).

$^1$H-NMR spectrum (CDCl$_3$) δ (ppm): 5.48 (2H, s), 6.85 (1H, d, J=8.2 Hz), 6.90-6.93 (1H, m), 7.60-7.64 (3H, m), 7.89 (2H, d, J=8.1 Hz), 8.16 (1H, dd, J=1.3, 4.9 Hz), 10.0 (1H, s).

Manufacturing Example 1-1-3

2-(4-((E)-2-Nitro-vinyl)-benzyloxy)-pyridine

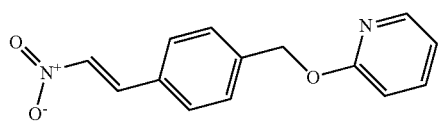

A mixture of 4-(pyridin-2-yloxymethyl)-benzaldehyde (23.4 g, 110 mmol) described in Manufacturing Example 1-1-2, nitromethane (33.6 g, 550 mmol), ammonium acetate (17.0 g, 220 mmol), and acetic acid (200 mL) was stirred for 1 hour and 45 minutes at 100° C. A small amount of water was added thereto while the reaction solution was stirred under ice cooling, and the precipitated solids were filtered, so as to obtain the titled compound (21.0 g, 74.5%).

$^1$H-NMR spectrum (DMSO-d$_6$) δ (ppm): 5.41 (2H, s), 6.91 (1H, dd, J=0.8, 8.4 Hz), 6.99-7.10 (1H, m), 7.53 (2H, d, J=8.0 Hz), 7.72-7.79 (1H, m), 7.86 (2H, d, J=8.0 Hz), 8.13 (1H, d, J=10 Hz), 8.15-8.20 (1H, m), 8.23 (1H, d, J=10 Hz).

Manufacturing Example 1-1-4

2-(4-(2-Nitro-ethyl)-benzyloxy)-pyridine

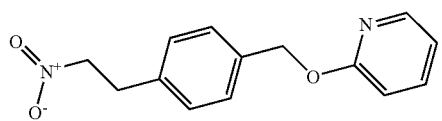

To a solution of 2-(4-((E)-2-nitro-vinyl)-benzyloxy)-pyridine (21.0 g, 81.9 mmol) described in Manufacturing Example 1-1-3, acetic acid (21 mL), and dimethyl sulfoxide (200 mL) was added sodium borohydride (4.96 g, 131 mmol) at room temperature and under suitable cooling. After the addition of sodium borohydride, the ice bath was removed and the reaction solution was stirred for 15 minutes at room temperature. The reaction solution was separated into water and ethyl acetate. The ethyl acetate layer was washed twice with water and once with saline, and was then dried over anhydrous magnesium sulfate and the solvent was evaporated under a reduced pressure. The residue was purified by NH silica gel column chromatography (ethyl acetate:heptane=1:3) to obtain the titled compound (16.3 g, 77.1%).

$^1$H-NMR spectrum (DMSO-d$_6$) δ (ppm): 3.23 (2H, t, J=6.8 Hz), 4.85 (2H, t, J=6.8 Hz), 5.32 (2H, s), 6.82-6.88 (1H, m), 6.96-7.01 (1H, m), 7.28 (2H, d, J=8.0 Hz), 7.38 (2H, d, J=8.0 Hz), 7.69-7.74 (1H, m), 8.15-8.19 (1H, m).

Manufacturing Example 1-1-5

4-(Pyridin-2-yloxymethyl)-phenyl-acetohydroxymoyl chloride

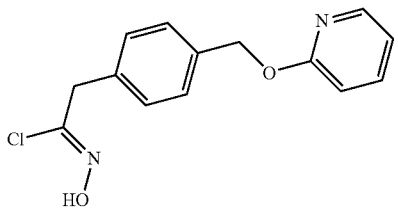

Lithium wire (323 mg, 46.6 mmol) was added to and dissolved in methanol (75 mL). To this solution was added 2-(4-(2-nitro-ethyl)-benzyloxy)-pyridine (6.0 g, 23.3 mmol) described in Manufacturing Example 1-1-4, and the reaction solution was concentrated under a reduced pressure. Toluene was added to the residue, and this solvent was concentrated under a reduced pressure. A solution of the resulting residue in methylene chloride (90 mL) and tetrahydrofuran (45 mL) was cooled to −78° C., and titanium(IV) chloride (8.15 mL, 74.4 mmol) was added thereto. As soon as the addition of the titanium(IV) chloride was complete, the reaction solution was stirred for 10 minutes, and then for 30 minutes at room temperature. The reaction solution was put into an ice water and extracted with ethyl acetate. The organic layer was dried over anhydrous magnesium sulfate, and the magnesium sulfate was filtered out. The filtrate was passed through a glass filter (eluted with ethyl acetate) spread with neutral silica gel. The eluate thus obtained was concentrated under a reduced pressure. A small amount of ethyl acetate was added to the residue, and the precipitated solids were filtered, so as to obtain the titled compound (1.86 g, 28.8%).

$^1$H-NMR spectrum (DMSO-$d_6$) δ (ppm): 3.82 (2H, s), 5.33 (2H, s), 6.84-6.89 (1H, m), 6.97-7.01 (1H, m), 7.25 (2H, d, J=8.4 Hz), 7.41 (2H, d, J=8.4 Hz), 7.70-7.76 (1H, m), 8.15-8.18 (1H, m), 11.7 (1H, s).

The titled compound of Manufacturing Example 1-1-5 can also be synthesized by another method.

Manufacturing Example 1-2-1

2-(4-Bromo-benzyloxy)pyridine

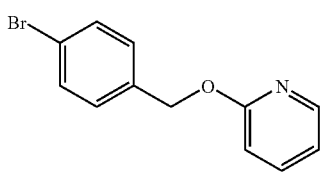

To a solution of 4-bromobenzyl alcohol (25 g, 130 mmol) in N,N-dimethylformamide (125 mL) was added potassium tert-butoxid at room temperature, which was stirred for 10 minutes at 54° C. To this reaction solution was added 2-fluoropyridine (15 mL, 154 mmol) at a temperature of from 40° C. to 58° C., which was stirred for another 30 minutes at 65° C. The reaction solution was cooled to room temperature, water and ethyl acetate were added to separate the reaction solution. The aqueous layer was further extracted (twice) with ethyl acetate. This was combined with an ethyl acetate layer, washed with water (three times) and saline (once), and was dried over anhydrous magnesium sulfate and filtered. The filtrate was concentrated under a reduced pressure. Diethyl ether was added to the residue, and this was concentrated under a reduced pressure, so as to obtain a crude product of the titled compound (34 g).

$^1$H-NMR spectrum (CDCl$_3$) δ (ppm): 5.33 (2H, s), 6.87-6.70 (1H, m), 8.15-8.18 (1H, m)

Manufacturing Example 1-2-2

4-(Pyridin-2-yloxymethyl)-benzaldehyde

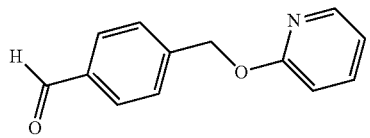

To a tetrahydrofuran solution (120 mL) of 2-(4-bromobenzyloxy)pyridine (34 g, 128 mmol) described in Manufacturing Example 1-2-1 was added n-butyl lithium (50 mL, 2.6 M, hexane solution, 134 mL) dropwise at −78° C. After stirring for 30 minutes, N,N-dimethylformamide (10 mL, 134 mmol) was added dropwise at −78° C. to the reaction solution, which was stirred at room temperature. Water and ethyl acetate were added to separate the reaction solution. The ethyl acetate layer was washed with water (twice) and saline (once). This was combined with the aqueous layer and extracted with ethyl acetate. The ethyl acetate layer thus obtained was washed with water (twice) and saline (once). The previously obtained ethyl acetate layer and the ethyl acetate layer obtained this time were combined, dried over anhydrous magnesium sulfate, and filtered. This filtrate was concentrated under a reduced pressure, so as to obtain a crude product of the titled compound (26.8 g).

Manufacturing Example 1-2-3

2-(4-((E)-2-Nitro-vinyl)-benzyloxy)-pyridine

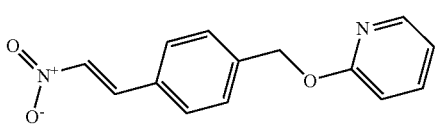

A mixture of 4-(pyridin-2-yloxymethyl)-benzaldehyde (26.8 g, 26 mmol) described in Manufacturing Example 1-2-2, nitromethane (34 mL, 630 mmol), ammonium acetate (19 g, 252 mmol), and acetic acid (90 mL) was stirred for 1 hour and 30 minutes at 100° C. Ethyl acetate and water were added to separate the reaction mixture. The organic layer was separated, washed with water (five times) and saturated sodium bicarbonate water (once), dried over anhydrous magnesium sulfate, and filtered. This filtrate was concentrated under a reduced pressure, so as to obtain a crude product of the titled compound (31 g).

Manufacturing Example 1-2-4

2-(4-(2-Nitro-ethyl)-benzyloxy)-pyridine

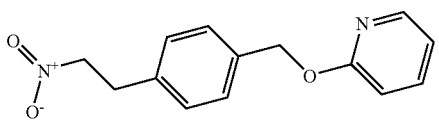

To a dimethyl sulfoxide solution (150 mL) of acetic acid (7.4 mL) and 2-(4-((E)-2-nitro-vinyl)-benzyloxy)-pyridine (30.8 g, 120 mmol) described in Manufacturing Example 1-2-3 was added sodium borohydride (2.45 g, 64.8 mmol) at 30° C. or lower.

The reaction solution was stirred for 40 minutes at room temperature. Water, ethyl acetate, and diethyl ether were added at 30° C. or lower to the reaction solution, to separate into water and an organic layer. The aqueous layer was extracted with ethyl acetate. The previously obtained organic layer and the ethyl acetate layer obtained this time were combined, washed with water (three times) and saline (once), dried over anhydrous magnesium sulfate, and filtered. This filtrate was concentrated under a reduced pressure. The residue was purified by NH silica gel column chromatography (ethyl acetate:heptane=1:4) to obtain the titled compound (15.2 g).

Manufacturing Example 1-2-5

4-(Pyridin-2-yloxymethyl)-phenyl-acetohydroxymoyl chloride

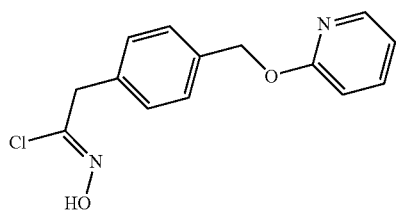

To a methanol solution (80 mL) of 2-(4-(2-nitro-ethyl)-benzyloxy)-pyridine (15.2 g, 59 mmol) described in Manufacturing Example 1-2-4 was added lithium methoxide (4.49 g, 118 mmol), which was stirred for 3 minutes. The reaction solution was concentrated under a reduced pressure. Toluene was added to the residue, and the solvent was concentrated under a reduced pressure. A methylene chloride (100 mL) and tetrahydrofuran (50 mL) solution of the residue thus obtained was cooled to −66° C., and titanium(IV) chloride (20.8 mL, 189 mmol) was added thereto under stirring. The reaction solution was stirred for 10 minutes at 0° C., and then stirred for 30 minutes at room temperature. The reaction solution was poured into ice water and stirred for 30 minutes at room temperature. Ethyl acetate and diethyl ether were added to partition the reaction solution. The organic layer was washed with water (three times) and saline (once). The aqueous layer was combined with this, and extraction was performed with ethyl acetate (twice). This was combined with the ethyl acetate layer and washed with water (three times) and saline ((once). The previously obtained organic layer and the ethyl acetate layer obtained this time were combined, dried over anhydrous magnesium sulfate and sodium sulfate, and filtered. This filtrate was concentrated under a reduced pressure, so as to obtain a crude product of the titled compound (11.5 g).

The titled compound of Reference Example 1 can also be synthesized by the following other methods 1 to 3.

The title compound of Reference Example 2 can also be synthesized by the following alternative methods 1 to 3.

Alternative Method 1 for Reference Example 1

3-(3-(4-(Pyridin-2-yloxymethyl)-benzyl)-isoxazol-5-yl)-pyridin-2-ylamine

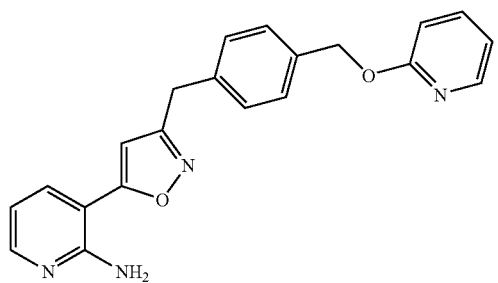

To a mixture of zinc chloride (8.82 g) and tetrahydrofuran (130 mL) were added 3-ethynyl-pyridin-2-ylamine (3.00 g, purity 98%) described in Manufacturing Example 1-2-3 of WO 07/052,615 and the 4-(pyridin-2-yloxymethyl)-phenyl-acetohydroxymoyl chloride (17.4 g, purity 94%) described in Manufacturing Example 1-2-5 at 0° C. The reaction mixture was cooled to room temperature, and triethylamine (9.02 mL) was added dropwise with an internal temperature maintained at 28° C. or less on a water bath. The reaction mixture was stirred at room temperature for 20 minutes, and then at 35° C. for 1 hour. The reaction mixture was cooled to room temperature and added ammonium chloride aqueous solution and ethyl acetate, then added aqueous ammonia solution up to about pH 8. The organic layer was separated and washed with saturated aqueous sodium chloride and dried over anhydrous magnesium sulfate, and the solvent was evaporated under a reduced pressure. The residue was purified by NH silica gel column chromatography (heptane:ethyl acetate=3:2) and then crystallized with a mixed solvent of tert-butylmethyl ether and heptane to obtain the title compound (5.32 g).

$^1$H-NMR Spectrum (CDCl$_3$) δ (ppm): 4.07 (2H, s), 5.37 (4H, brs), 6.25 (1H, s), 6.71 (1H, dd, J=4.8, 7.7 Hz), 6.79-6.81 (1H, m), 6.89 (1H, ddd, J=0.8, 5.0, 7.0 Hz), 7.30 (2H, d, J=7.9 Hz), 7.44 (2H, d, J=8.1 Hz), 7.58 (1H, ddd, J=2.0, 7.1, 8.4 Hz), 7.70 (1H, dd, J=1.8, 7.7 Hz), 8.14 (1H, dd, J=1.8, 4.9 Hz), 8.17-8.18 (1H, m).

In Alternative Method 1 for Reference Example 1, the starting material 4-(pyridin-2-yloxymethyl)-phenyl-acetohydroxymoyl chloride was synthesized as follows.

Manufacturing Example 1-3-1

Methyl 3-(4-(pyridin-2-yloxymethyl)-phenyl)-oxyran-2-carboxylate

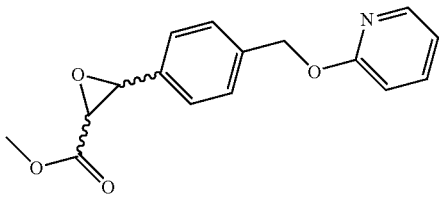

To a mixture of 4-(pyridin-2-yloxymethyl)-benzaldehyde (24.8 g) described in Manufacturing Example 1-1-2 and tetrahydrofuran (160 mL) was added methyl chloroacetate (10.2 mL) at −15° C., and sodium methoxide (23.7 mL, 28% methanol solution) was then added at the same temperature. The reaction mixture was stirred at 0° C. for 1 hour, and then at room temperature for 2 hours. The reaction mixture was added to ice water (800 mL) containing acetic acid (6 mL), and warmed to room temperature. Ethyl acetate was added to extract the reaction mixture, and the organic layer was then separated, washed with saturated aqueous sodium chloride and dried over anhydrous magnesium sulfate. The solvent was evaporated under a reduced pressure to obtain the title compound (30.2 g).

$^1$H-NMR Spectrum (CDCl$_3$) δ (ppm): 3.51 (1H, d, J=1.8 Hz), 3.83 (3H, s), 4.11 (1H, d, J=1.8 Hz), 5.38 (2H, s), 6.81 (1H, td, J=0.9, 8.4 Hz), 6.89 (1H, ddd, J=0.9, 5.1, 7.1 Hz), 7.29-7.31 (2H, m), 7.47 (2H, d, J=8.2 Hz), 7.59 (1H, ddd, J=2.0, 7.1, 8.4 Hz), 8.17 (1H, ddd, J=0.8, 2.0, 5.1 Hz).

Manufacturing Example 1-3-2

Sodium 3-(4-(pyridin-2-yloxymethyl)-phenyl)-oxyran-2-carboxylate

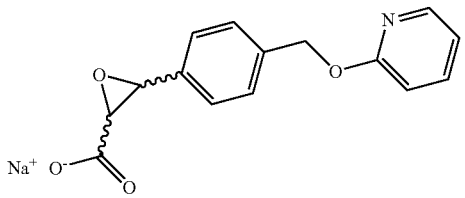

To a mixture of ethanol (300 mL) and methyl 3-(4-(pyridin-2-yloxymethyl)-phenyl)-oxyran-2-carboxylate (19.9 g) described in Manufacturing Example 1-3-1 were added sodium methoxide (14.2 mL, 28% methanol solution), water (1.3 mL) and tetrahydrofuran (100 mL) successively at 0° C., which was stirred at room temperature for 1 hour. Diethyl ether (200 mL) was added to the reaction mixture, and the precipitated solids were filtered to obtain the title compound (14.3 g).

$^1$H-NMR Spectrum (CD$_3$OD) δ (ppm): 3.31 (1H, d, J=1.8 Hz), 3.88 (1H, d, J=1.8 Hz), 5.33 (2H, s), 6.84 (1H, td, J=0.9, 8.2 Hz), 6.94 (1H, ddd, J=0.9, 5.1, 7.1 Hz), 7.29-7.31 (2H, m), 7.42 (2H, d, J=8.2 Hz), 7.68 (1H, ddd, J=2.0, 7.1, 8.4 Hz), 8.12 (1H, ddd, J=0.7, 2.0, 5.1 Hz).

Manufacturing Example 1-3-3

4-(Pyridin-2-yloxymethyl)-phenyl-acetaldehyde

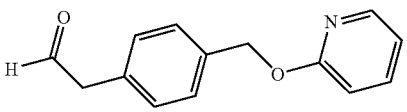

A mixture of sodium 3-(4-(pyridin-2-yloxymethyl)-phenyl)-oxyran-2-carboxylate described in Manufacturing Example 1-3-2 (9.95 g), toluene (200 mL), water (120 mL) and acetic acid (16 mL) was stirred for 90 minutes at 73° C. The reaction mixture was cooled to room temperature, ethyl acetate was added to extract the reaction mixture, and the organic layer was separated, washed with saturated aqueous sodium chloride and dried over anhydrous magnesium sulfate. The solvent was evaporated under a reduced pressure to obtain the title compound (6.82 g).

$^1$H-NMR Spectrum (CDCl$_3$) δ (ppm): 3.70 (2H, d, J=2.2 Hz), 5.38 (2H, s), 6.81 (1H, td, J=0.8, 8.2 Hz), 6.89 (1H, ddd, J=0.9, 5.1, 7.1 Hz), 7.24 (2H, d, J=8.1), 7.48 (2H, d, J=8.1 Hz), 7.59 (1H, ddd, J=2.0, 7.1, 8.4 Hz), 8.18 (1H, ddd, J=0.6, 2.0, 5.0 Hz), 9.75 (1H, t, J=2.4).

Manufacturing Example 1-3-4

4-(Pyridin-2-yloxymethyl)-phenyl-acetaldehyde oxime (E/Z mixture)

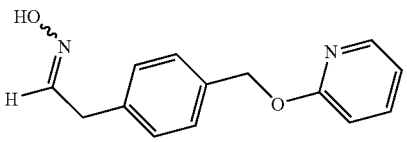

To a mixture of hydroxylamine sulfate (19.7 g) and water (250 mL) was added 1N aqueous sodium hydroxide (240 mL) at 0° C., which was stirred at the same temperature for 15 minutes. To the reaction mixture was then added dropwise a mixture of 4-(pyridin-2-yloxymethyl)-phenyl-acetaldehyde described in Manufacturing Example 1-3-3 (27.3 g) and methanol (250 mL), which was stirred overnight at room temperature. The precipitated solids were filtered to obtain the title compound (20.3 g) as an E/Z mixture.

$^1$H-NMR Spectrum (CDCl$_3$) δ (ppm): 3.54 (2H, d, J=6.2 Hz), 3.74 (2H, d, J=5.3 Hz), 5.36 (2H+2H, s), 6.79-6.81 (1H+1H, m), 6.87-6.90 (1H+2H, m), 7.22-7.24 (2H+2H, m), 7.42-7.44 (2H+2H, m), 7.53 (1H, t, J=6.3 Hz), 7.56-7.61 ( 1H+1H, m), 8.17-8.18 (1H+1H, m) (underbar=E or Z).

Manufacturing Example 1-3-5

4-(Pyridin-2-yloxymethyl)-phenyl-acetohydroxymoyl chloride

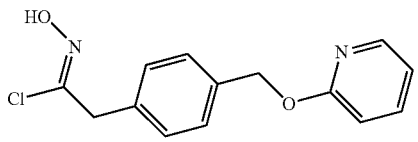

To a mixture of 4-(pyridin-2-yloxymethyl)-phenyl-acetaldehyde oxime (E/Z mixture) described in Manufacturing Example 1-3-4 (132 mg) and N,N-dimethylformamide (2 mL) was added N-chlorosuccinimide (72.8 mg) at room temperature. Hydrochloric acid gas was blown at the same temperature into the reaction mixture, which was then stirred at the same temperature for 90 minutes. Ethyl acetate and water were added to extract the reaction mixture, and the organic layer was separated, washed with saturated aqueous sodium chloride, and dried over anhydrous magnesium sulfate. The solvent was evaporated under a reduced pressure, and the resulting residue was washed with a mixed diethyl ether and heptane solvent to obtain the title compound (123 mg).
$^1$H-NMR Spectrum (CDCl$_3$) δ (ppm): 3.81 (2H, s), 5.36 (2H, s), 6.81 (1H, d, J=8.2 Hz), 6.88-6.91 (1H, m), 7.28 (2H, d, J=8.1), 7.43 (2H, d, J=8.1 Hz), 7.57-7.62 (1H, m), 8.17-8.19 (1H, m).

Alternative Method 2 for Reference Example 1

3-(3-(4-(Pyridin-2-yloxymethyl)-benzyl)-isoxazol-5-yl)-pyridin-2-ylamine

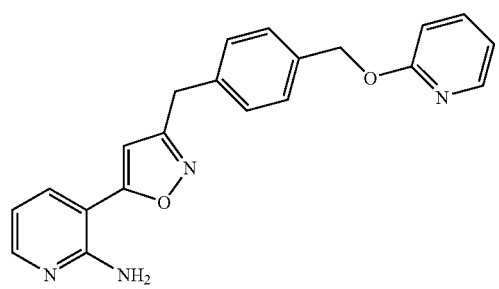

To a dichloromethane (120 mL) solution of di-tert-butyl (3-(3-(4-((pyridin-2-yloxy)methyl)benzyl)isoxazol-5-yl)pyridin-2-yl)imidodicarbonate (11.8 g, purity about 70%) described in Manufacturing Example 1-4-2 was added trifluoroacetic acid (40 mL) at 0° C., which was stirred at room temperature for 14 hours. To the reaction mixture was added saturated aqueous sodium bicarbonate at 20° C. or less, which was then extracted with ethyl acetate and purified by NH silica gel column chromatography (heptane:ethyl acetate=1:1). The solvent was concentrated under a reduced pressure, tert-butylmethyl ether was added to the resulting residue, and the solids were filtered to obtain the title compound (7.29 g).

$^1$H-NMR Spectrum (DMSO-d6) δ (ppm): 4.04 (2H, s), 5.32 (2H, s), 6.26 (2H, brs), 6.69 (1H, dd, J=4.8, 8.0 Hz), 6.81 (1H, s), 6.83-6.87 (1H, m), 6.97-7.00 (1H, m), 7.33 (2H, d, J=8.0 Hz), 7.40 (2H, d, J=8.0 Hz), 7.69-7.74 (1H, m), 7.87 (1H, dd, J=2.0, 7.6 Hz), 8.08 (1H, dd, J=2.0, 7.6 Hz), 8.15-8.17 (1H, m).

The starting material di-tert-butyl (3-(3-(4-((pyridin-2-yloxy)methyl)benzyl)isoxazol-5-yl)pyridin-2-yl)imidodicarbonate was synthesized as follows.

Manufacturing Example 1-4-1

Di-tert-butyl (3-ethynylpyridin-2-yl)imidodicarbonate

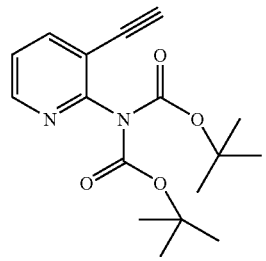

3-Ethynyl-pyridin-2-ylamine (6.34 g) described in Manufacturing Example 1-2-3 of WO 07/052,615, di-tert-butyl dicarbonate (58.5 g), triethylamine (27.1 g), 4-dimethylaminopyridine (655 mg) and tetrahydrofuran (254 mL) were stirred at room temperature for 18 hours. Silica gel was added to the reaction solution, and the solvent was concentrated under a reduced pressure. The resulting silica gel was purified by silica gel chromatography (heptane:ethyl acetate=3:1) to obtain the title compound (15 g) as a white solid.
$^1$H-NMR Spectrum (DMSO-d6) δ (ppm): 1.32 (18H, s), 4.59 (1H, s), 7.39-7.44 (1H, m), 7.99-8.03 (1H, m), 8.46-8.48 (1H, m).

Manufacturing Example 1-4-2

Di-tert-butyl (3-(3-(4-((pyridin-2-yloxy)methyl)benzyl)isoxazol-5-yl)pyridin-2-yl)imidodicarbonate

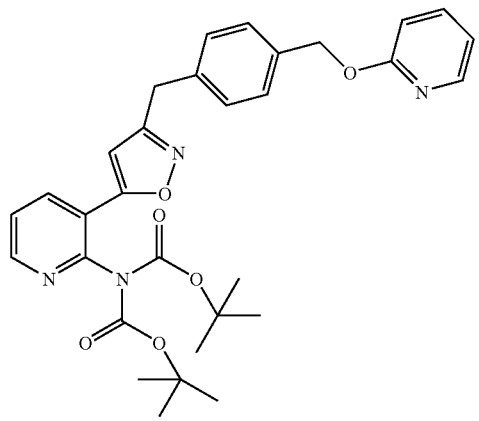

To a solution of di-tert-butyl (3-ethynylpyridin-2-yl)imidodicarbonate (12 g) described in Manufacturing Example 1-4-1,2-(4-(2-nitro-ethyl)-benzyloxy)pyridine (19.4 g) described in Manufacturing Example 1-1-4,4-dimethylaminopyridine (230 mg) and tetrahydrofuran (200 mL) was added di-tert-butyl dicarbonate (28.8 g) in 4 portions over the course of 8 hours at room temperature with stirring. After addition was complete, this was stirred at room temperature for a further 22 hours. Silica gel was added to the reaction solution, and the solvent was concentrated under a reduced pressure. The resulting silica gel was purified by silica gel chromatography (heptane:ethyl acetate=3:1 then 2:1) to obtain an oily product (11.8 g, containing about 70% of title compound) containing the title compound.

Di-tert-butyl (3-(3-(4-((pyridin-2-yloxy)methyl)benzyl) isoxazol-5-yl)pyridin-2-yl)imidodicarbonate described in Manufacturing Example 1-4-2 can also be synthesized by the following Alternative Methods 1 and 2.

Manufacturing Example 1-5-1

Di-tert-butyl (3-(3-(4-((pyridin-2-yloxy)methyl)benzyl)isoxazol-5-yl)pyridin-2-yl)imidodicarbonate (Alternative Method 1 for Manufacturing Example 1-4-2)

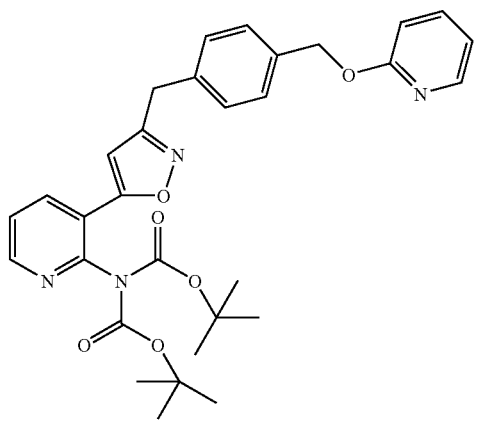

To a solution of di-tert-butyl(3-ethynylpyridin-2-yl)imidodicarbonate (2.0 g) described in Manufacturing Example 1-4-1,2-(4-(2-nitro-ethyl)-benzyloxy)pyridine (2.44 g) described in Manufacturing Example 1-1-4, triethylamine (0.086 uL) and tetrahydrofuran (20 mL) was added phenyl isocyanate (2.8 mL) in 4 portions over the course of 5.5 hours at 50° C. with stirring. After addition was complete, this mixture was stirred at 50° C. for a further 2 hours. NH-silica gel was added to the reaction solution, and the solvent was concentrated under a reduced pressure. The crude product adsorbed on NH-silica gel was purified by NH-silica gel chromatography (heptane:ethyl acetate=3:1). The resulting solution was concentrated under a reduced pressure, and purified by silica gel chromatography (heptane:ethyl acetate=3:1 then 2:1) to obtain the title compound (2.2 g).

$^1$H-NMR Spectrum (DMSO-d6) δ (ppm): 1.18 (18H, s), 4.07 (2H, s), 5.32 (2H, s), 6.58 (1H, s), 6.83-6.86 (1H, m), 6.96-7.01 (1H, m), 7.29 (2H, d, J=8.0 Hz), 7.40 (2H, d, J=8.0 Hz), 7.58 (1H, dd, J=4.8, 7.6 Hz), 7.69-7.74 (1H, m), 8.15-8.18 (1H, m), 8.34 (1H, dd, J=2.0, 7.6 Hz), 8.59 (1H, dd, J=2.0, 5.2 Hz).

Manufacturing Example 1-6-1

Di-tert-butyl (3-(3-(4-((pyridin-2-yloxy)methyl)benzyl)isoxazol-5-yl)pyridin-2-yl)imidodicarbonate (Alternative Method 2 for Manufacturing Example 1-4-2)

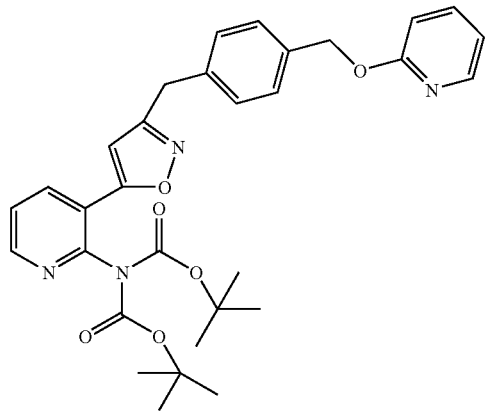

4-Methylene-2-oxo-4H-pyrido[2,3-d][1,3]oxazine-1-carboxylic acid tert-butyl ester (1.48 g) described in Manufacturing Example 1-6-2,2-(4-(2-nitro-ethyl)-benzyloxy)pyridine (2.9 g) described in Manufacturing Example 1-1-4, di-tert-butyl dicarbonate (6.14 g), 4-dimethylaminopyridine (68.6 mg) and tetrahydrofuran (60 mL) were stirred at room temperature for 2 hours. Silica gel was added to the reaction solution, and the solvent was concentrated under a reduced pressure. The crude product adsorbed on silica gel was purified by silica gel chromatography (heptane:ethyl acetate=3:1 then 1:1 then 1:2) to obtain the title compound (2.1 g).

$^1$H-NMR Spectrum (DMSO-d6) δ (ppm): 1.18 (18H, s), 4.07 (2H, s), 5.32 (2H, s), 6.58 (1H, s), 6.83-6.86 (1H, m), 6.96-7.01 (1H, m), 7.29 (2H, d, J=8.0 Hz), 7.40 (2H, d, J=8.0 Hz), 7.58 (1H, dd, J=4.8, 7.6 Hz), 7.69-7.74 (1H, m), 8.15-8.18 (1H, m), 8.34 (1H, dd, J=2.0, 7.6 Hz), 8.59 (1H, dd, J=2.0, 5.2 Hz).

The starting material 4-methylene-2-oxo-4H-pyrido[2,3-d][1,3]oxazine-1-carboxylic acid tert-butyl ester was synthesized as follows.

Manufacturing Example 1-6-2

4-Methylene-2-oxo-4H-pyrido[2,3-d][1,3]oxazine-1-carboxylic acid tert-butyl ester

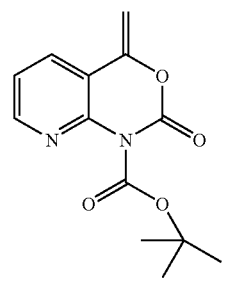

1-(2-Amino-pyridin-3-yl)-ethanone (990 mg), di-tert-butyl dicarbonate (7.92 g), 4-dimethylaminopyridine (88.8 mg), triethylamine (4.95 mL) and tetrahydrofuran (16.5 mL) were stirred at room temperature for 24 hours. Silica gel was added to the reaction solution, and the solvent was concentrated under a reduced pressure. The crude product adsorbed on silica gel was purified by silica gel chromatography (heptane: ethyl acetate=2:1) to obtain the title compound (1.48 g).

¹H-NMR Spectrum (DMSO-d6) δ (ppm): 1.56 (9H, s), 5.01 (1H, d, J=3.6 Hz), 5.45 (1H, d, J=3.6 Hz), 7.28 (1H, dd, J=4.8, 8.0 Hz), 8.25 (1H, dd, J=1.6, 8.0 Hz), 8.36 (1H, dd, J=1.6, 4.8 Hz).

Alternative Method 3 for Reference Example 1

3-(3-(4-(Pyridin-2-yloxymethyl)-benzyl)-isoxazol-5-yl)-pyridin-2-ylamine

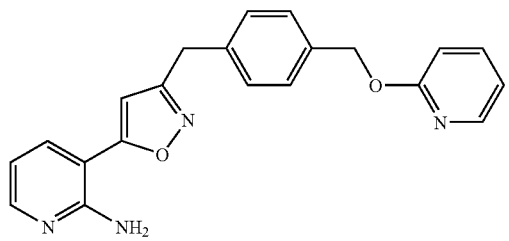

Under a nitrogen atmosphere, a mixture of 2-(4-(5-iodo-isoxazol-3-ylmethyl)-benzyloxy)-pyridine (200 mg) described in Manufacturing Example 1-8-2,2-tert-butoxycarbonylamino-3-pyridineboronic acid (134 mg) described in Manufacturing Example 1-7-2, sodium carbonate (82 mg), tetrakis(triphenylphosphine) palladium (59 mg), 1,2-dimethoxyethane (6 mL) and water (1 mL) was stirred at 80° C. for 2 hours. The mixture was cooled to room temperature, and ethyl acetate and water were added thereto. The organic layer was isolated, washed with water and saturated aqueous sodium chloride, dried over anhydrous magnesium sulfate, and then filtered. The filtrate was adsorbed on silica gel, and purified by silica gel column chromatography (heptane:ethyl acetate=4:1 then 1:1 then ethyl acetate) to obtain the title compound (116 mg).

The starting material 2-tert-butoxycarbonylamino-3-pyridineboronic acid was synthesized as follows.

Manufacturing Example 1-7-1

Pyridin-2-yl-carbamic acid tert-butyl ester

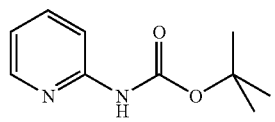

To a solution of tert-butyl alcohol (650 mL) and di-tert-butylcarbonate (24 g) was added 2-aminopyridine (9.4 g) slowly. This mixture was stirred at room temperature for 24 hours. The reaction solution was concentrated under a reduced pressure, and the residue was purified by silica gel column chromatography (heptane:ethyl acetate=1:1) to obtain the title compound (18 g).

¹H-NMR Spectrum (DMSO-d₆) δ (ppm): 1.47 (9H, s), 6.99-7.03 (1H, m), 7.70-7.74 (1H, m), 7.77-7.80 (1H, m), 8.23-8.24 (1H, m), 9.72 (1H, brs).

Manufacturing Example 1-7-2

2-tert-butoxycarbonylamino-3-pyridineboronic acid

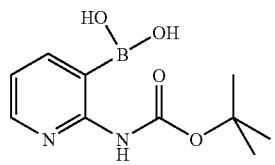

A solution of tetrahydrofuran (400 mL) of pyridin-2-yl-carbamic acid tert-butyl ester (16 g) described in Manufacturing Example 1-7-1 and N,N,N',N'-tetramethylethylene diamine (25 g) was cooled to −70° C., n-butyl lithium (78 mL, 2.64 M heptane solution) was added dropwise for 1 hour, and the mixture was stirred for 10 minutes. This mixture was then warmed to between −10° C. and −6° C., and stirred at that temperature for 2 hours. The solution was then cooled again to −70° C., and triisobutyl borate (58 g) was added dropwise for 1 hour. The mixture was warmed to 0° C., and saturated aqueous ammonium chloride solution was added thereto. To the resulting yellow solids was added ether and then stirred, and the solids were filtered and washed with ether and water. The solids were dried under a reduced pressure to obtain the title compound (14 g).

¹H-NMR Spectrum (DMSO-d₆) δ (ppm): 1.32-1.41 (9H, m), 6.80-6.84 (1H, m), 7.95-7.8.13 (2H, m).

The starting material 2-(4-(5-iodo-isoxazol-3-ylmethyl)-benzyloxy)-pyridine in Alternative Method 3 for Reference Example 1 was synthesized as follows.

Manufacturing Example 1-8-1

2-(4-(5-Tributylstannyl-isoxazol-3-ylmethyl)-benzyloxy)-pyridine

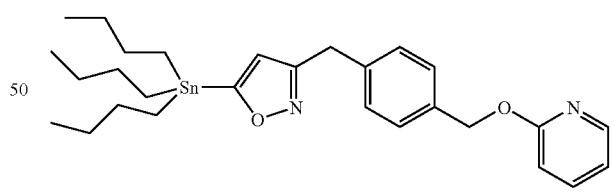

To a tetrahydrofuran solution (90 mL) of tri-n-butylethynyl tin (3 g), the 2-(4-(2-nitro-ethyl)-benzyloxy)-pyridine (4.9 g) described in Manufacturing Example 1-1-4 and 4-dimethylaminopyridine (116 mg) was added a tetrahydrofuran solution (30 mL) of di-tert-butyl dicarbonate (7.3 g), which was stirred at room temperature for 15 hours. Ethyl acetate and water were added to the mixture. The organic layer was isolated, washed with water and saturated aqueous sodium chloride, dried over anhydrous magnesium sulfate, and then filtered. The filtrate was adsorbed on silica gel, and purified by silica gel column chromatography (heptane:ethyl acetate=4:1) to obtain the title compound (5.3 g).

¹H-NMR Spectrum (DMSO-d₆) δ (ppm): 0.81-0.85 (9H, m), 1.08-1.12 (6H, m), 1.23-1.30 (6H, m), 1.46-1.54 (6H, m), 4.00 (2H, s), 5.30 (2H, s), 6.40 (1H, s), 6.83-6.86 (1H, m), 6.97-7.00 (1H, m), 7.25-7.26 (2H, m), 7.36-7.38 (2H, m), 7.69-7.74 (1H, m), 8.15-8.17 (1H, m).

Manufacturing Example 1-8-2

2-(4-(5-Iodo-isoxazol-3-ylmethyl)-benzyloxy)-pyridine

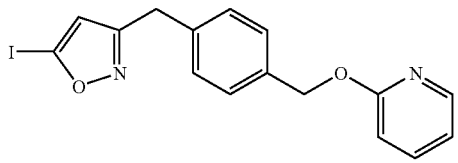

To a tetrahydrofuran solution (15 mL) of 2-(4-(5-tributyl-stannyl-isoxazol-3-ylmethyl)-benzyloxy)-pyridine (5.1 g) described in Manufacturing Example 1-8-1 was added iodine (2.5 g) at 0° C. This mixture was stirred at that temperature for 20 minutes. To the mixture were then added 10% sodium thiosulfate aqueous solution and ethyl acetate. The organic layer was isolated, washed with saturated aqueous sodium chloride, dried over anhydrous magnesium sulfate, and then filtered. The filtrate was concentrated, and the residue was purified by silica gel column chromatography (heptane:ethyl acetate=10:1 to 4:1) to obtain the title compound (2.4 g).

¹H-NMR Spectrum (DMSO-d₆) δ (ppm): 3.99 (2H, s), 5.31 (2H, s), 6.66 (1H, s), 6.84-6.87 (1H, m), 6.97-7.00 (1H, m), 7.26 (2H, d, J=8 Hz), 7.39 (2H, d, J=8 Hz), 7.70-7.74 (1H, m), 8.16-8.17 (1H, m).

Another method for the manufacturing example of 3-(3-(4-(pyridin-2-yloxymethyl)-benzyl)-isoxazol-5-yl)-pyridin-2-ylamine described in Reference Example 1 will now be described.

Reference Example 2

Synthesis of tert-butyl (3-acetylpyridin-2-yl)carbamate

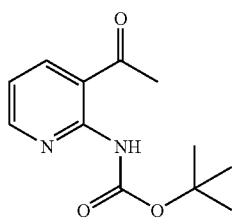

A mixture of 1-(2-aminopyridin-3-yl)ethanone (50 g, 368 mmol), di-tert-butyldicarbonate (120 g, 552 mmol) and tert-butanol (200 mL) was stirred at 90° C. for three hours under a nitrogen atmosphere. After cooling, the solvent was evaporated under a reduced pressure, n-heptane (500 mL) was added to the residue and the precipitated solid was filtered to obtain the title compound (77 g) as a yellow solid.

¹H-NMR Spectrum (CDCl₃) δ (ppm): 1.54 (9H, s), 2.64 (3H, s), 7.03 (1H, dd, J=4.8, 8.0 Hz), 8.16 (1H, dd, J=2.0, 8.0 Hz), 8.63 (1H, dd, J=2.0, 4.8 Hz), 10.82 (1H, brs).

Reference Example 3

Synthesis of ethyl 5-(2-aminopyridin-3-yl)isoxazol-3-carboxylate

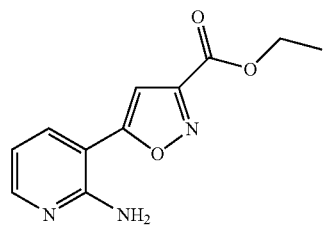

To a solution of tert-butyl (3-acetyl pyridin-2-yl)carbamate (600 mg, 2.29 mmol) and diethyl oxalate (669 mg, 4.58 mmol) in toluene (5.0 mL) was added potassium tert-butoxide (514 mg, 4.58 mmol) at room temperature under a nitrogen atmosphere, which was stirred for two hours. After addition of toluene (5.0 mL) and stirring for one hour, potassium tert-butoxide (257 mg, 2.29 mmol) was added thereto and the solution was stirred for two hours. To the reaction mixture were added hydroxylamine hydrochloride (477 mg, 6.87 mmol) and ethanol (10 mL), which was stirred for one hour, water (1.0 mL) was added thereto and the solution was stirred overnight at room temperature. Water (30 mL) was added thereto and the solution was extracted with ethyl acetate. After the organic layer was washed with saturated sodium chloride water and dried over anhydrous magnesium sulfate, the solution was concentrated. The concentrated residue was dissolved in N,N-dimethyl formamide (5 mL), triethylamine (192 mg) was added thereto, and the solution was stirred at 80° C. for six hours. After cooling, water was added thereto, and the solution was extracted with ethyl acetate. After the organic layer was washed with saturated sodium chloride water and dried over anhydrous magnesium sulfate, the solvent was evaporated under a reduced pressure to obtain the title compound (443 mg) as a white solid.

¹H-NMR Spectrum (CDCl₃) δ (ppm): 1.45 (3H, t, J=7.2 Hz), 4.49 (2H, q, J=7.2 Hz), 5.40 (2H, brs), 6.79 (1H, dd, J=5.2, 7.6 Hz), 6.91 (1H, s), 7.81 (1H, dd, J=2.0, 7.6 Hz), 8.21 (1H, dd, J=2.0, 5.2 Hz).

Reference Example 4

Synthesis of [5-(2-aminopyridin-3-yl)isoxazol-3-yl]methanol

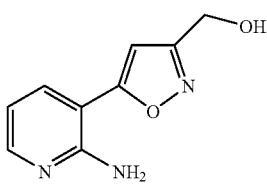

To a suspension of ethyl 5-(2-aminopyridin-3-yl)isoxazol-3-carboxylate (381 mg, 1.63 mmol) in tetrahydrofuran (3.8 mL) and ethanol (3.8 mL) was added sodium borohydride (201 mg, 4.89 mmol) at 0° C. under a nitrogen atmosphere, which was stirred at 0° C. for one hour and at 20° C. for 21 hours. Under an ice water bath cooling, to the reaction mixture was added 2N hydrochloric acid (2.46 mL, 4.89 mmol) dropwise, which was stirred at 0° C. for 10 minutes and at room temperature for 30 minutes. Under the ice water bath cooling, after an aqueous solution of 5% sodium bicarbonate was added dropwise to adjust basic, the solution was extracted with ethyl acetate. After the organic layer was dried over anhydrous magnesium sulfate, the solvent was evaporated under a reduced pressure. The residue was suspended in tetrahydrofuran (1.4 mL), to the reaction mixture was added sodium borohydride (67 mg, 1.63 mmol) at 0° C., which was washed thereto down with methanol (1.4 mL). After stirring at room temperature for one hour, the solution was stirred at 60° C. for five hours. Under an ice water bath cooling, to the reaction mixture was added 1N hydrochloric acid (1.63 mL, 1.63 mmol) dropwise, which was stirred at 0° C. for 10 minutes and at room temperature for 30 minutes. Under the ice water bath cooling, after adding 1N aqueous sodium hydroxide dropwise to adjust basic, the solution was extracted with ethyl acetate. After the organic layer was dried over anhydrous magnesium sulfate, the solvent was evaporated under a reduced pressure to obtain the title compound (258 mg) as a pale yellow solid.

$^1$H-NMR Spectrum (DMSO-$d_6$) δ (ppm): 4.56 (2H, d, J=5.6 Hz), 5.54 (1H, t, J=5.6 Hz), 6.27 (2H, brs), 6.72 (1H, dd, J=4.8, 7.6 Hz), 6.90 (1H, s), 7.90 (1H, dd, J=2.0, 7.6 Hz), 8.10 (1H, dd, J=2.0, 4.8 Hz).

Reference Examples 5 to 10 are other synthesis methods to Reference Examples 3 and 4.

Reference Example 5

Synthesis of N-(3-acetylpyridin-2-yl)-2,2-dimethylpropanamide

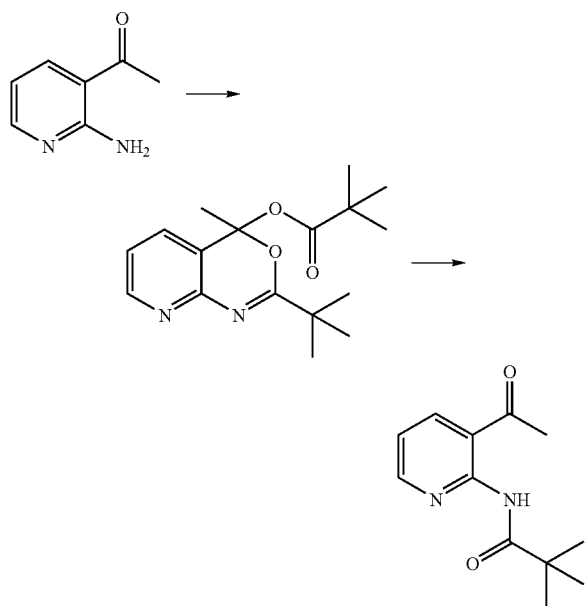

To a mixture of 1-(2-aminopyridin-3-yl)ethanone (272 mg, 2 mmol), 4-dimethylaminopyridine (24 mg, 0.2 mmol), triethylamine (0.64 mL, 4.6 mmol) and toluene (2 mL) was added pivaloyl chloride (0.52 mL, 4.2 mmol) dropwise at room temperature, which was stirred at room temperature for one hour and at 60° C. for five hours. After formation of 2-tert-butyl-4-methyl-4H-pyrido[2,3-d][1,3]oxazin-4-yl pivalate was confirmed, to the reaction mixture were added water (2 mL) and 5N hydrochloric acid (0.8 mL), which was stirred at room temperature for 30 minutes. After the reaction mixture was separated, to the aqueous layer was added 5N aqueous sodium hydroxide (1 mL) and extracted with toluene. The solvent was evaporated under a reduced pressure and the precipitated solid was filtered to obtain the title compound (415 mg).

$^1$H-NMR Spectrum (CDCl$_3$) δ (ppm): 1.33 (9H, s), 2.64 (3H, s), 7.10 (1H, dd, J=4.8, 8.0 Hz), 8.17 (1H, dd, J=2.0, 7.6 Hz), 8.64 (1H, dd, J=2.0, 4.8 Hz).

*2-tert-butyl-4-methyl-4H-pyrido[2,3-d][1,3]oxazin-4-yl pivalate $^1$H-NMR Spectrum (CDCl$_3$) δ (ppm): 1.09 (9H, s), 1.32 (9H, s), 2.05 (3H, s), 7.14 (1H, dd, J=4.8, 7.6 Hz), 7.71 (1H, dd, J=2.0, 7.6 Hz), 8.51 (1H, dd, J=2.0, 4.8 Hz).

Reference Examples 6 to 7 are other synthesis methods to Reference Example 5.

Reference Example 6

Synthesis of 2-tert-butyl-4H-pyrido[2,3-d][1,3]oxazin-4-one

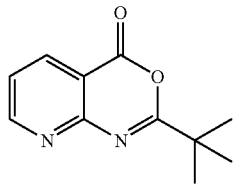

To a mixture of 2-aminonicotinic acid (13.8 g, 100 mmol), 4-dimethylaminopyridine (1.2 g, 10 mmol), triethylamine (55.8 mL, 400 mmol) and N-methylpyrrolidone (140 mL, 42 mmol) was added pivaloyl chloride (24.1 g, 200 mmol) dropwise at 0° C., and after the drop wise addition was finished, which was stirred overnight at room temperature. To the reaction mixture was added water, extracted with toluene, and the organic layer was washed with water and saturated sodium chloride water. After the solution was dried over anhydrous magnesium sulfate and filtered, the solvent was evaporated under a reduced pressure. To the residue was added n-heptane, which was suspended and stirred at 0° C., which was filtered to obtain the title compound (16.6 g).

$^1$H-NMR Spectrum (CDCl$_3$) δ (ppm): 1.45 (9H, s), 7.48 (1H, dd, J=4.8, 8.0 Hz), 8.52 (1H, dd, J=2.0, 7.6 Hz), 8.97 (1H, dd, J=2.0, 4.8 Hz).

Reference Example 7

Synthesis of N-(3-acetylpyridin-2-yl)-2,2-dimethylpropanamide

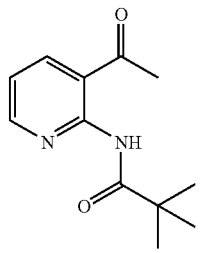

To a mixture of 2-tert-butyl-4H-pyrido[2,3-d][1,3]oxazin-4-one (10.2 g, 50 mmol) and tetrahydrofuran (50 mL) was added methyl magnesium bromide (0.97M tetrahydrofuran solution, 100 mL, 97 mmol) dropwise at −78° C., after the dropwise addition was finished, which was stirred at −78° C. for 30 minutes. To the reaction mixture were added a saturated aqueous solution of ammonium chloride and water, which was extracted with ethyl acetate, and the organic layer was washed with an aqueous solution of ammonium chloride. The solvent was evaporated under a reduced pressure and the precipitated solid was filtered to obtain the title compound (9.1 g).

$^1$H-NMR Spectrum (CDCl$_3$) δ (ppm): 1.33 (9H, s), 2.64 (3H, s), 7.10 (1H, dd, J=4.8, 8.0 Hz), 8.17 (1H, dd, J=2.0, 7.6 Hz), 8.64 (1H, dd, J=2.0, 4.8 Hz).

Reference Example 8

Synthesis of ethyl 5-{2-[(2,2-dimethylpropanoyl)amino]pyridin-3-yl}isoxazol-3-carboxylate

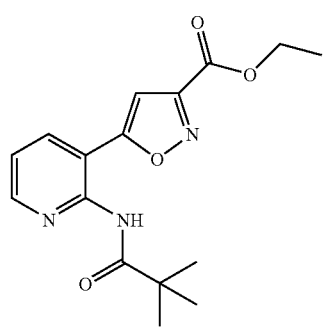

To a mixture of N-(3-acetyl pyridin-2-yl)-2,2-dimethylpropanamide (8.08 g, 36.7 mmol), diethyl oxalate (10.0 mL, 73.4 mmol) and ethanol (36 mL) was added potassium tert-butoxide (8.23 g, 73.4 mmol) at −25° C., which was stirred at −25° C. for one hour. The reaction mixture was added water (72 mL), which was stirred at room temperature, toluene (36 mL) was added, separated, and the obtained aqueous layer was further washed with toluene (36 mL). To the solution were added 5N hydrochloric acid (14 mL) and hydroxylamine hydrochloride (5.10 g, 73.4 mmol), which was stirred at room temperature for 30 minutes. To the reaction mixture was added 5N aqueous sodium hydroxide (14 mL), which was extracted with toluene, the solvent was evaporated under a reduced pressure. To the obtained residue were added ethanol (35 mL) and triethylamine (5 mL), which was stirred at 80° C. to 85° C. for six hours. To the reaction mixture was added n-heptane (105 mL) and the precipitated solid was filtered to obtain the title compound (6.90 g).

$^1$H-NMR Spectrum (DMSO-d6) δ (ppm): 1.19 (9H, s), 1.32 (3H, t), 4.37 (4H, q), 7.12 (1H, s), 7.46 (1H, dd, J=4.8, 8.0 Hz), 8.25 (1H, dd, J=2.0, 8.0 Hz), 8.58 (1H, dd, J=2.0, 4.8 Hz), 10.03 (1H, s).

Reference Example 9

Synthesis of N-{3-[3-(hydroxymethyl)isoxazol-5-yl]pyridin-2-yl}-2,2 dimethylpropanamide

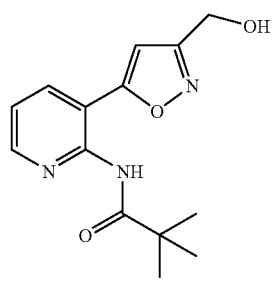

To a mixture of ethyl 5-{2-[(2,2-dimethylpropanoyl)amino]pyridin-3-yl}isoxazol-3-carboxylate (111 g, 350 mmol), ethanol (110 mL) and tetrahydrofuran (350 mL) was added sodium borohydride (13.2 g, 350 mmol) at room temperature, which was stirred at room temperature for 6 hours. To the reaction mixture were added water (350 mL) and 5N hydrochloric acid (90 mL), which was stirred at room temperature for 30 minutes, 5N aqueous sodium hydroxide (110 mL) was added thereto, the solution was extracted with a mixture of ethyl acetate and tetrahydrofuran, and the organic layer was washed with water and saturated sodium chloride water. The solvent was evaporated under a reduced pressure to obtain the title compound (83.8 g) as a yellow solid, partially contaminated with [5-(2-aminopyridin-3-yl)isoxazol-3-yl]methanol.

$^1$H-NMR Spectrum (DMSO-d$_6$) δ (ppm): 1.20 (9H, s), 4.52 (2H, d, J=6.0 Hz), 5.53 (1H, t, J=6.0 Hz), 6.70 (1H, s), 7.44 (1H, dd, J=4.8, 8.0 Hz), 8.19 (1H, dd, J=5.6, 7.6 Hz), 8.53 (1H, dd, J=2.0, 4.8 Hz), 9.89 (1H, brs).

Reference Example 10

Synthesis of
[5-(2-aminopyridin-3-yl)isoxazol-3-yl]methanol

To a mixture of N-{3-[3-(hydroxymethyl)isoxazol-5-yl]pyridin-2-yl}-2,2 dimethylpropanamide (82.8 g) obtained in Reference Example 9 and methanol (350 mL) was added 5N aqueous sodium hydroxide (350 mL) at room temperature, which was stirred at 57 to 60° C. for 14 hours. To the reaction mixture was added acetic acid (100 mL) and the precipitated solid was filtered to obtain the title compound (42.2 g) as a grayish white solid.

$^1$H-NMR Spectrum (DMSO-$d_6$) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

Reference Examples 11 to 13 are other synthesis methods to Reference Examples 5 to 10.

Reference Example 11

Synthesis of
N-(3-acetylpyridin-2-yl)-2,2-dimethylpropanamide

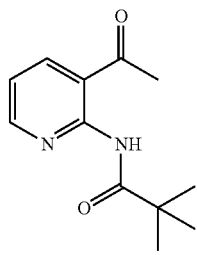

After 1-(2-aminopyridin-3-yl)ethanone (40.0 kg, 294 mol) was added to a 1500 L reactor, which was washed thereto down with toluene (approximately 15 kg). Then, after toluene was added until there was 347 kg of toluene in total, pivaloyl chloride (53.1 kg, 1.5M/M) was added thereto. Triethylamine (23.8 kg, 0.8M/M) was added thereto dropwise at an internal temperature of 30° C. or lower and the solution was stirred at an internal temperature of from 20 to 30° C. for one hour or longer. After triethylamine (23.8 kg, 0.8M/M) was again added dropwise at an internal temperature of 30° C. or lower, the solution was stirred at an internal temperature of from 20 to 30° C. for two hours or longer, it was confirmed by HPLC that the reaction had ended.

Under a brine cooling, water (100 L) was added dropwise at an internal temperature of 30° C. or lower, then, 35% hydrochloric acid (49.0 kg, 1.6M/M) was added thereto dropwise at an internal temperature of 30° C. or lower. After the reaction solution was stirred for five minutes, the solution was left standing still for 15 minutes or longer and lower layer (a) was separated into a poly container. After water (100 L) was added thereto and the solution was stirred for five minutes, the solution was left standing still for 15 minutes or longer. After lower layer (c) was separated into a poly container and upper layer (d) was removed, lower layer (a) and lower layer (c) were returned into the 1500 L reactor. Under the brine cooling, ethyl acetate (289 kg) was added thereto, then, after an aqueous solution of 48.7% sodium hydroxide (43.4 kg, 1.8M/M) was added dropwise at an internal temperature of 30° C. or lower and the solution was stirred for five minutes, it was confirmed with a UNIV test paper that a pH of the lower layer was from 8 to 9. After being left standing still for 15 minutes or longer, lower layer (e) and upper layer (f) were each separated and lower layer (e) was returned into the 1500 L reactor. After ethyl acetate (144 kg) was added thereto and the solution was stirred for five minutes, the solution was left standing still for 15 minutes or longer and lower layer (g) and upper layer (h) were each separated. After lower layer (g) was returned into the 1500 L reactor, ethyl acetate (144 kg) was added thereto and the solution was stirred for five minutes, the solution was left standing still for 15 minutes or longer. After removing lower layer (i), upper layer (f) and upper layer (h) were returned into the 1500 L reactor and which was washed thereto down with ethyl acetate (approximately 15 kg).

The organic layer returned into the 1500 L reactor was concentrated under a reduced pressure (50° C. hot water), and concentration was stopped once at the point of time when the concentrate reached approximately 200 L. The concentrate was removed into SUS containers and the inside of the reactor was washed out with toluene (17 kg). Approximately half of the amount of the removed concentrate was placed in a 300 L reactor and washed thereto down with toluene (9 kg). The concentrate was further concentrated under a reduced pressure (50° C. hot water), and when the amount of distillation from the condenser decreased, the remaining concentrate was placed in the 300 L reactor and which was washed thereto down with toluene (9 kg). Concentration under a reduced pressure was restarted (50° C. to 70° C. hot water). At the point of time when there was almost no distillation, water cooling was started and toluene (52 kg) was added thereto at an internal temperature of 50° C. or lower. Concentration under a reduced pressure was restarted (50 to 80° C. hot water). Concentration was stopped at the point of time when distillation was no longer observed at an external temperature of 80° C. and a reduced pressure level of −0.090 MPa or greater, and ethanol (61 kg) was added thereto at an internal temperature of from 20 to 30° C.

Under a nitrogen atmosphere, the ethanol solution inside the can was removed into a SUS container, and the can was washed out with ethanol (13 kg). After the removed solution was added into the 1500 L reactor, which was washed thereto down with ethanol (13 kg) to obtain an ethanol solution of the title compound (containing 69.4 kg of the target compound; yield: 107.3%).

HPLC conditions: column: YMC-Pack Pro 018 (5 μm, 150×4.6 mmI.D., YMC), mobile phase: acetonitrile/water/ammonium acetate=300/700/1 to 900/100/1 (v/v/w).

Reference Example 12

Synthesis of ethyl 5-{2-[(2,2-dimethylpropanoyl)amino]pyridin-3-yl}isoxazol-3-carboxylate

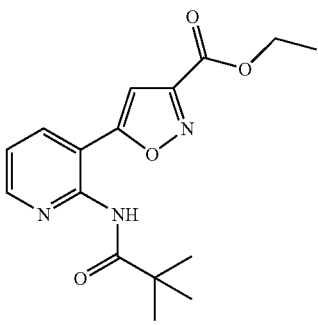

Under a nitrogen gas stream, diethyl oxalate (64.4 kg, 1.5M/M) was added to the ethanol solution of N-(3-acetyl pyridin-2-yl)-2,2-dimethylpropanamide (294 mol, assuming that the yield of the previous step was 100%) in the 1500 L reactor. Brine circulation was started and a pre-cooled ethanol solution of 22% potassium tert-butoxide (212.5 kg, 1.45M/M) was added dropwise thereto at an internal temperature of 10° C. or lower. After stirring at an internal temperature of from −5 to 10° C. for 30 minutes or longer, it was confirmed by HPLC that the reaction had ended.

Next, hydroxylamine hydrochloride (40.8 kg, 2.0M/M) was added thereto at an internal temperature of 10° C. or lower, and the solution was stirred at an internal temperature of 10° C. or lower for one hour or longer. Next, prepared and cooled beforehand, hydrous ethanol (ethanol (15.3 kg)/water (5.2 kg)) was added dropwise thereto at an internal temperature of 20° C. or lower while watching for heating, and water (582 L) was added dropwise at an internal temperature of 30° C. or lower. Switching to hot water (28° C.) circulation, ethyl 4-{2-[(2,2-dimethylpropanoyl)amino]pyridin-3-yl}-2-(hydroxyimino)-4-oxobutanoate (approximately 10 g) was added thereto at an internal temperature of from 20 to 30° C. After confirming the precipitation of solid visually, the suspension was stirred overnight at an internal temperature of from 15 to 25° C. After confirming by HPLC that the reaction had ended, and an aqueous solution of 48.7% sodium hydroxide was added dropwise thereto at an internal temperature of from 10 to 25° C. until a pH of the solution was from 6.50 to 7.00 (18.1 kg used). After stirring at an internal temperature of from 10 to 20° C. for three hours or longer, solid-liquid separation was carried out with a centrifuge divided into six times. At each centrifugation, after washing the cake with hydrous ethanol (ethanol (2.4 kg)/water (12 kg)) prepared beforehand, the cake was washed with water until a color of the wash was colorless transparent (approximately 200 L). After centrifugal separation was continued further for 30 minutes or longer, and a wet solid was removed into a poly bag. Next, in a shelf dryer, under 45 to 50° C. hot water circulation, the wet solid was dried under a reduced pressure to obtain a solid (71.52 kg).

Next, the solid obtained above (71.45 kg) was added to the 1500 L reactor and washed thereto down with ethanol (approximately 7 kg). Then, ethanol was added up to 226 kg in total and triethylamine (21.6 kg, 1 M/M) was added thereto. Hot water (75° C.) circulation was started, the solution was stirred at an internal temperature of from 70 to 75° C. for 14 to 16 hours, and it was confirmed by HPLC that the reaction had ended. Next, n-heptane (488.7 kg) was added dropwise thereto at an internal temperature of from 55 to 75° C. Thereafter, ethyl 5-{2-[(2,2-dimethylpropanoyl)amino]pyridin-3-yl}isoxazol-3-carboxylate (approximately 5 g) was added thereto at an internal temperature of from 50 to 53° C., and it was confirmed visually that a solid precipitated at an internal temperature of from 45 to 50° C. Then, after the temperature of hot water was decreased gradually, cooling to an internal temperature of 15° C. or lower, further, by brine or cold water cooling, the solution was stirred overnight at an internal temperature of from 0 to 10° C. Using a filtration apparatus, the suspension was filtered and washed with a mixed solution of n-heptane/ethanol (n-heptane (70 kg)/ethanol (10 kg)), followed by n-heptane (80 kg). After drying was carried out in nitrogen for 15 minutes or longer subsequent, a wet solid was removed to a SUS container. In a shelf dryer under 45 to 50° C. hot water circulation, the wet solid was dried under a reduced pressure to obtain the title compound (54.55 kg; yield: 58.6%).

$^1$H-NMR Spectrum (DMSO-d6) δ (ppm): 1.19 (9H, s), 1.32 (3H, t), 4.37 (4H, q), 7.12 (1H, s), 7.46 (1H, dd, J=4.8, 8.0 Hz), 8.25 (1H, dd, J=2.0, 8.0 Hz), 8.58 (1H, dd, J=2.0, 4.8 Hz), 10.03 (1H, s).

HPLC conditions: column: YMC-Pack Pro C18 (5 μm, 150×4.6 mmI.D., YMC), mobile phase: acetonitrile/water/ammonium acetate=300/700/1 to 900/100/1 (v/v/w).

Reference Example 13

Synthesis of [5-(2-aminopyridin-3-yl)isoxazol-3-yl]methanol

Under a nitrogen gas stream, ethyl 5-{2-[(2,2-dimethylpropanoyl)amino]pyridin-3-yl}isoxazol-3-carboxylate (54.5 kg, 172 mol) was added to a 1500 L reactor and washed thereto down with methanol (4.9 kg). Then, methanol was added thereto until there was 108 kg of methanol in total and triethylamine (8.7 kg, 0.5M/M) was added consecutively. After hot water (60° C.) circulation was started, the solution was stirred at an internal temperature of from 50 to 60° C. for two hours or longer, and it was confirmed by HPLC (Condition 1) that the reaction had ended.

Next, water cooling was started and tetrahydrofuran (121 kg) was added thereto at an internal temperature of 30° C. or lower. Switching to brine cooling, under a nitrogen gas stream, at an internal temperature of from 0 to 10° C., sodium borohydride (7.15 kg, 1.1 M/M) was added thereto, split over 5 hours or longer. After addition of sodium borohydride was finished, the jacket was switched to cold water (4.0° C.) circulation, and the solution was stirred overnight at an internal temperature of from 0 to 10° C. On the next day, at an internal temperature of from 0 to 10° C., sodium borohydride (1.30 kg, 0.2M/M) was added thereto, split over one hour or longer. The jacket was switched to cold water, the internal temperature was heated up to from 20 to 30° C. over three hours or longer, and further, the stirring was carried out overnight at an internal temperature of from 20 to 30° C. On the next day, how the reaction was progressing was checked by HPLC, and since the reaction almost did not progress, the solution was cooled again and sodium borohydride (1.30 kg, 0.2M/M) was split-added at an internal temperature of from 0 to 10° C. After stirring at an internal temperature of from 0 to 10° C. for one hour or longer, the jacket was switched to cold water circulation and heated up to an internal temperature of from 15 to 25° C. over two hours or longer. After stirring for one hour or longer, it was confirmed by HPLC (Condition 1) that the reaction had ended, and the solution was stirred overnight.

The next day, after an aqueous solution of 48.7% sodium hydroxide (71 kg, 5M/M) was added dropwise thereto at an internal temperature of 50° C. or lower, in continuation, water (133 L) was added dropwise thereto at an internal temperature of 50° C. or lower. Hot water (50 to 80° C.) circulation was started, after stirring at an internal temperature of from 50 to 60° C. for 20 hours or longer, it was confirmed by HPLC (Condition 2) that the reaction had ended.

Next, under a water cooling, water (73 L) was added dropwise thereto. After switching to cold water (15° C.) cooling, [5-(2-aminopyridin-3-yl)isoxazol-3-yl]methanol was added thereto at an internal temperature of from 15 to 30° C., and precipitation of solid was confirmed, water (218 L) was added dropwise thereto, then, under a brine cooling, 35% hydrochloric acid (115 kg) was added dropwise thereto at an internal temperature of from 15 to 30° C., and which was washed there to down with water (3 L). After stirring at an internal temperature of from 15 to 30° C. for five minutes or longer, it was confirmed that a pH of the reaction solution was from 4.00 to 5.00 with a pH meter, and the solution was stirred at an internal temperature of from 15 to 30° C. for one hour or longer. Then, an aqueous solution of 48.7% sodium hydroxide (17.1 kg employment) was added dropwise thereto until a pH of the solution was from 7.00 to 8.00, and the solution was left standing still overnight. On the next day, after stirring and pressure reduction were started and distillation from the condenser was confirmed, hot water (40° C.) circulation was started. Concentration was carried out for one hour or longer under the conditions of hot water (35 to 45° C.), 68 cm Hg or greater level of reduced pressure, and 30° C. or higher internal temperature. The reduced pressure was released under a nitrogen and the solid attached to the reactor wall was washed thoroughly with water (approximately 20 L). The solution was stirred at an internal temperature of from 15 to 30° C. for three hours or longer and was left standing still overnight. On the next day, the internal temperature was confirmed to be within a range of from 15 to 25° C., the slurry solution was solid-liquid separated with a centrifuge, divided in two stages. At each centrifugation, the solid was washed with water (approximately 200 L), after draining, centrifugal separation was carried out for one hour and then the wet solid was taken out into a poly bag. Then, in a shelf dryer, under 45 to 50° C. hot water circulation, the solid was dried under a reduced pressure to obtain the title compound (26.57 kg, yield: 80.9%).

$^1$H-NMR Spectrum (DMSO-d$_6$) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

HPLC condition 1: column: YMC-Pack Pro C18 (5 μm, 150×4.6 mmI.D., YMC), mobile phase: acetonitrile/water/ammonium acetate=300/700/1 to 900/100/1 (v/v/w).

HPLC condition 2: column: YMC-Pack ODS-AQ (5 μm, 150×4.6 mmI.D., YMC), mobile phase: acetonitrile/water/85% phosphoric acid/sodium 1-octane sulfonate=161.3/838.7/1/1.1 to 900/100/1/1.1 (v/v/v/w).

Reference Examples 14 to 15 are other synthesis methods to Reference Example 10.

Reference Example 14

Synthesis of [5-(2-aminopyridin-3-yl)isoxazol-3-yl]methanol oxalate

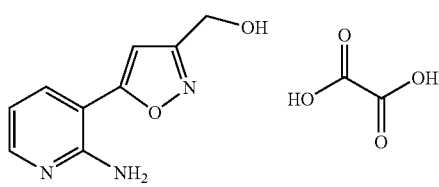

To a mixture of ethyl 5-{2-[(2,2-dimethylpropanoyl)amino]pyridin-3-yl}isoxazol-3-carboxylate (3.17 g, 10 mmol), ethanol (3 mL) and tetrahydrofuran (10 mL) was added sodium borohydride (0.38 g, 10 mmol) at room temperature, which was stirred overnight under a ice cooling to room temperature. The reaction mixture was divided equally into five, among which one was added to 5N aqueous sodium hydroxide (2 mL), which was stirred overnight at 55° C. To the reaction mixture was added water, which was extracted with a mixture of methyl-tert-butylether and tetrahydrofuran, and oxalic acid (0.18 g, 2 mmol) was added to the organic layer. The precipitated solid was filtered to obtain the title compound (0.39 g) as a white solid.

$^1$H-NMR Spectrum (DMSO-d$_6$) δ (ppm): 4.54 (2H, s), 6.31 (2H, brs), 6.72 (1H, dd, J=4.8, 8.0 Hz), 6.89 (1H, s), 7.90 (1H, dd, J=2.0, 8.0 Hz), 8.09 (1H, dd, J=2.0, 4.8 Hz).

Reference Example 15

Synthesis of [5-(2-aminopyridin-3-yl)isoxazol-3-yl]methanol

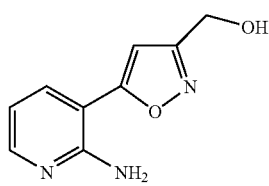

To a mixture of [5-(2-aminopyridin-3-yl)isoxazol-3-yl]methanol oxalate (0.39 g) and water (2 mL) was added 5N aqueous sodium hydroxide (0.5 mL) at room temperature and the precipitated solid was filtered to obtain the title compound (0.18 g) as a white solid.

¹H-NMR Spectrum (DMSO-d₆) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

Reference Example 16

Synthesis of 3-[3-(chloromethyl)isoxazol-5-yl]pyridin-2-amine

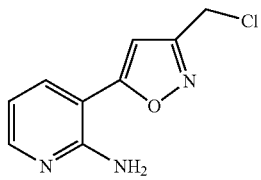

To a mixture of [5-(2-aminopyridin-3-yl)isoxazol-3-yl]methanol (0.19 g, 1 mmol) and N,N-dimethyl acetamide (1 mL) was added a mixture of thionyl chloride (0.15 mL, 2 mmol), benzotriazole (0.26 g, 2.2 mmol) and tetrahydrofuran (1 mL) under an ice cooling, which was stirred at room temperature for 30 minutes. To the reaction mixture were added water and 5N aqueous sodium hydroxide to adjust basic, then extracted with ethyl acetate, and the organic layer was washed with saturated sodium chloride water. The solvent was evaporated under a reduced pressure to obtain the title compound (0.21 g) as a pale yellow solid.

¹H-NMR Spectrum (DMSO-d₆) δ (ppm): 4.84 (2H, s), 6.31 (2H, brs), 6.72 (1H, dd, J=4.8, 8.0 Hz), 7.04 (1H, s), 7.91 (1H, dd, J=1.6, 7.6 Hz), 8.11 (1H, dd, J=1.2, 4.8 Hz).

Reference Example 17

Synthesis of di-tert-butyl{3-[3-(chloromethyl)isoxazol-5-yl]pyridin-2-yl}imidodicarbonate

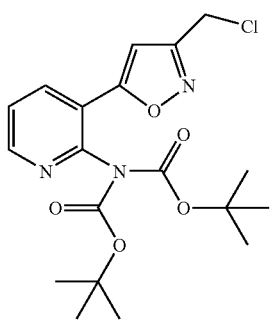

To a mixture of 3-[3-(chloromethyl)isoxazol-5-yl]pyridin-2-amine (420 mg, 2.01 mmol), 4-dimethyl aminopyridine (26.8 mg, 0.220 mmol), and tetrahydrofuran (2.1 mL) was added di-tert-butyldicarbonate (924 mg, 4.24 mmol) at room temperature, which was stirred. After 25 hours, to the reaction solution was added water and extracted with toluene, then the organic layer was washed with 5% sodium chloride water and the solvent was evaporated under a reduced pressure to obtain the title compound (880 mg) as a pale yellow oily product.

¹H-NMR Spectrum (CDCl₃) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

Reference Examples 18 to 21 are other synthesis methods to Reference Examples 9 to 10 and Reference Examples 16 to 17.

Reference Example 18

Synthesis of tert-butyl{3-[3-(hydroxymethyl)isoxazol-5-yl]pyridin-2-yl}carbamate

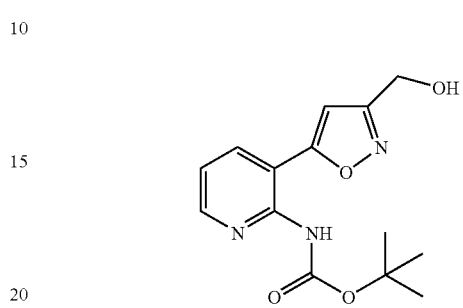

To a mixture of ethyl 5-{2-[(2,2-dimethylpropanoyl)amino]pyridin-3-yl}isoxazol-3-carboxylate (1.59 g, 5 mmol), di-tert-butyl dicarbonate (1.31 g, 6 mmol), and tetrahydrofuran (5 mL) was added 4-dimethylaminopyridine (61 mg, 0.5 mmol) at room temperature, which was stirred at room temperature for one hour and then stirred at 60° C. for six hours. To the reaction mixture were added ethanol (2.5 mL) and sodium borohydride (0.57 g, 15 mmol), which was stirred at 0° C. for 30 minutes and then stirred overnight at room temperature. To the reaction mixture was added water, extracted with ethyl acetate, and the organic layer was washed with water and saturated sodium chloride water. After drying over anhydrous magnesium sulfate and filtering, the solvent was evaporated under a reduced pressure to obtain the title compound (1.60 g).

¹H-NMR Spectrum (CDCl3) δ (ppm): 1.47 (9H, s), 4.83 (2H, s), 6.63 (1H, s), 7.17 (1H, dd, J=4.8, 8.0 Hz), 7.58 (1H, s), 7.97 (1H, dd, J=2.0, 8.0 Hz), 8.51 (1H, dd, J=2.0, 4.8 Hz).

Reference Example 19

Synthesis of tert-butyl{3-[3-(chloromethyl)isoxazol-5-yl]pyridin-2-yl}carbamate

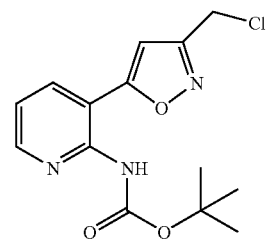

Under a nitrogen atmosphere, benzotriazole (3.55 g, 29.5 mmol) was dissolved in N,N-dimethylacetamide (10 mL), and thionyl chloride (2.06 mL, 26.8 mmol) was added dropwise thereto under an ice water cooling to prepare a solution of thionyl chloride-benzotriazole (1:1.1) in N,N-dimethylacetamide.

Under a nitrogen atmosphere, tert-butyl{3-[3-(hydroxymethyl)isoxazol-5-yl]pyridin-2-yl}carbamate (781 mg, 2.68 mmol) was dissolved in N,N-dimethylacetamide (2.7 mL). To the solution was added the above solution of thionyl chloride-benzotriazole (1:1.1) in N,N-dimethylacetamide (6 mL, 14.4 mmol) dropwise under an ice water cooling, which was stirred at the same temperature for one hour and then stirred at room temperature. After one hour and 20 minutes, under the ice water cooling, a solution of thionyl chloride-benzotriazole (1:1.1) in N,N-dimethylacetamide (2.2 mL, 5.12 mmol) was added dropwise thereto, and the solution was stirred at room temperature for one hour. Under the ice water cooling, to the reaction solution were added 1N aqueous sodium hydroxide and tert-butylmethylether to adjust basic and then extracted. The organic layer was washed sequentially with 0.5N aqueous sodium hydroxide and 5% sodium chloride water, dried over anhydrous magnesium sulfate and then the solvent was evaporated under a reduced pressure to obtain a crude body of the title compound (953 mg) as a pale yellow oily product.

$^1$H-NMR Spectrum (CDCl$_3$) δ (ppm): 1.47 (9H, s), 4.65 (2H, s), 6.67 (1H, s), 7.20 (1H, dd, J=4.8, 8.0 Hz), 7.44 (1H, brs), 8.01 (1H, dd, J=2.0, 8.0 Hz), 8.52 (1H, dd, J=2.0, 4.8 Hz).

Reference Example 20

Synthesis of di-tert-butyl{3-[3-(chloromethyl)isoxazol-5-yl]pyridin-2-yl}iidodicarbonate

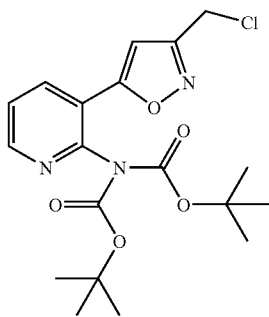

A crude matter of tert-butyl{3-[3-(chloromethyl)isoxazol-5-yl]pyridin-2-yl}carbamate (1.13 g, 3.17 mmol) was dissolved in tetrahydrofuran (7.0 mL), di-tert-butyl dicarbonate (761 mg, 3.49 mmol) was added thereto under an ice water cooling and washed thereto down with THF (3.0 mL). Then, after 4-dimethylaminopyridine (39.1 mg, 0.317 mmol) was added thereto, the solution was stirred at room temperature. After five hours, under the ice water cooling, to the reaction solution were added ethyl acetate and 5% sodium chloride water and extracted. After the organic layer was washed with 5% sodium chloride water and dried over anhydrous magnesium sulfate, the solvent was evaporated under a reduced pressure. The residue was purified by silica gel column chromatography to obtain the title compound (1.14 g) as a pale yellow solid.

$^1$H-NMR Spectrum (CDCl$_3$) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

Reference Example 21

Synthesis of di-tert-butyl{3-[3-(chloromethyl)isoxazol-5-yl]pyridin-2-yl}imidodicarbonate

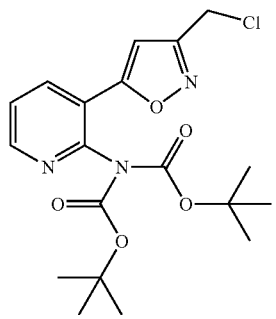

Under a nitrogen gas stream, [5-(2-aminopyridin-3-yl)isoxazol-3-yl]methanol (26.00 kg, 136.0 mol) and 1,3-dimethyl-2-imidazolidinone (143 kg, 5.5 w/w, a portion was set aside for thorough wash) were added to a 500 L reactor 1 and stirring was started. The solution was stirred at an internal temperature of from 35 to 45° C. for one hour or longer and cooled after dissolution of [5-(2-aminopyridin-3-yl)isoxazol-3-yl]methanol. At an internal temperature of from 5 to 25° C., thionyl chloride (19.40 kg, 163.1 mol, 1.2M/M) was added dropwise thereto. After the dropwise addition was finished, thionyl chloride was thoroughly washed down with the set aside 1,3-dimethyl-2-imidazolidinone, the solution was stirred an internal temperature of from 5 to 25° C. for 12 hours or longer. After the end of the reaction was confirmed by HPLC analysis, an aqueous solution of approximately 36% sodium hydroxide (mixed solution between an aqueous solution of 48% sodium hydroxide (15.9 kg; 190.8 mol, 1.4M/M as sodium hydroxide) and water (5.3 kg, 0.2 w/w)) was added dropwise thereto at an internal temperature of from 0 to 25° C., and then ethyl acetate (164 kg, 6.31 w/w) and water (74.2 kg, 2.85 w/w) were added dropwise at an internal temperature of from 15 to 35° C. In addition, after an aqueous solution of approximately 8% sodium hydroxide (mixed solution between a solution of 48% sodium hydroxide (13.6 kg; 163.2 mol, 1.20M/M as sodium hydroxide) and water (68.0 kg, 2.6 w/w)) was added dropwise thereto at an internal temperature of from 0 to 25° C. and the internal temperature was adjusted to 15 to 30° C., the solution was stirred at the same temperature range for 30 minutes or longer and left standing still for 30 minutes or longer. The lower layer and the upper layer were removed separately, each of the respective ½ weights was added to the 500 L reactor 1 and a 500 L reactor 2.

Post-processing of the 500 L reactor 1 was carried out as described below. After stirring was started and water (52 kg, 2 w/w) was added thereto, an aqueous solution of approximately 8% sodium hydroxide (mixed solution between an aqueous solution of 48% sodium hydroxide (11.3 kg; 135.6 mol, 1.0M/M as sodium hydroxide) and water (56.5 kg, 2.17 w/w)) was added dropwise little by little at an internal temperature of from 0 to 25° C. to adjust a pH of the lower layer to from 7.00 to 8.50 (actual value: pH7.84). At this time, 35.55 kg of the aqueous solution of approximately 8% sodium hydroxide was used. Then, after the internal temperature was adjusted to 15 to 30° C. and the solution was stirred for 30 minutes or longer, the solution was left standing still overnight. On the next day, after the pH was confirmed again to be pH 7.59, the upper layer and the lower layer were respectively separated, only the lower layer was returned to the 500 L reactor 1, and then ethyl acetate (82 kg, 3.15 w/w) was added thereto. After stirring at an internal temperature of from 15 to 30° C. for five minutes, the solution was left standing still for 30 minutes or longer, and the lower layer (pH7.55) was eliminated. To the upper layer that was left in the reactor were added the separated upper layer and 5% sodium chloride water (mixed solution between sodium chloride (3.3 kg, 0.13 w/w) and water (618 kg, 2.38 w/w)), which was stirred at an internal temperature of from 15 to 30° C. for five minutes, then left standing still for 30 minutes or longer and the lower layer (pH8.23) was eliminated. Furthermore, water (65 kg, 2.5 w/w) was added thereto, the solution was stirred at an internal temperature of from 15 to 30° C. for five minutes and then left standing still overnight, and the lower layer (pH7.04) was eliminated.

The post-processing of the 500 L reactor 2 was conducted concurrently with the operations for the 500 L reactor 1, the same procedure was carried out.

Next, the upper layer of the 500 L reactor 2 was transferred to the 500 L reactor 1, and the solution was concentrated under a reduced pressure at 45 to 55° C. hot water and −0.070 to −0.085 MPa level of the reduced pressure until the content solution was approximately 200 L. Ethyl acetate (141 kg, 5.42 w/w) was added therein, and the solution was concentrated again under a reduced pressure with the same conditions. After this operation was repeated further twice, before and after the 4$^{th}$ time addition of ethyl acetate (141 kg, 5.42 w/w), the 3-[3-(chloromethyl)isoxazol-5-yl]pyridin-2-amine content in the solution was checked by HPLC analysis, the 3-[3-(chloromethyl)isoxazol-5-yl]pyridin-2-amine content (23.35 kg, 111.4 mol) in the solution and the yield thereof (81.9%) were calculated. Then, concentration under a reduced pressure was carried out once more with the same conditions until the 3-[3-(chloromethyl)isoxazol-5-yl]pyridin-2-amine content was 10.0 to 13.0% to obtain a solution of 3-[3-(chloromethyl)isoxazol-5-yl]pyridin-2-amine in ethyl acetate.

Under a nitrogen gas stream, the solution of 3-[3-(chloromethyl)isoxazol-5-yl]pyridin-2-amine in ethyl acetate (containing the total amount obtained in the previous step, 23.35 kg (111.4 mol)) inside the 500 L reactor 1 was stirred, di-tert-butyl dicarbonate (53.47 kg, 245.0 mol, 2.2M/M) was added thereto at an internal temperature of from 15 to 25° C. and which was washed thereto down with ethyl acetate (2 kg). A solution of 4-dimethyl aminopyridine in ethyl acetate (mixed solution of 4-dimethylaminopyridine (0.409 kg, 3.35 mol, 0.03M/M) and ethyl acetate (8 kg)) prepared beforehand was added therein, and after washing down with ethyl acetate (1 kg), the solution was stirred at an internal temperature of from 10 to 30° C. for 22 hours or longer. After checking the end of the reaction by HPLC analysis, 1,3-dimethyl-2-imidazolidinone (50 kg, 2.12 w/w) was added thereto. The solution was concentrated under a reduced pressure at 45 to 55° C. hot water circulation, until −0.092 MPa or greater level of the reduced pressure and liquid distillation weakened, and after checking by GC analysis that the ethyl acetate content was 7.0%, the reactor was cooled to an internal temperature of 30° C. or lower, and the solution was left standing still overnight. On the next day, to the concentration residue was added methanol (111 kg, 4.74 w/w), which was stirred for 10 minutes or longer, and it was confirmed that no solid had precipitated, the solution was divided into two fractions. Next, the solutions divided into two fractions were added respectively to the 500 L reactors 1 and 2, and respectively washed thereto down with methanol (9 kg each, 0.4 w/w each). In so doing, as a result of analyzing by HPLC the solution prior to the two fraction division (225.65 kg), the target di-tert-butyl{3-[3-(chloromethyl)isoxazol-5-yl]pyridin-2-yl}imidodicarbonate content was 19.37%, and the weight of di-tert-butyl {3-[3-(chloromethypisoxazol-5-yl]pyridin-2-yl}imidodicarbonate contained was 43.71 kg (106.6 mol, yield: 95.7%).

For the 500 L reactor 1 the processing was as described below. After stirring was started, at an internal temperature of from 35 to 45° C., water (35 kg, 1.5 w/w) was added dropwise thereto over 30 minutes or longer, and di-tert-butyl{3-[3-(chloromethyl)isoxazol-5-yl]pyridin-2-yl}imidodicarbonate (0.010 kg) was added thereto at an internal temperature of from 35 to 40° C. After stirring at an internal temperature of from 35 to 40° C. for 30 minutes or longer, precipitation of solid was checked, and the solution was stirred further at the same temperature range for one hour or longer. Then, after water (three times 35 kg, 1.5 w/w each) was added dropwise thereto over 30 minutes or longer at an internal temperature of from 35 to 45° C., the reactor was cooled to an internal temperature of from 5 to 15° C. over 3 hours or longer, and the solution was stirred at the same temperature range for 12 hours or longer. Solid-liquid separation was carried out with a centrifuge dividing into two times, and the cake was washed with hydrous methanol (mixed solution of methanol (each time 7 kg, 0.3 w/w) and water (each time 27 kg, 1.14 w/w)). After washing was finished, centrifugal separation was carried out for 30 minutes or longer to obtain a wet solid of the title compound (25.80 kg). This wet solid was loaded into a mixing type vacuum dryer and vacuum dried at an external temperature from 45 to 55° C. for 24 hours or longer to obtain the title compound (21.09 kg) as a pale yellow solid.

The operation for the 500 L reactor 2 was carried out concurrently with the above, the same operations were performed to obtain the title compound (21.22 kg) as a pale yellow solid.

Accordingly, the title compound (42.31 kg, yield: 92.7%) was obtained.

$^1$H-NMR Spectrum (CDCl$_3$) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

HPLC conditions: column: YMC-Pack Pro C18 (5 μm, 150×4.6 mmI.D YMC), mobile phase: acetonitrile/water/ammonium acetate=300/700/1 to 900/100/1 (v/v/w).

GC Conditions: column: DB-624 (30 m, 0.53 mmI.D., Film 3 μm, Agilent).

Reference Example 22

Ethyl 5-{2-[(2,2-dimethylpropoxycarbonyl)amino]pyridin-3-yl}isoxazol-3-carboxylate

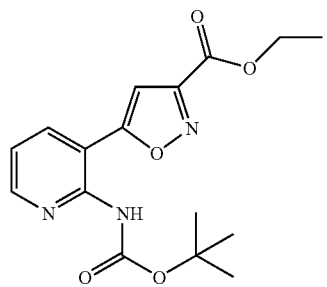

To a mixture of 4-methylen-2-oxo-4H-pyrido[2,3-d][1,3]oxazin-1-carboxylic acid tert-butyl ester (2.71 g, 10.37 mmol), which was synthesized according to the methods described in the pamphlet of the International Publication WO 08/136,279, Specifications, Preparation Example 3-3-1, triethylamine (4.2 mL, 30 mmol) and tetrahydrofuran (30 mL) was added ethyl 2-chloro-2-(hydroxyimino)acetate (4.5 g, 30 mmol) at 0° C. over two hours and then stirred at room temperature for 14 hours. To the reaction mixture was added water, extracted with ethyl acetate and the organic layer was washed with water and saturated sodium chloride water. After drying over magnesium sulfate and filtering, the solvent was evaporated under a reduced pressure. The residue was suspended and washed with a 1:1 mixture of n-hexane and ethyl acetate to obtain the title compound (1.56 g).

$^1$H-NMR Spectrum (CDCl3) δ (ppm): 1.44 (3H, t, J=6.8 Hz), 1.46 (9H, s), 4.47 (4H, q, J=7.2 Hz), 6.95 (1H, s), 7.22 (1H, dd, J=4.8, 8.0 Hz), 7.42 (1H, bs), 8.05 (1H, dd, J=2.0, 8.0 Hz), 8.52 (1H, dd, J=2.0, 4.8 Hz).

Reference Example 23

Ethyl 5-{2-[bis(2,2-dimethylpropoxy-carbonyl)amino]pyridin-3-yl}isoxazol-3-carboxylate

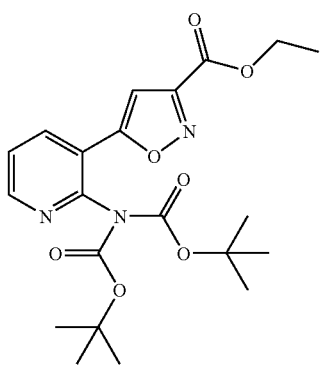

To a mixture of ethyl 5-{2-[(2,2-dimethylpropoxycarbonyl)amino]pyridin-3-yl}isoxazol-3-carboxylate (1.46 g, 4.38 mmol), di-tert-butyl dicarbonate (1.46 g, 6.69 mmol) and tetrahydrofuran (25 mL) was added 4-dimethylaminopyridine (30 mg, 0.25 mmol) at room temperature, which was stirred at room temperature for 14 hours. To the reaction mixture was added water, extracted with ethyl acetate, and the organic layer was washed with water and saturated sodium chloride water. After drying over magnesium sulfate and filtering, the solvent was evaporated under a reduced pressure and the residue was purified by silica gel column chromatography (hexane:ethyl acetate=3:1 then 1:1) to obtain the title compound (1.96 g).

$^1$H-NMR Spectrum (CDCl3) δ (ppm): 1.36 (18H, s), 1.46 (3H, t, J=6.8 Hz), 4.47 (4H, q, J=6.8 Hz), 6.93 (1H, s), 7.46 (1H, dd, J=4.8, 7.6 Hz), 8.29 (1H, d, J=7.6 Hz), 8.64 (1H, d, J=4.8 Hz).

Reference Example 24

Di-tert-butyl{3-[3-(hydroxymethyl)isoxazol-5-yl]pyridin-2-yl}imidodicarbonate

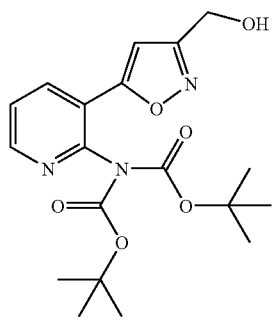

To a mixture of ethyl 5-{2-[bis(2,2-dimethylpropoxycarbonyl)amino]pyridin-3-yl}isoxazol-3-carboxylate (1.73 g, 4 mmol), ethanol (5 mL) and tetrahydrofuran (5 mL) was added sodium borohydride (0.15 g, 4 mmol) at 0° C., which was stirred at room temperature for one hour. Sodium borohydride (0.15 g, 4 mmol) was further added thereto and the solution was stirred at room temperature for three hours. To the reaction mixture was added water, extracted with ethyl acetate and the organic layer was washed with water and saturated sodium chloride water. After drying over anhydrous magnesium sulfate and filtering, the solvent was evaporated under a reduced pressure. The residue was added with a mixture of n-hexane-ethyl acetate (1:1), suspended and stirred, and then filtered to obtain the title compound (1.02 g).

$^1$H-NMR Spectrum (CDCl$_3$) δ (ppm): 1.33 (18H, s), 4.81 (2H, s), 6.60 (1H, s), 7.43 (1H, dd, J=4.8, 8.0 Hz), 8.27 (1H, dd, J=2.0, 8.0 Hz), 8.60 (1H, dd, J=2.0, 4.8 Hz).

Reference Example 25

Di-tert-butyl{3-[3-(bromomethyl)isoxazol-5-yl]pyridin-2-yl}imidodicarbonate

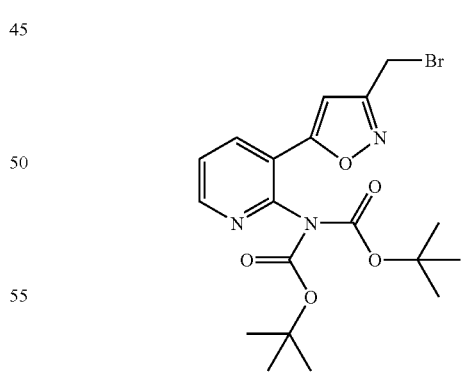

To a mixture of di-tert-butyl{3-[3-(hydroxymethyl)isoxazol-5-yl]pyridin-2-yl}imidodicarbonate (0.78 g, 2 mmol), triethylamine (1.95 mL, 14 mmol) and 1,2-dimethoxyethane (10 mL) was added phosphorus tribromide (0.37 mL, 4 mmol) dropwise at 0° C., which was stirred at room temperature for two hours, and then stirred at 50° C. for 30 minutes. The reaction mixture was cooled to 0° C., then water was added thereto and extracted with ethyl acetate, and the organic layer was washed with saturated sodium chloride water. After drying over anhydrous magnesium sulfate and filtering, the solvent was evaporated under a reduced pressure, the residue was purified by silica gel column chromatography to obtain the title compound (0.14 g).

$^1$H-NMR Spectrum (CDCl3) δ (ppm): 1.33 (18H, s), 4.45 (2H, s), 6.63 (1H, s), 7.43 (1H, dd, J=4.8, 8.0 Hz), 8.28 (1H, dd, J=2.0, 8.0 Hz), 8.61 (1H, dd, J=2.0, 4.8 Hz).

Reference Example 26

Synthesis of 2-[(4-bromobenzyl)oxy]pyridine

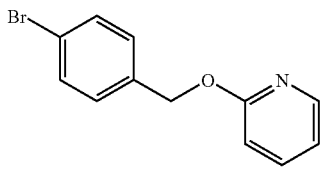

To a solution of 4-bromobenzyl alcohol (18 g, 94.3 mmol) in dimethylsulfoxide (85 mL) was added potassium tert-butoxide (11.5 g, 99 mmol) little by little under a nitrogen atmosphere at room temperature, which was stirred for 10 minutes. To this solution was added 2-fluoropyridine (12.3 g, 123 mmol) dropwise over 30 minutes under a water bath cooling. After stirring at room temperature for two hours, ethyl acetate and 5% sodium chloride water were added, and extracted. After the organic layer was washed sequentially with water and 5% sodium chloride water, the solvent was evaporated under a reduced pressure to obtain the title compound (24.3 g) as a yellow oily product.

$^1$H-NMR Spectrum (CDCl$_3$) δ (ppm): 5.33 (2H, s), 6.87-6.70 (1H, m), 6.98-7.02 (1H, m), 7.38-7.44 (2H, m), 7.55-7.60 (2H, m), 7.71-7.76 (1H, m), 8.15-8.18 (1H, m).

Reference Example 27 is the other synthesis method to Reference Example 26.

Reference Example 27

Synthesis of 2-[(4-bromobenzyl)oxy]pyridine

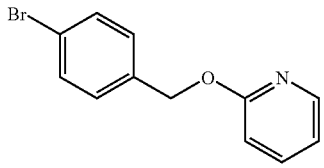

Under a nitrogen atmosphere, to a solution of 4-bromobenzyl alcohol (600 g, 3.21 mol) and 2-fluoropyridine (343 g, 3.53 mol) in tetrahydrofuran (1069 mL) was added a solution of potassium tert-butoxide (396 g, 3.53 mol) in tetrahydrofuran (3208 mL) (63 min, 9.2 to 20.5° C.) dropwise under a 7° C. cooling. After stirring at 22° C. for three hours, an aqueous solution of 5% sodium bicarbonate (prepared from sodium bicarbonate: 160 g and water: 3208 mL) was added thereto dropwise (20 min, 21.0 to 23.9° C.). Then, heptane (3220 mL) was added thereto and extracted, the organic layer was washed with water (800 mL). The organic layer was concentrated under a reduced pressure (to approximately 3200 mL), ethanol (1604 mL) was added thereto and concentrated under a reduced pressure (to approximately 3200 mL). Then, to the layer was added heptane (3200 mL), concentrated under a reduced pressure, heptane (3200 mL) was further added thereto and concentrated under a reduced pressure to obtain a solution of the title compound in heptane (2603 g, containing 789 g of the target product) as a brown oily product (yield: 93.2%).

$^1$H-NMR Spectrum (CDCl$_3$) δ (ppm): 5.33 (2H, s), 6.87-6.70 (1H, m), 6.98-7.02 (1H, m), 7.38-7.44 (2H, m), 7.55-7.60 (2H, m), 7.71-7.76 (1H, m), 8.15-8.18 (1H, m).

Reference Example 28

Synthesis of {4-[(pyridin-2-yloxy)methyl]phenyl}boronic acid

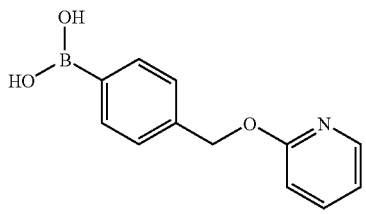

Under a nitrogen atmosphere, a solution of 2-[(4-bromobenzyl)oxy]pyridine (50 g, 190 mmol) in tetrahydrofuran (200 mL) was cooled to −78° C. and a 2.6M n-butyllithium hexane solution (88 mL, 228 mmol) was added thereto dropwise. After stirring for 45 minutes, trimethoxy borane (29.6 g, 285 mmol) was added thereto dropwise at the same temperature. After 30 minutes, a saturated aqueous solution of ammonium chloride and water were added thereto for quenching, and the solution was extracted with ethyl acetate. After the organic layer was washed with a mixture of saturated aqueous solution of ammonium chloride and saturated sodium chloride water and dried over anhydrous sodium sulfate, the solvent was evaporated under a reduced pressure. To the residue was added acetonitrile (200 mL), followed by suspending and stirring at 70° C. for 30 minutes, then, cooled, and stirred overnight at 4° C. The precipitated solid was filtered to obtain the title compound (11.2 g) as a white solid.

$^1$H-NMR Spectrum (CDCl$_3$) δ (ppm): 4.62 (2H, s), 5.42 (2H, s), 6.83 (1H, d, J=8.4 Hz), 6.87-6.92 (1H, m), 7.50 (2H, d, J=8.0 Hz), 7.57-7.62 (1H, m), 7.75 (2H, d, J=8.0 Hz), 8.16-8.19 (1H, m).

Reference Example 29

Synthesis of 2-{[4-(5,5-dimethyl-1,3,2-dioxaborinan-2-yl)benzyl]oxy}pyridine

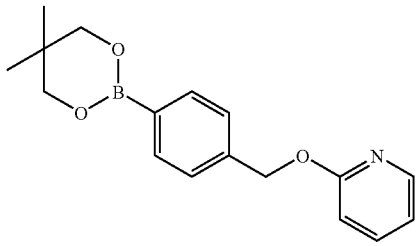

To a solution of 2-[(4-bromobenzyl)oxy]pyridine (789 g, 2.99 mol) in heptane (2603 g) were added heptane (939 mL) and tetrahydrofuran (1199 mL), which was cooled slowly with dry ice/ethanol bath under a nitrogen atmosphere, while stirring. After 45 minutes, cooling was stopped and 2-[(4-bromobenzyl)oxy]pyridine (0.9 g) was added thereto at an internal temperature of −12° C. Cooling was resumed, with cooling at −20° C./h. Approximately 3 hours later, 1.66M n-butyllithium hexane solution (1980 mL, 3.29 mol) was added thereto dropwise (80 min, −67.0 to 61.4° C.). After stirring for 0.5 hours, at the same temperature, triisopropoxy borane (674 g, 3.56 mol) was added thereto dropwise (134 min, −68.2 to 60.3° C.). At the same temperature, after stirring for 0.5 hours, switching to an ice water bath cooling, the solution was stirred overnight (external temperature: 0° C.). On the next day, water (5600 ml) was added thereto dropwise, the solution was transferred to a separator vessel and was extracted into the aqueous layer (pH: 11.2). Ethyl acetate (4800 mL) was added thereto and concentrated hydrochloric acid (approximately 280 mL) was added thereto dropwise (at an internal temperature of 20° C. or lower) while stirring, to adjust the solution to pH: 7.1. The organic layer was separated and washed with 5% sodium chloride water (approximately 900 g) and then concentrated under a reduced pressure. To the residue was added isopropyl alcohol (3300 mL), concentrated under a reduced pressure, isopropyl alcohol (3300 mL) was further added thereto and concentrated under a reduced pressure to obtain a solution of {4-[(pyridin-2-yloxy)methyl]phenyl}boronic acid (646 g) in isopropyl alcohol (2671 g) (yield: 94.4%). The obtained solution was heated to 60° C., which was added to a container containing 2,2-dimethyl-1,3-propanediol (354 g, 3.41 mol) while eliminating insoluble matter by suction-filtration, and then which was washed thereto down with isopropyl alcohol (685 mL). After confirming dissolution, the solution was stirred at a bath temperature of 20° C. and crystal precipitation was observed at an internal temperature of 28.8° C. After 1.5 hours, the bath temperature was set to −20° C., and the solution was stirred overnight. The precipitated crystal was filtered, and the crystal was washed with a small amount of isopropyl alcohol cooled to 0° C. The crystal was dried under a reduced pressure to obtain the title compound (779 g) as a white crystal (yield: 92.2%).

$^1$H-NMR Spectrum (DMSO-d$_6$) δ (ppm): 0.94 (6H, s), 3.74 (4H, s), 5.35 (2H, s), 6.87 (1H, d, J=8.4 Hz), 6.96-7.00 (1H, m), 7.39 (2H, d, J=8.0 Hz), 7.67-7.74 (3H, m), 8.14-8.17 (1H, m).

Reference Example 30

Synthesis of di-tert-butyl[3-(3-{4[(pyridin-2-yloxy)methyl]benzyl}isoxazol-5-yl)pyridin-2-yl]imidodicarbonate

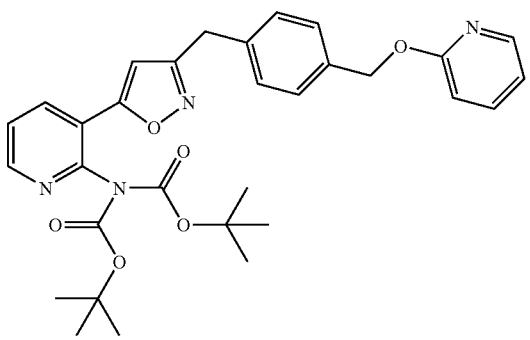

Under nitrogen atmosphere, to a mixture of di-tert-butyl{3-[3-(chloromethyl)isoxazol-5-yl]pyridin-2-yl}imidodicarbonate (164 mg, 0.40 mmol), {4-[(pyridin-2-yloxy)methyl]phenyl}boronic acid (138 mg, 0.60 mmol), cesium carbonate (391 mg, 1.20 mmol), copper(I) iodide (3.9 mg, 5 mol %) and 1,2-dimethoxyethane (2.0 mL) was added [1,1'-bis(diphenylphosphino)ferrocene]dichloropalladium(II) dichloromethane complex (16.4 mg, 5 mol %), which was stirred at 80° C. for 1.5 hours. {4-[(Pyridin-2-yloxy)methyl]phenyl}boronic acid (46 mg, 0.20 mmol) was added thereto and the solution was further stirred for 4.5 hours. After cooling, ethyl acetate and 5% sodium chloride solution were added thereto, insoluble matter was filtered out, then, the filtrate was transferred to a separatory funnel and separated. After the organic layer was washed with 5% sodium chloride water and dried over anhydrous magnesium sulfate, the solvent was evaporated under a reduced pressure. The residue was purified by silica gel column chromatography to obtain the title compound (173 mg) as a pale yellow oily product.

$^1$H-NMR Spectrum (CDCl$_3$) δ (ppm): 1.23 (9H, s), 4.05 (2H, s), 5.34 (2H, s), 6.32 (1H, s), 6.76-6.79 (1H, m), 6.86-6.90 (1H, m), 7.28 (2H, d, J=8.0 Hz), 7.38-7.43 (3H, m), 7.55-7.60 (1H, m), 8.15-8.18 (1H, m), 8.27 (1H, dd, J=2.0, 8.0 Hz), 8.57 (1H, dd, J=2.0, 7.6 Hz).

Reference Example 31

3-(3-(4-Pyridin-2-yloxymethyl)-benzyl)-isoxazol-5-yl)-pyridin-2-ylamine

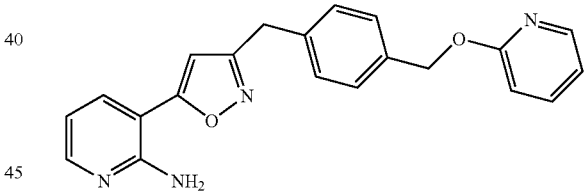

Di-tert-butyl[3-(3-{4[(pyridin-2-yloxy)methyl]benzyl}isoxazol-5-yl)pyridin-2-yl]imidodicarbonate (28.8 mg, 51.6 μmol) was dissolved in acetonitrile (0.6 mL), concentrated hydrochloric acid (60 μL, 690 μmol) was added thereto dropwise under an ice water cooling, which was stirred at the same temperature for one hour. Concentrated hydrochloric acid (140 μL, 1.61 mmol) was further added thereto dropwise and the solution was stirred at the same temperature for one hour and at 20° C. for 3.5 hours. Under an ice water cooling, to the reaction solution were added 0.5N aqueous sodium hydroxide and ethyl acetate and extracted. After the organic layer was washed with 5% sodium chloride water and dried over anhydrous magnesium sulfate, the solvent was evaporated under a reduced pressure to obtain the title compound (18.3 mg) as a pale yellow oily product.

$^1$H-NMR Spectrum (CDCl$_3$) δ (ppm): 4.07 (2H, s), 5.37 (2H, s), 5.42 (2H, brs), 6.25 (1H, s), 6.71 (1H, dd, J=5.2, 7.6 Hz), 6.80 (1H, d, J=8.4 Hz), 6.87-6.91 (1H, m), 7.30 (2H, d, J=7.6 Hz), 7.44 (2H, d, J=7.6 Hz), 7.56-7.61 (1H, m), 7.70 (1H, dd, J=2.0, 7.6 Hz), 8.14 (1H, dd, J=2.0, 4.8 Hz), 8.16-8.19 (1H, m).

Reference Examples 32 to 33 are other synthesis methods to Reference Examples 30 to 31.

Reference Example 32

Synthesis of di-tert-butyl[3-(3-{4[(pyridin-2-yloxy)methyl]benzyl}isoxazol-5-yl)pyridin-2-yl]imidodicarbonate

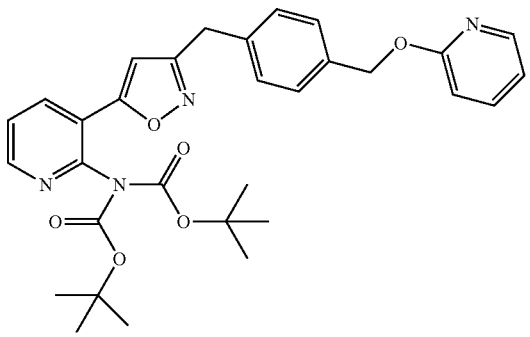

The operation of the first batch was carried out as described below. Under a nitrogen gas stream, after di-tert-butyl{3-[3-(chloromethyl)isoxazol-5-yl]pyridin-2-yl}imidodicarbonate (20.80 kg, 50.75 mol), 2-{[4-(5,5-dimethyl-1,3,2-dioxaborinan-2-yl)benzyl]oxy}pyridine (19.61 kg, 66.00 mol, 1.30M/M), (oxydi-2,1-phenylene)bis(diphenylphosphine) (1.367 kg, 2.54 mol, 0.05M/M), potassium carbonate (9.11 kg, 65.91 mol, 1.30M/M) were added to a 500 L reactor 2 which was nitrogen-substituted beforehand, the interior of the reactor was nitrogen-substituted again, N,N-dimethyl formamide (147 kg, 7.08 w/w) was added thereto and stirring was started. Then, after maintaining at an internal temperature of from 15 to 25° C. and a level of the reduced pressure of −0.090 MPa or greater for three to five minutes maintenance, the reduced pressure was released with nitrogen. This operation was repeated five times to degas the solution. After degassing was finished, solution of palladium acetate in N,N-dimethyl formamide (mixed solution of palladium acetate (0.570 kg, 2.54 mol, 0.05M/M) and degassed N,N-dimethyl formamide (9.8 kg, 0.5 w/w, a portion of which was set aside for thorough wash)) was added thereto, and washed thereto down with the set aside degassed N,N-dimethyl formamide. Next, after stirring for 10 minutes, immediately degassed water (10.4 kg, 0.5 w/w) was added thereto dropwise at an internal temperature of from 20 to 30° C., and the operation of reducing the pressure to −0.087 MPa level of the reduced pressure and releasing the reduced pressure with nitrogen was repeated three times. Thereafter, hot water at approximately 60° C. was circulated quickly to adjust the internal temperature to from 55 to 65° C. and the solution was stirred for three hours from the start of the heating. After the end of the reaction was confirmed by HPLC analysis, toluene (90 kg, 4.34 w/w) was added thereto at an internal temperature of from 0 to 25° C. and water (156 kg, 7.5 w/w) was added thereto dropwise at the same temperature range. Then, after stirring at an internal temperature of from 15 to 30° C. for 30 minutes, the solution was left standing still for 30 minutes or longer standing, and the lower layer was eliminated. To the upper layer inside of the reactor was added water (104 kg, 5.0 w/w), which was stirred at an internal temperature of from 15 to 30° C. for five minutes, then left standing still overnight, and only the lower layer containing no insoluble matter was eliminated. The upper layer and the lower layer containing insoluble matter were filtered with Celite 503 RV (2.8 kg, 0.135 w/w) under pressure by a filtration device, and the reactor and the filtration device were pour-washed with toluene (18.0 kg, 0.867 w/w, a portion was set aside for flushing and thorough washing). The obtained filtrate and washes were returned to the 500 L reactor 2 and washed thereto down with the previously set aside toluene. Subsequently, after the internal temperature was adjusted to 15 to 30° C., the solution was left standing still for 30 minutes or longer, and the lower layer was eliminated. After the stirring speed was adjusted to approximately maximum and n-heptane (152 kg, 7.32 w/w) was added thereto dropwise over one hour or longer at an internal temperature of from 15 to 30° C., the solution was stirred at the same temperature range for two hours or longer. Then, after thiocyanuric acid (0.90 kg, 5.08 mol, 0.1 M/M) was added thereto with divided fractions over 30 minutes or longer at an internal temperature of from 15 to 30° C., the solution was stirred at the same temperature range for one hour or longer. Once more, thiocyanuric acid (0.90 kg, 5.08 mol, 0.1M/M) was added thereto with divided fractions over 30 minutes or longer at an internal temperature of from 15 to 30° C. and the solution was stirred overnight at the same temperature range. After overnight stirring, the solution in the reactor was filtered with activated carbon by a filtration device which was prepared beforehand, and the reactor and the filtration device were washed thoroughly with a mixed solution of n-heptane-toluene (mixed solution of n-heptane (130 kg) and toluene (83 kg), a portion of which was set aside for wetting the activated carbon (Seisei Shirasagi)). After adding thiocyanuric acid (1.80 kg, 10.16 mol, 0.2M/M) thereinto once more, filtration with activated carbon was carried out using the same amount of Celite 503 RV, activated carbon (Seisei Shirasagi) and mixed solution of n-heptane-toluene. The obtained filtrate and washes were added to the 500 L reactor 1, which was concentrated under a reduced pressure and hot water circulation at 40 to 70° C. until the content solution was approximately 100 L visually. And, the residue was left standing still under a nitrogen atmosphere and at an internal temperature of 30° C. or lower until activated carbon filtration of the second batch was finished.

As a second batch, the same operation as described above was carried out. The filtrate and washes of the second batch were added to the 500 L reactor 1 to be pooled with the residue of the first batch, and concentration under a reduced pressure was started. Under hot water circulation at 60 to 70° C., when the distillate outflow had weakened, toluene (144 kg) was added thereto, then, again, under hot water circulation at 60 to 70° C., concentration under a reduced pressure was carried out until distillate outflow weakened. At this point, the residue was analyzed and the toluene/target product ratio (0.167 w/w) was calculated from the di-tert-butyl[3-(3-{4[(pyridin-2-yloxy)methyl]benzyl}isoxazol-5-yl)pyridin-2-yl]imido dicarbonate content and the toluene content in the concentration residue. Toluene (29.66 kg, corresponding to a toluene/target product ratio of 0.700 w/w) was added thereto, the solution was stirred at an internal temperature of from 15 to 30° C. for 30 minutes or longer to obtain a toluene solution of title compound (containing 42.37 kg of the target product; yield: 74.7%).

HPLC conditions: column: CAPCELL PAK C18 MGII (5 μm, 150×4.6 mmI.D., SHISEIDO), mobile phase: acetonitrile/water/trifluoroacetic acid=180/820/1 to 900/100/1 (v/v/v).

Reference Example 33

3-(3-(4-Pyridin-2-yloxymethyl)-benzyl)-isoxazol-5-yl)-pyridin-2-ylamine

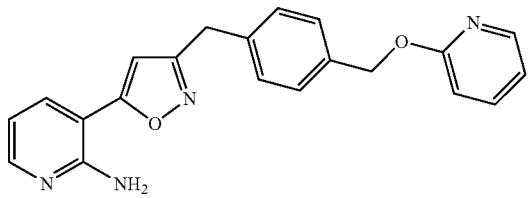

To a toluene solution of di-tert-butyl[3-(3-{4[(pyridin-2-yloxy)methyl]benzyl}isoxazol-5-yl)pyridin-2-yl]imido dicarbonate (containing 42.37 kg (75.85 mol)) was added formic acid (181 kg, 4.27 w/w) dropwise at an internal temperature of from −5 to 20° C., which was stirred at an internal temperature of from 22 to 32° C. for 19 to 20 hours. After the end of the reaction was confirmed by HPLC analysis, the internal temperature was cooled to −5 to 10° C. and the content solution was divided into two fractions and added to the 500 L reactors 1 and 2, respectively.

For the 500 L reactor 1, post-processing was carried out as described below. Under stirring, water (74 kg, 1.75 w/w) was added thereto dropwise at an internal temperature of from −5 to 20° C., further, tert-butylmethylether (31.4 kg, 0.74 w/w) and n-heptane (29.0 kg, 0.684 w/w) were added thereto at an internal temperature of from 0 to 25° C. The solution was stirred at an internal temperature of from 15 to 25° C. for five minutes, left standing still for 30 minutes or longer to separate the lower layer. The lower layer was returned to the reactor, tert-butylmethylether (31.4 kg, 0.74 w/w) and n-heptane (29.0 kg, 0.684 w/w) were added thereto again at an internal temperature of from 0 to 25° C., the solution was stirred at an internal temperature of from 15 to 25° C. for five minutes, then, left standing still for 30 minutes or longer, and the lower layer was separated again. The lower layer was returned to the reactor and, first, an aqueous solution of 48% sodium hydroxide (116 kg; 1392.0 mol, 18.35M/M as sodium hydroxide) was added dropwise at an internal temperature of from 0 to 25° C. Next, at the same temperature range, ethyl acetate (96 kg, 2.26 w/w) was added thereto and an aqueous solution of 48% sodium hydroxide (20.5 kg; 246.0 mol, 3.24M/M as sodium hydroxide) was added thereto dropwise. In addition, herein, at same temperature range, an aqueous solution of approximately 8% sodium hydroxide (mixed solution of an aqueous solution of 48% sodium hydroxide (12.7 kg; 152.4 mol, 2.00M/M as sodium hydroxide) and water (64 kg, 1.5 w/w)) was added thereto dropwise until a pH of the lower layer was pH 8.00 to 9.00, (actual value: pH 8.58) (0.75 kg used). Thereafter, the solution was stirred for one hour or longer at an internal temperature of from 20 to 30° C. and left standing still overnight, then, the pH of the lower layer was checked again (actual value: pH 8.29) and the lower layer was eliminated. To the upper layer remaining in the reactor was added an aqueous solution of approximately 5% sodium bicarbonate (mixed solution of sodium bicarbonate (5.3 kg, 63.09 mol) and water (101 kg, 2.375 w/w)), which was stirred at an internal temperature of from 20 to 30° C. for one hour or longer and then left standing still for 30 minutes or longer. After the lower layer (pH8.60) was eliminated, to the upper layer was added water (106 kg, 2.5 w/w), which was stirred at an internal temperature of from 20 to 30° C. for one hour or longer, then, left standing still for 30 minutes or longer, and the lower layer (pH7.17) was eliminated again.

For the 500 L reactor 2, the same post-processing was carried out concurrently with the 500 L reactor 1.

The content solution of the 500 L reactor 1 was transferred to the 500 L reactor 2 and concentrated under a reduced pressure under hot water circulation at 55 to 65° C. until the content solution was approximately 100 L. Next, to the concentration residue were added ethanol (45 kg, 1.0 w/w) and ethyl acetate (96 kg, 2.26 w/w), which was stirred for five minutes, then, concentrated under a reduced pressure under hot water circulation at 55 to 65° C. until a level of the reduced pressure of −0.092 MPa or greater and almost no distillate outflow was observed. At this point, as precipitation of crystal was observed, ethyl acetate was added little by little until the crystal dissolved completely (13.85 kg used). After ethanol (18.3 kg) and ethyl acetate (6.7 kg) were further added, the internal temperature was adjusted to 50 to 55° C., and after confirming visually that the crystal was dissolved, n-heptane (33.5 kg, 0.79 w/w) was added thereto over 30 minutes or longer at an internal temperature of from 45 to 55° C. Then, after 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136,279, Specifications, Example 18, was added thereto at an internal temperature of from 45 to 50° C. and precipitation of crystal was observed, the solution was stirred at the same temperature range for one hour or longer. After n-heptane (66.9 kg, 1.58 w/w) was added dropwise over one hour or longer at an internal temperature of from 45 to 55° C., the internal temperature was cooled to 0 to 10° C. over four hours or longer, and the solution was stirred at the same temperature range for five hours or longer. After the content solution was sampled and it was confirmed that the rate of crystallization of the target product was 94%, the suspension was filtered under pressure, the crystal was pour-washed in the order with mixed solution of ethanol-ethyl acetate-n-heptane (mixed solution of ethanol (3.60 kg, 0.085 w/w), ethyl acetate (4.15 kg, 0.098 w/w) and n-heptane (18.81 kg, 0.444 w/w)), and mixed solution of ethanol-n-heptane (mixed solution of ethanol (7.25 kg, 0.171 w/w) and n-heptane (18.81 kg, 0.444 w/w)) to obtain a wet crude crystal of the title compound (36.52 kg) as a slightly yellow crystal.

The obtained wet crude crystal of 3-(3-(4-pyridin-2-yloxymethyl)-benzyl)-isoxazol-5-yl)-pyridin-2-ylamine (36.52 kg) and ethanol (57.9 kg, 2.37 w/w) were added sequentially to a 500 L dissolution can, which was nitrogen-substituted beforehand, and heated to an internal temperature of from 70 to 75° C. to dissolve the crystal. While maintaining the temperature, this dissolution solution was transferred through a SUS filter to a 500 L crystallization can, and the 500 L dissolution can and SUS filter were washed thoughtly with ethanol (19.3 kg, 0.8 w/w) which was kept heated at an external temperature of approximately 65° C. Next, the filtrate was adjusted to an internal temperature of from 55 to 60° C., and it was confirmed that the solution inside the can was homogenous. Thereafter, when the internal temperature was cooled slowly to 48 to 51° C., crystal precipitated. After heating again to an internal temperature of from 55 to 60° C. to dissolve the crystal, immediately the internal temperature was cooled to 48 to 51° C. and 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136,279, Specifications, Example 18, was added immediately. Then, after precipitation of crystal was confirmed visually at an internal temperature of from 45 to 50° C., the suspension was stirred at an internal temperature of from 43 to 47° C. for one hour to one hour and 30 minutes, and the internal temperature was cooled to 0 to 10° C. over four hours or longer. At this point, after a precipitated crystal was sampled and the crystal form thereof was confirmed to be identical to the reference sample, the suspension was stirred overnight at the same temperature range. On the next day, after the crystal form was confirmed to be identical to the reference sample, the crystal was solid-liquid separated with a centrifuge divided in two times, and respectively pour-washed with approximately half of the amount of 19.3 kg of ethanol to obtain a wet crystal of the target product (24.23 kg). This wet crystal was placed into a mixed type vacuum dryer and dried under a reduced pressure at an external temperature of from 20 to 30° C. for 6 hours or longer and an external temperature of from 35 to 45° C. for 12 hours or longer to obtain the title compound (23.52 kg, 65.63 mol, yield: 86.8%) as a pale yellow crystal.

$^1$H-NMR Spectrum (CDCl$_3$) δ (ppm): 4.07 (2H, s), 5.37 (2H, s), 5.42 (2H, brs), 6.25 (1H, s), 6.71 (1H, dd, J=5.2, 7.6 Hz), 6.80 (1H, d, J=8.4 Hz), 6.87-6.91 (1H, m), 7.30 (2H, d, J=7.6 Hz), 7.44 (2H, d, J=7.6 Hz), 7.56-7.61 (1H, m), 7.70 (1H, dd, J=2.0, 7.6 Hz), 8.14 (1H, dd, J=2.0, 4.8 Hz), 8.16-8.19 (1H, m).

HPLC conditions: column: CAPCELL PAK C18 MGII (5 μm, 150×4.6 mmI.D., SHISEIDO), mobile phase: acetonitrile/water/trifluoroacetic acid=180/820/1 to 900/100/1 (v/v/v).

Example 1

(S)-2-Amino-4-(3-(3-(4-(pyridin-2-yloxymethyl)-benzyl)-isoxazol-5-yl)-pyridin-2-ylcarbamoyl)-butyric acid

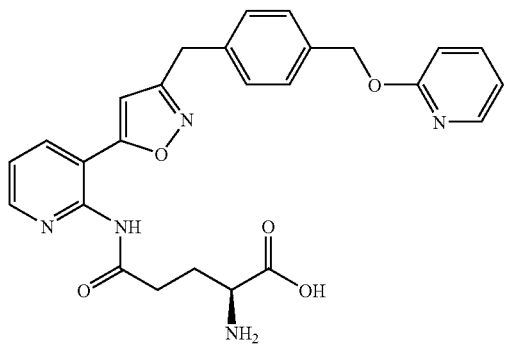

To a mixture of (S)-2-tert-butoxycarbonylamino-4-(3-(3-(4-(pyridin-2-yloxymethyl)-benzyl)-isoxazol-5-yl)-pyridin-2-ylcarbamoyl)-butyric acid tert-butyl ester (980 mg, 1.5 mmol) described in Manufacturing Example 1-1 and dichloromethane (10 mL) was added trifluoroacetic acid (10 mL) at 0° C., which was stirred overnight at room temperature. The solvent was evaporated under a reduced pressure, and the residue was washed with diethyl ether, so as to obtain the titled compound (850 mg) as the trifluoroacetic acid salt.

$^1$H-NMR Spectrum (DMSO-d$_6$) δ (ppm): 1.91-2.05 (2H, m), 2.44-2.57 (2H, m), 3.91 (1H, brs), 4.03 (2H, s), 5.32 (2H, s), 6.66 (1H, s), 6.84-6.87 (1H, m), 6.98-7.01 (1H, m), 7.31 (2H, d, J=8.1 Hz), 7.40-7.44 (3H, m), 7.70-7.75 (1H, m), 8.16-8.18 (2H, m), 8.26 (3H, brs), 8.52 (1H, dd, J=1.8, 4.7 Hz), 10.49 (1H, s).

The starting substance (S)-2-tert-butoxycarbonylamino-4-(3-(3-(4-(pyridin-2-yloxymethyl)-benzyl)-isoxazol-5-yl)-pyridin-2-ylcarbamoyl)-butyric acid tert-butyl ester was synthesized by the following method.

Manufacturing Example 1-1

(S)-2-tert-Butoxycarbonylamino-4-(3-(3-(4-(pyridin-2-yloxymethyl)-benzyl)-isoxazol-5-yl)-pyridin-2-ylcarbamoyl)-butyric acid tert-butyl ester

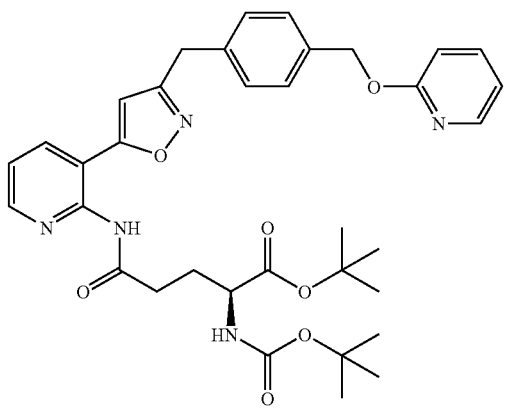

To a solution of 3-(3-(4-(pyridin-2-yloxymethyl)-benzyl)-isoxazol-5-yl)-pyridin-2-ylamine (900 mg, 2.5 mmol) described in Reference Example 1 in acetonitrile (15 mL) were added (S)-2-tert-butoxycarbonylamino-pentanedioic acid 1-tert-butyl ester (860 mg, 2.8 mmol), triethylamine (0.37 mL, 2.6 mmol), and O-(7-azabenzotriazol-1-yl)-N,N,N',N'-tetramethyl-uronium hexafluorophosphate (1.1 g, 2.8 mmol) at 0° C., which was stirred overnight at 60° C. Water and ethyl acetate were added to the reaction solution, and the organic layer was washed with saturated brine. The residue thus obtained was purified by NH silica gel column chromatography (heptane:ethyl acetate=4:1), so as to obtain the titled compound (980 mg).

$^1$H-NMR Spectrum (CDCl$_3$) δ (ppm): 1.42 (9H, s), 1.46 (9H, s), 1.95 (1H, brs), 2.23 (1H, brs), 2.64-2.66 (2H, m), 4.08 (2H, s), 4.23 (1H, brs), 5.27 (1H, d, J=7.1 Hz), 5.36 (2H, s), 6.33 (1H, s), 6.71-6.81 (1H, m), 6.87-6.90 (1H, m), 7.18 (1H, dd, J=4.7, 7.8 Hz), 7.30 (2H, d, J=8.1 Hz), 7.44 (2H, d, J=8.1 Hz), 7.56-7.61 (1H, m), 7.93 (1H, d, J=7.9 Hz), 8.16-8.18 (1H, m), 8.47-8.48 (1H, m), 8.52 (1H, brs).

Example 2

(S)-2-Amino-4-(3-{-[4-(pyridin-2-yloxymethyl)-benzyl]soxazol-5-yl}-pyridin-2-ylcarbamoyl)-butyric acid methyl ester

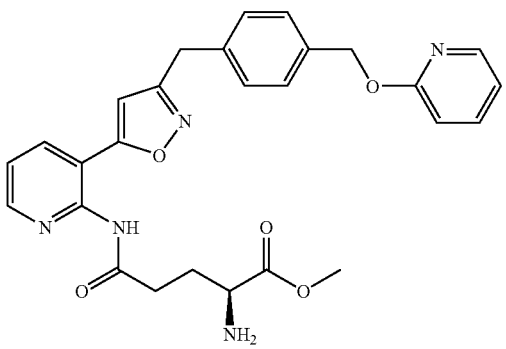

To a mixture of (S)-2-tert-butoxycarbonylamino-4-(3-{3-[4-(pyridin-2-yloxymethyl)-benzyl]-isoxazol-5-yl}-pyridin-2-ylcarbamoyl)-butyric acid methyl ester (31 mg, 0.052 mmol) described in Manufacturing Example 2-2 and dichloromethane (1 mL) was added trifluoroacetic acid (0.5 mL) at room temperature, which was stirred overnight at the same temperature. The solvent was evaporated from the reaction mixture under a reduced pressure, and the residue thus obtained was washed with diethyl ether, so as to obtain the titled compound (26 mg) as the trifluoroacetic acid salt.

$^1$H-NMR Spectrum (DMSO-$d_6$) δ (ppm): 1.97-2.03 (2H, m), 2.43-2.53 (2H, m), 3.74 (3H, s), 4.04-4.05 (3H, m), 5.32 (2H, s), 6.66 (1H, s), 6.84-6.87 (1H, m), 6.98-7.01 (1H, m), 7.31 (2H, d, J=8.2 Hz), 7.41 (2H, d, J=8.1 Hz), 7.43 (1H, d, J=7.9 Hz), 7.70-7.75 (1H, m), 8.16 (1H, d, J=1.8 Hz), 8.18 (1H, t, J=1.8 Hz), 8.38 (3H, brs), 8.52 (1H, dd, J=1.8, 4.8 Hz), 10.47 (1H, s).

The starting substance (S)-2-tert-butoxycarbonylamino-4-(3-{3-[4-(pyridin-2-yloxymethyl)-benzyl]-isoxazol-5-yl}-pyridin-2-ylcarbamoyl)-butyric acid methyl ester was synthesized by the following method.

Manufacturing Example 2-1

(S)-2-tert-Butoxycarbonylamino-pentanedioic acid 5-benzyl ester 1-methyl ester

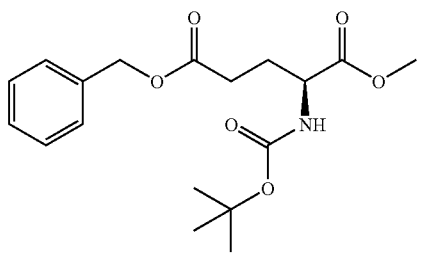

To a mixture of (S)-2-tert-butoxycarbonylamino-pentanedioic acid 5-benzyl ester (300 mg, 0.89 mmol) and methanol (4 mL) were added benzotriazol-1-yloxytris-(dimethylamino)-phosphonium hexafluorophosphate (390 mg, 0.89 mmol), N-methylmorpholine (98 μL, 0.89 mmol), and acetonitrile (1 mL) at 0° C., which was stirred overnight at room temperature. A 1N sodium hydroxide aqueous solution was added to the reaction mixture, which was extracted with ethyl acetate. The organic layer was washed first with water and then with saturated brine, and dried over anhydrous magnesium sulfate. The solvent was evaporated under a reduced pressure, so as to obtain the titled compound (380 mg, purity of 66%) in a crude form.

$^1$H-NMR Spectrum (CDCl$_3$) δ (ppm): 1.43 (9H, s), 1.92-2.01 (1H, m), 2.18-2.23 (1H, m), 2.39-2.51 (2H, m), 3.73 (3H, s), 4.34-4.36 (1H, m), 5.10-5.12 (3H, m), 7.31-7.39 (5H, m).

Manufacturing Example 2-2

(S)-2-tert-Butoxycarbonylamino-4-(3-{3-[4-(pyridin-2-yloxymethyl)-benzyl]-isoxazol-5-yl}-pyridin-2-ylcarbamoyl)-butyric acid methyl ester

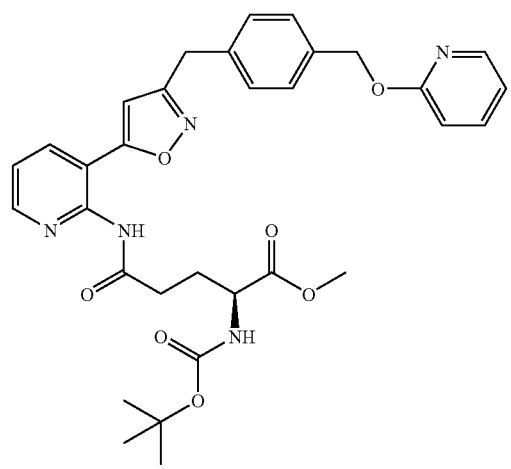

To a mixture of (S)-2-tert-butoxycarbonylamino-pentanedioic acid 5-benzyl ester 1-methyl ester (370 mg, 0.70 mmol; 66% purity) described in Manufacturing Example 2-1 and methanol (4 mL) was added palladium-carbon (40 mg, 0.19 mmol; 50% water content) at room temperature, which was stirred for 5 hours at room temperature under a hydrogen atmosphere (1 atm). The reaction mixture was replaced with nitrogen and filtered through a Celite pad. The solvent was evaporated from the filtrate under a reduced pressure, so as to obtain (S)-2-tert-butoxycarbonylamino-pentanedioic acid 1-methyl ester (300 mg) in a crude form. The crude product thus obtained was used directly in the next reaction. To a mixture of 3-(3-(4-(pyridin-2-yloxymethyl)-benzyl)-isoxazol-5-yl)-pyridin-2-ylamine (150 mg, 0.42 mmol) described in Reference Example 1 and acetonitrile (3 mL) were added (S)-2-tert-butoxycarbonylamino-pentanedioic acid 1-methyl ester (crude, 220 mg), N-methylmorpholine (46 μL, 0.42 mmol), and O-(7-azabenzotriazol-1-yl)-1,1,3,3-tetramethyluronium hexafluorophosphate (180 mg, 0.46 mmol) in this order at 0° C., which was stirrer overnight at room temperature. Water was added to the reaction mixture, which was extracted with ethyl acetate. The organic layer was washed with saturated brine, and the solvent was evaporated under a reduced pressure. The residue was purified by NH silica gel column chromatography (ethyl acetate:heptane=4:1), so as to obtain the titled compound (37 mg).

$^1$H-NMR Spectrum (CDCl$_3$) δ (ppm): 1.42 (9H, s), 1.97-2.04 (1H, m), 2.22-2.31 (1H, m), 2.67-2.70 (2H, m), 3.73 (3H, s), 4.08 (2H, s), 4.36-4.37 (1H, m), 5.34-5.36 (3H, m), 6.34 (1H, s), 6.79-6.81 (1H, m), 6.87-6.90 (1H, m), 7.18 (1H, dd, J=4.8, 7.9 Hz), 7.30 (2H, d, J=8.1 Hz), 7.44 (2H, d, J=8.1 Hz), 7.56-7.61 (1H, m), 7.94 (1H, dd, J=1.8, 7.8 Hz), 8.16-8.18 (1H, m), 8.47-8.48 (2H, m).

Example 3

(S)-2-Amino-4-(3-{3-[4-(pyridin-2-yloxymethyl)-benzyl]-isoxazol-5-yl}-pyridin-2-ylcarbamoyl)-butyric acid 2-dimethylamino-ethyl ester

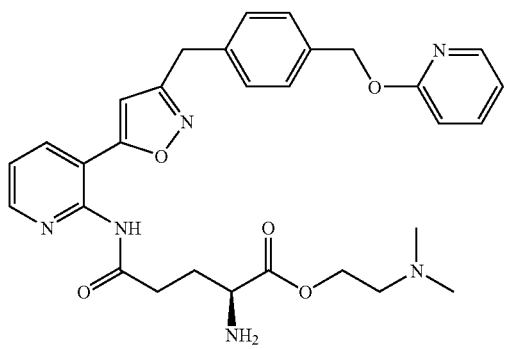

To a mixture of (S)-2-tert-butoxycarbonylamino-4-(3-{3-[4-(pyridin-2-yloxymethyl)-benzyl]-isoxazol-5-yl}-pyridin-2-ylcarbamoyl)-butyric acid 2-dimethylamino-ethyl ester (53 mg, 0.060 mmol; purity of 75%) described in Manufacturing Example 3-2 and dichloromethane (1 mL) was added trifluoroacetic acid (0.5 mL) at room temperature, which was stirred overnight at the same temperature. The solvent was evaporated from the reaction mixture under a reduced pressure, and the residue thus obtained was washed with diethyl ether, so as to obtain the titled compound (46 mg) as di-(trifluoroacetic acid) salt.

$^1$H-NMR Spectrum (DMSO-$d_6$) δ (ppm): 2.06 (2H, brs), 2.49-2.54 (2H, m), 2.84 (6H, s), 3.44 (2H, brs), 4.04-4.08 (3H, m), 4.44-4.47 (2H, m), 5.32 (2H, s), 6.69 (1H, s), 6.85 (1H, dd, J=0.7, 8.4 Hz), 6.98-7.01 (1H, m), 7.31 (2H, d, J=8.1 Hz), 7.41-7.45 (3H, m), 7.70-7.75 (1H, m), 8.16-8.19 (2H, m), 8.52-8.53 (4H, m), 10.48 (1H, s).

The starting substance (S)-2-tert-butoxycarbonylamino-4-(3-[(3-{4-(pyridin-2-yloxymethyl)-benzyl]-isoxazol-5-yl}-pyridin-2-ylcarbamoyl)-butyric acid 2-dimethylamino-ethyl ester was synthesized by the following method.

Manfacturing Example 3-1

(S)-2-tert-butoxycarbonylamino-pentanedioic acid 5-benzyl ester 1-(2-dimethylamino-ethyl)ester

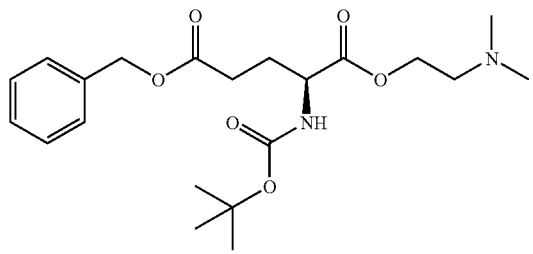

To a mixture of (S)-2-tert-butoxycarbonylamino-pentanedioic acid 5-benzyl ester (300 mg, 0.89 mmol) and acetonitrile (5 mL) were added 2-dimethylaminoethanol (89 μL, 0.89 mmol) and benzotriazol-1-yloxytris-(dimethylamino)-phosphonium hexafluorophosphate (390 mg, 0.89 mmol) at 0° C., which was stirred overnight at room temperature. A 1N sodium hydroxide aqueous solution was added to the reaction mixture, which was extracted with ethyl acetate. The organic layer was washed first with water and then with saturated brine, and dried over anhydrous magnesium sulfate. The solvent was evaporated under a reduced pressure, so s to obtain the titled compound (380 mg, purity of 77%).

$^1$H-NMR Spectrum (CDCl$_3$) δ (ppm): 1.43 (9H, s), 1.94-2.03 (1H, m), 2.18-2.25 (1H, m), 2.28 (6H, s), 2.41-2.55 (2H, m), 2.59 (2H, t, J=5.8 Hz), 4.23-4.26 (2H, m), 4.34-4.36 (1H, m), 5.12 (2H, s), 5.16-5.18 (1H, m), 7.32-7.38 (5H, m).

Manufacturing Example 3-2

(S)-2-tert-Butoxycarbonylamino-4-(3-{3-[4-(pyridin-2-yloxymethyl)-benzyl]-isoxazol-5-yl}-pyridin-2-ylcarbamoyl)-butyric acid 2-dimethylamino-ethyl ester

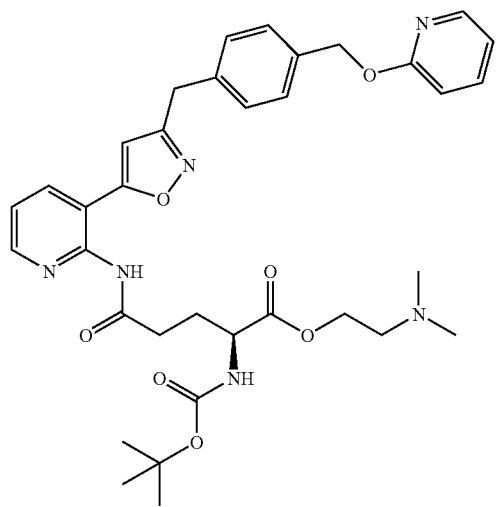

To a mixture of (S)-2-tert-butoxycarbonylamino-pentanedioic acid 5-benzyl ester 1-(2-dimethylamino-ethyl)ester (370 mg, 0.70 mmol; 77% purity) described in Manufacturing Example 3-1 and ethanol (4 mL) was added palladium-carbon (40 mg, 0.19 mmol; 50% water content) at room temperature, which was stirred overnight at room temperature under a hydrogen atmosphere (1 atm). The reaction mixture was replaced with nitrogen and filtered through a Celite pad. The solvent was evaporated under a reduced pressure, so as to obtain (S)-2-tert-butoxycarbonylamino-pentanedioic acid 1-(2-dimethylamino-ethyl)ester (300 mg) in a crude form. The crude product thus obtained was used directly in the next reaction. To a mixture of 3-(3-(4-(pyridin-2-yloxymethyl)-benzyl)-isoxazol-5-yl)-pyridin-2-ylamine (150 mg, 0.42 mmol) described in Reference Example 1 and acetonitrile (3 mL) were added (S)-2-tert-butoxycarbonylamino-pentanedioic acid 1-(2-dimethylamino-ethyl)ester (crude, 190 mg) and O-(7-azabenzotriazol-1-yl)-1,1,3,3-tetramethyl-uronium hexafluorophosphate (160 mg, 0.42 mmol) in this order at 0° C., which was stirred overnight at room temperature. Water was added to the reaction mixture, which was extracted with ethyl acetate. The organic layer was washed with saturated brine, and the solvent was evaporated under a reduced pressure. The residue was purified by NH silica gel column chromatography (ethyl acetate:methanol=30:1), so as to obtain the titled compound (56 mg, purity of 75%).

$^1$H-NMR Spectrum (CDCl$_3$) δ(ppm): 1.41 (9H, s), 2.12-2.14 (2H, m), 2.20 (6H, s), 2.46-2.60 (4H, m), 4.08-4.13 (3H, m), 4.31-4.37 (2H, m), 5.31-5.36 (3H, m), 6.37 (1H, s), 6.78-6.81 (1H, m), 6.87-6.90 (1H, m), 7.21 (1H, dd, J=4.8, 7.9 Hz), 7.30 (2H, d, J=7.9 Hz), 7.43 (2H, d, J=8.2 Hz), 7.56-7.61 (1H, m), 7.98 (1H, d, J=7.7 Hz), 8.16-8.18 (1H, m), 8.48 (1H, dd, J=1.8, 4.8 Hz), 9.29 (1H, brs).

Example 4

(S)-2-Amino-4-(3-{3-[4-(pyridin-2-yloxymethyl)-benzyl]-isoxazl-5-yl}-pyridin-2-ylcarbamoyl)-butyric acid ethyl ester

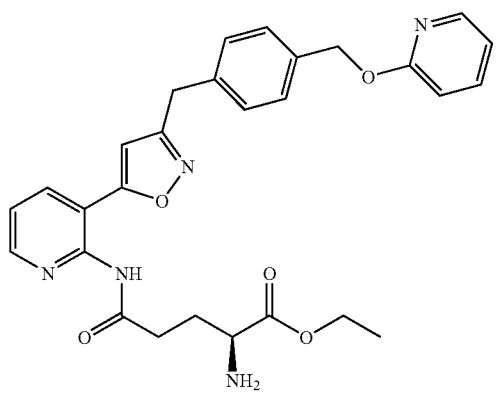

To a mixture of (S)-2-tert-butoxycarbonylamino-4-(3-{3-[4-(pyridin-2-yloxymethyl)-benzyl]-isoxazol-5-yl}-pyridin-2-ylcarbamoyl)-butyric acid ethyl ester (40 mg, 0.065 mmol) described in Manufacturing Example 4-2 and dichloromethane (1 mL) was added trifluoroacetic acid (0.5 mL) at room temperature, which was stirred overnight at the same temperature. The solvent was evaporated from the reaction mixture under a reduced pressure, and the residue thus obtained was washed with diethyl ether, so as to obtain the titled compound (30 mg) as the trifluoroacetic acid salt.

$^1$H-NMR Spectrum (DMSO-d$_6$) δ (ppm): 1.24 (3H, t, J=7.1 Hz), 1.97-2.03 (2H, m), 2.41-2.56 (2H, m), 4.01-4.03 (3H, m), 4.21 (2H, q, J=7.1 Hz), 5.32 (2H, s), 6.66 (1H, s), 6.84-6.86 (1H, m), 6.98-7.01 (1H, m), 7.30 (2H, d, J=8.2 Hz), 7.41 (2H, d, J=8.1 Hz), 7.43 (1H, d, J=7.7 Hz), 7.70-7.75 (1H, m), 8.16-8.18 (2H, m), 8.38 (3H, brs), 8.52 (1H, dd, J=1.8, 4.8 Hz), 10.48 (1H, s).

The starting substance (S)-2-tert-butoxycarbonylamino-4-(3-{3-[4-(pyridin-2-yloxymethyl)-benzyl]-isoxazol-5-yl}-pyridin-2-ylcarbamoyl)-butyric acid ethyl ester was synthesized by the following method.

Manufacturing Example 4-1

(S)-2-tert-butoxycarbonylamino-pentanedioic acid 5-benzyl ester 1-ethyl ester

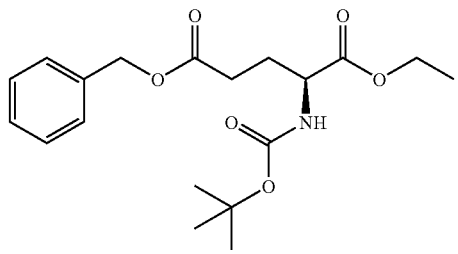

To a mixture of (S)-2-tert-butoxycarbonylamino-pentanedioic acid 5-benzyl ester (300 mg, 0.89 mmol) and methanol (4 mL) were added N-methylmorpholine (98 μL, 0.89 mmol), benzotriazol-1-yloxytris-(dimethylamino)-phosphonium hexafluorophosphate (390 mg, 0.89 mmol), and acetonitrile (2 mL) at 0° C., which was stirred overnight at room temperature. A 1N sodium hydroxide aqueous solution was added to the reaction mixture, which was extracted with ethyl acetate. The organic layer was washed first with water and then with saturated brine, and dried over anhydrous magnesium sulfate. The solvent was evaporated under a reduced pressure, so as to obtain the titled compound (410 mg, purity of 63%) in a crude form.

$^1$H-NMR Spectrum (CDCl$_3$) δ (ppm): 1.27 (3H, t, J=7.1 Hz), 1.44 (9H, s), 1.91-2.01 (1H, m), 2.18-2.21 (1H, m), 2.39-2.52 (2H, m), 4.16-4.22 (2H, m), 4.32-4.33 (1H, m), 5.10-5.12 (3H, m), 7.31-7.39 (5H, m).

Manufacturing Example 4-2

(S)-2-tert-Butoxycarbonylamino-4-(3-{3-[4-(pyridin-2-yloxymethyl)-benzyl]-isoxazol-5-yl}-pyridin-2-ylcarbamoyl)-butyric acid ethyl ester

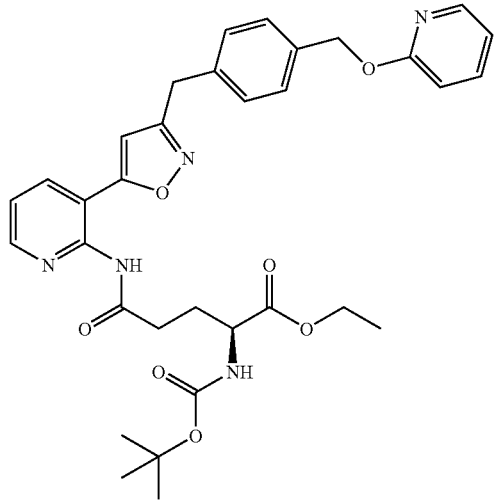

To a mixture of (S)-2-tert-butoxycarbonylamino-pentanedioic acid 5-benzyl ester 1-ethyl ester (390 mg, 0.67 mmol; 63% purity) described in Manufacturing Example 4-1 and ethanol (4 mL) was added palladium-carbon (40 mg, 0.19 mmol; 50% water content) at room temperature, which was stirred overnight under a hydrogen atmosphere (1 atm) at room temperature. The reaction mixture was replaced with nitrogen and filtered through a Celite pad. The solvent was evaporated from the filtrate under a reduced pressure, so as to obtain (S)-2-tert-butoxycarbonylamino-pentanedioic acid 1-ethyl ester (330 mg) in a crude form. The crude product thus obtained was used directly in the next reaction. To a mixture of 3-(3-(4-(pyridin-2-yloxymethyl)-benzyl)-isoxazol-5-yl)-pyridin-2-ylamine (150 mg, 80.42 mmol) described in Reference Example 1 and acetonitrile (3 mL) were added (S)-2-tert-butoxycarbonylamino-pentanedioic acid 1-ethyl ester (crude, 230 mg), N-methylmorpholine (46 μL, 0.42 mmol), and 180 mg (0.46 mmol) of 047-azabenzotriazol-1-yl)-1,1,3,3-tetramethyl-uronium hexafluorophosphate (180 mg, 0.46 mmol) were added in this order at 0° C., which was stirred overnight at room temperature. Water was added to the reaction mixture, which was extracted with ethyl acetate. The organic layer was washed with saturated brine, and the solvent was evaporated under a reduced pressure. The residue was purified by NH silica gel column chromatography (ethyl acetate:heptane=4:1), so as to obtain the titled compound (47 mg).

$^1$H-NMR Spectrum (CDCl$_3$) δ (ppm): 1.27 (3H, t, J=7.1 Hz), 1.42 (9H, s), 1.94-2.05 (1H, m), 2.23-2.31 (1H, m), 2.64-2.72 (2H, m), 4.08 (2H, s), 4.19 (2H, q, J=7.1 Hz), 4.33-4.34 (1H, m), 5.33-5.36 (3H, m), 6.33 (1H, s), 6.79-6.81 (1H, m), 6.87-6.90 (1H, m), 7.18 (1H, dd, J=4.9, 7.8 Hz), 7.30 (2H, d, J=8.1 Hz), 7.44 (2H, d, J=8.2 Hz), 7.56-7.61 (1H, m), 7.92-7.95 (1H, m), 8.17 (1H, ddd, J=0.7, 2.0, 5.1 Hz), 8.47 (1H, dd, J=1.8, 4.8 Hz), 8.51 (1H, brs).

The compounds according to the present invention represented by formula (I) were used in a Candida systemic infection experiment with mice, which showed that there was pronounced improvement in the average number of survival days, and that the properties were excellent, especially in terms of solubility in water and stability in aqueous solutions, as well as safety and pharmacokinetics, demonstrating that these compounds are extremely useful for the prevention or treatment of fungal infections.

[Comparative Test Example of Solubility in Water]

3-(3-(4-(Pyridin-2-yloxymethyl)-benzyl)-isoxazol-5-yl)-pyridin-2-ylamine described in Reference Example 1, which is the parent compound, and the compounds of Example 1 to 3 were compared for solubility and stability in solution in a Britton-Robinson buffer (ionic strength: 0.3) at 25° C. Table 1 shows the results.

TABLE 1

|  | Solubility (mg/mL) | | Stability in solution (remainder (%) after 24 h in dark place) | |
| --- | --- | --- | --- | --- |
|  | pH 3 | pH 7 | pH 3 | pH 7 |
| Parent compound | 0.29 | 0.001 | 90 (pH 2) 99 (pH 4) | 95 |
| Compound of Ex. 1 | 1.1 | 0.3 | 96 | 92 |
| Compound of Ex. 2 | 45 | 0.2 | 88 | 44 |
| Compound of Ex. 3 | 12 | 1.1 | 116 | 82 |

As can be clear from the results in Table 1, the compounds of Examples 1, 2, and 3 have higher solubility in water than does the parent compound.

Pharmacokinetic Evaluation in Mice

1. Pharmacokinetic Evaluation of Compound of Example 1 in Mice (1) Preparation of Administration Solution The compound of Example 1 was dissolved in a concentration of 0.3 mg/mL with 5% glucose (Otsuka Pharmaceutical) containing a 10 mM hydrochloric acid solution (Wako Pure Chemicals), and the active form as a parent compound was dissolved in a concentration of 0.3 mg/mL in 5% glucose (Otsuka Pharmaceutical) containing a 3 mM hydrochloric acid solution (Wako Pure Chemicals).

(2) Administration, and Sampling of Blood and Plasma

Using five-week-old female ICR mice (Charles River Japan), the compound of Example 1 and the active form thereof were administered into the tail vein in a dose of 3 mg/kg, with two mice per group for the compound of Example 1 and with three mice per group for the active form. The tail vein was punctured 30 minutes and 1, 3, 5, and 8 hours after administration of the compound of Example 1, and 5 minutes, 15 minutes, 30 minutes, and 1, 2, 4, 6, and 8 hours after administration of the active form, and blood was collected with a heparin-treated pipette. The blood samples were put in sampling tubes and stored under ice cooling, after which they were centrifuged for 5 minutes at 10,500×g and at 4° C. The plasma thus obtained was accurately divided into 10 μL amounts and stored at −20° C. until they were analyzed.

(3) Plasma Concentration Measurement Method

The plasma concentrations of the compound of Example 1 and the active form thereof were measured using a liquid chromatography mass spectrometer (LC-MS/MS: Waters, Quattro Ultima Pt), and quantified by internal standard method. Imipramine hydrochloride (Sigma) was dissolved in a mixed solution of acetonitrile and methanol (1:1) so that the concentration would be 0.1 μmol/L, to prepare an internal standard substance solution (IS solution). The plasma was melted, after which 100 μL of IS solution was added thereto and mixed while still cooled with ice, and this was centrifuged (deproteinated) for 10 minutes at 7800×g and at 4° C., after which the supernatant was centrifugally filtered through a membrane filter (Millipore: MultiScreen™) and analyzed by LC-MS/MS (Waters, Quattro Ultima Pt). In the chromatogram thus obtained, the surface area of the peaks for the compound of Example 1, the active form thereof (the parent compound of the compound of Example 1), and the internal standard substance were analyzed with analytic software (Waters: MassLynx 4.0), and the concentration of the compound included in the plasma was calculated by internal standard method. The active form concentration after administration of the compound of Example 1 was corrected with the molecular weight ratio, that is, the value of (the molecular weight of the compound of Example 1)/(the molecular weight of the active form).

The plasma concentration was measured for the compound of Example 1 and the active form by the method described in section 1. As a result, as shown in FIG. 1, the plasma concentration of the compound of Example 1 decreased quickly after administration, and the plasma concentration of the active form increased quickly from immediately after administration of the compound of Example 1, exhibiting a plasma concentration change that was similar to that at the time of active form administration. The above suggests that the compound of Example 1 is rapidly converted into the active form in the bodies of the mice.

2. Pharmacokinetic Evaluation of Compound of Examples 2 and 3 in Mice (1) Preparation of Administration Solution The compounds of Examples 2 and 3 were dissolved in respective concentrations of 1 and 1.5 mg/mL with 5% glucose (Otsuka Pharmaceutical) containing a 10 mM hydrochloric acid solution (Wako Pure Chemicals), and the active form was dissolved in a concentration of 0.5 mg/mL in 5% glucose (Otsuka Pharmaceutical) containing a 10 mM hydrochloric acid solution (Wako Pure Chemicals).

(2) Administration, and Sampling of Blood and Plasma

Using seven-week-old female ICR mice (Charles River Japan), with two mice per group, the compound of the present invention and the active form thereof were administered into the tail vein in a dose of 3 mg/kg, calculated as an active form equivalent. The tail vein was punctured 20 minutes, 45 minutes, and 1.5, 3, 5, and 8 hours after administration, and blood was collected with a heparin-treated pipette. The blood samples were put in sampling tubes and stored under ice cooling, after which they were centrifuged for 5 minutes at 10,500×g and at 4° C. The plasma thus obtained was accurately divided into 5 µL amounts and stored at −20° C. until they were analyzed.

(3) Plasma Concentration Measurement Method

The plasma concentrations of the compounds of Examples 2 and 3 and the active form thereof were measured using a liquid chromatography mass spectrometer (LC-MS: Waters, ZQ mass detector), and quantified by internal standard method. Imipramine hydrochloride (Sigma) was dissolved in a mixed solution of acetonitrile and methanol (9:1) so that the concentration would be 1 µmol/L, to prepare an internal standard substance solution (IS solution). The plasma was melted, after which 50 µL of IS solution was added thereto and mixed while still cooled with ice, and this was centrifuged (deproteinated) for 10 minutes at 1607×g and at 4° C., after which the supernatant was analyzed by LC-MS (Waters, ZQ mass detector). In the chromatogram thus obtained, the surface area of the peaks for the compounds of Examples 2 and 3, the active form thereof, and the internal standard substance were analyzed with analytic software (Waters: MassLynx 4.0), and the concentration of the compound included in the plasma was calculated by internal standard method.

Figure 2:
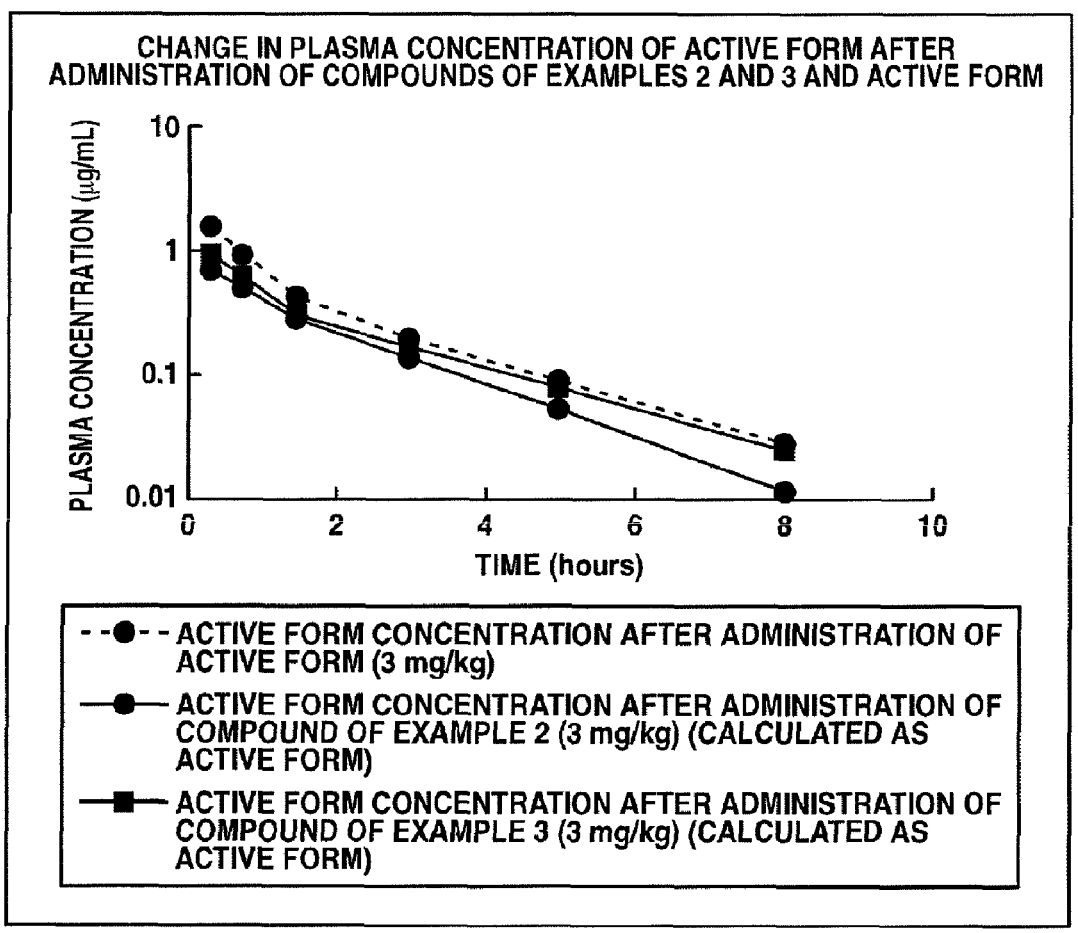
FIG. 2 shows the results of measuring the plasma concentration of the compound of Examples 2 and 3 and the active forms, which are parent compounds of the compound of Examples 2 and 3, measured by pharmacokinetic evaluation in mice in one embodiment of the present invention.

The concentrations of the compounds of Examples 2 and 3 and the active form thereof in plasma were calculated by the method discussed in section 2 above. As a result, as shown in FIG. 2, the compounds of Examples 2 and 3 were not detected. Meanwhile, the concentration of the active form in plasma rose sharply after administration of the compounds of Examples 2 and 3, exhibiting a transition to an in-plasma concentration similar to that at the time of active form administration. This suggests that the compounds of Examples 2 and 3 are rapidly converted into the active form in the bodies of the mice.

INDUSTRIAL APPLICABILITY

According to the present invention, the compounds of the present invention represented by formula 1) acts against the onset, development and persistence of infections by inhibiting fungal GPI biosynthesis, thereby inhibiting expression of cell wall assembly while preventing the fungus from attaching to cells so that the pathogen cannot become pathogenic, and 2) is excellent in terms of its properties, and particularly its solubility in water, its stability in an aqueous solution, and its safety and pharmacokinetics, making the above compounds extremely useful as a preventive or therapeutic agent for fungal infections.

I claim:

1. A compound represented by the following formula (I) or a salt thereof:

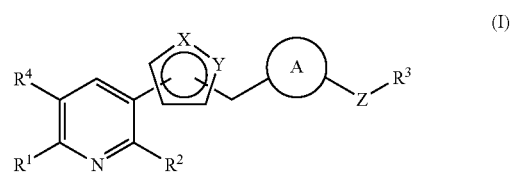

(I)

wherein $R^1$ represents a hydrogen atom, a halogen atom, an amino group, $R^{11}$—NH— (wherein $R^{11}$ represents a $C_1$ to $C_6$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^2$ represents a group represented by the formula:

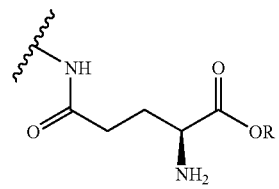

one of X and Y is a nitrogen atom while the other is a nitrogen atom or an oxygen atom;

ring A represents a 5- or 6-member heteroaryl ring or benzene ring which may have a halogen atom or 1 or 2 $C_1$ to $_6$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

$R^3$ represents a hydrogen atom or a halogen atom, or represents a $C_{1-6}$ alkyl group, a $C_{3-8}$ cycloalkyl group, a $C_{6-10}$ aryl group, a 5- or 6-member heteroaryl group, or a 5- or 6-member non-aromatic heterocyclic group, each of which may have 1 or 2 substituents selected from substituent group α;

$R^4$ represents a hydrogen atom or a halogen atom; and

R represents a hydrogen atom or a $C_{1-6}$ alkyl group which may be substituted with a dimethylamino group, substituent group α represents a halogen atom, a cyano group, a $C_{1-6}$ alkyl group, a $C_{1-6}$ alkoxy group, a $C_{1-6}$alkoxycarbonyl group, a $C_{3-8}$cycloalkyl group, a $C_{2-6}$alkenyl group and a $C_{2-6}$alkynyl group.

2. The compound or the salt thereof according to claim 1, wherein a partial structure represented by the formula (II):

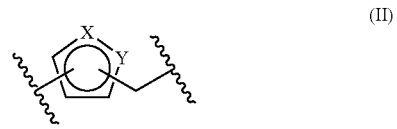

(II)

is a partial structure selected from the following group:

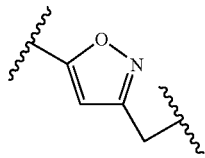
(III)

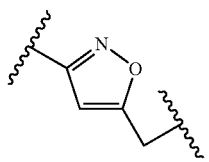
(IV)

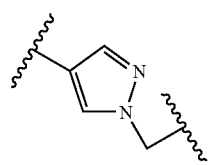
(V)

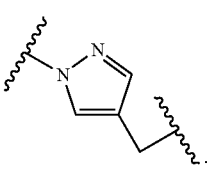
(VI)

3. The compound or the salt thereof according to claim 1, wherein one of X and Y is a nitrogen atom and the other is an oxygen atom.

4. The compound or the salt thereof according to claim 3, wherein a partial structure represented by the formula (II):

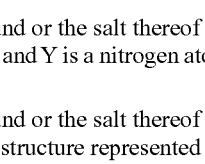
(II)

is a partial structure selected from the following formula (III):

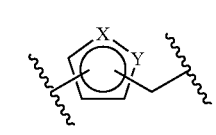
(III)

or is a partial structure selected from the following formula (IV):

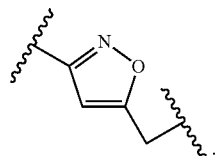
(IV)

5. The compound or the salt thereof according to claim 1, wherein X and Y are both nitrogen atoms.

6. The compound or the salt thereof according to claim 5, wherein a partial structure represented by the formula (II):

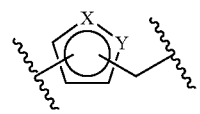
(II)

is a partial structure selected from the following formula (V):

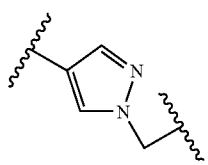
(V)

or is a partial structure selected from the following formula (VI):

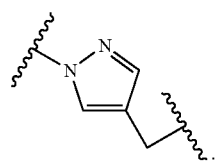
(VI)

7. The compound or the salt thereof according to any one of claims 1 to 6, wherein R represents a hydrogen atom, a methyl group, an ethyl group, or a 2-dimethylaminoethyl group.

8. The compound or the salt thereof according to claim 7, wherein $R^1$ represents a hydrogen atom, an amino group, or a $C_{1-6}$ alkoxy $C_{1-6}$ alkyl group.

9. The compound or the salt thereof according to any one of claims 1 to 6, wherein $R^1$ represents an amino group, and R represents a hydrogen atom, a methyl group, an ethyl group, or a 2-dimethylaminoethyl group.

10. The compound or the salt thereof according to any one of claims 1 to 6, wherein $R^1$ represents an amino group, and R represents a methyl group, an ethyl group, or a 2-dimethylaminoethyl group.

11. The compound or the salt thereof according to any one of claims 1 to 6, wherein the ring A represents a pyridine ring, a benzene ring, a furan ring, a thiophene ring, or a pyrrole ring.

12. The compound or the salt thereof according to claim 11, wherein the ring A represents a pyridine ring or a benzene ring.

13. The compound or the salt thereof according to any one of claims 1 to 6, wherein Z represents an oxygen atom, —$CH_2O$—, or —$OCH_2$—.

14. A pharmaceutical composition comprising the compound or the salt thereof according to any one of claims 1 to 6.

15. A medicament comprising the compound or the salt thereof according to any one of claims 1 to 6.

16. An antifungal agent comprising as an active ingredient the compound or the salt thereof according to any one of claims 1 to 6.

17. A method for treating a fungal infection comprising administering a pharmaceutically effective dose of the compound or the salt thereof according to any one of claims 1 to 6.

* * * * *